United States Patent
Dichterman et al.

(10) Patent No.: US 11,730,395 B2
(45) Date of Patent: Aug. 22, 2023

(54) RECONSTRUCTION OF AN ANATOMICAL STRUCTURE FROM INTRABODY MEASUREMENTS

(71) Applicant: Navix International Limited, Road Town (VG)

(72) Inventors: Eli Dichterman, Haifa (IL); Shlomo Ben-Haim, Milan (IT)

(73) Assignee: Navix International Limited, Road Town (VG)

( * ) Notice: Subject to any disclaimer, the term of this patent is extended or adjusted under 35 U.S.C. 154(b) by 715 days.

(21) Appl. No.: 16/639,610

(22) PCT Filed: Jul. 18, 2018

(86) PCT No.: PCT/IB2018/055344
§ 371 (c)(1),
(2) Date: Feb. 17, 2020

(87) PCT Pub. No.: WO2019/034944
PCT Pub. Date: Feb. 21, 2019

(65) Prior Publication Data
US 2020/0289025 A1    Sep. 17, 2020

Related U.S. Application Data

(63) Continuation-in-part of application No. PCT/IB2018/050192, filed on Jan. 12, 2018.
(Continued)

(51) Int. Cl.
*A61B 5/107*   (2006.01)
*A61B 5/06*   (2006.01)
(Continued)

(52) U.S. Cl.
CPC ........ *A61B 5/1076* (2013.01); *A61B 5/02028* (2013.01); *A61B 5/062* (2013.01);
(Continued)

(58) Field of Classification Search
None
See application file for complete search history.

(56) References Cited

U.S. PATENT DOCUMENTS

| | | |
|---|---|---|
| 5,465,730 A | 11/1995 | Zadehkoochak et al. |
| 5,553,611 A | 9/1996 | Budd et al. |

(Continued)

FOREIGN PATENT DOCUMENTS

| | | |
|---|---|---|
| CN | 101219061 | 7/2008 |
| CN | 101868182 | 10/2010 |

(Continued)

OTHER PUBLICATIONS

International Search Report and the Written Opinion dated Feb. 3, 2021 From the International Searching Authority Re. Application No. PCT/EP2020/075566. (28 Pages).

(Continued)

*Primary Examiner* — Katherine L Fernandez

(57) ABSTRACT

A method of reconstructing a shape of a volume of a part of a subject based on intrabody measurements of a plurality of crossing electromagnetic fields established within the volume, the method including:
 receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;
 generating, by computer circuitry and based on said measurement samples, a transformation that transforms measurement samples to geometric positions;
 transforming, using said generated transformation fewer than half of the measurements in said set of measurement samples into a set of geometric positions; and
(Continued)

reconstructing the shape of said volume from said set of geometric positions.

28 Claims, 13 Drawing Sheets

Related U.S. Application Data

(60) Provisional application No. 62/693,478, filed on Jul. 3, 2018, provisional application No. 62/546,775, filed on Aug. 17, 2017, provisional application No. 62/546,775, filed on Aug. 17, 2017, provisional application No. 62/445,433, filed on Jan. 12, 2017.

(51) Int. Cl.
　　A61B 5/00　　　　(2006.01)
　　A61B 5/02　　　　(2006.01)
　　G16H 50/50　　　(2018.01)
　　G16H 40/63　　　(2018.01)

(52) U.S. Cl.
　　CPC ........... *A61B 5/063* (2013.01); *A61B 5/1075* (2013.01); *A61B 5/4836* (2013.01); *A61B 5/6852* (2013.01); *G16H 40/63* (2018.01); *G16H 50/50* (2018.01)

(56) References Cited

U.S. PATENT DOCUMENTS

| | | |
|---|---|---|
| 5,662,108 A | 9/1997 | Budd et al. |
| 5,697,377 A | 12/1997 | Wittkampf |
| 6,240,307 B1 | 5/2001 | Beatty et al. |
| 6,640,119 B1 | 10/2003 | Budd et al. |
| 6,728,562 B1 | 4/2004 | Budd et al. |
| 6,826,420 B1 | 11/2004 | Beatty et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,187,973 B2 | 3/2007 | Hauck |
| 7,189,208 B1 | 3/2007 | Beatty et al. |
| 7,996,060 B2 | 8/2011 | Trofimov et al. |
| 2002/0077555 A1 | 6/2002 | Schwartz |
| 2003/0018251 A1 | 1/2003 | Solomon |
| 2003/0078494 A1 | 4/2003 | Panescu et al. |
| 2004/0254437 A1 | 12/2004 | Hauck et al. |
| 2005/0288586 A1 | 12/2005 | Ferek-Petric |
| 2006/0084859 A1 | 4/2006 | Johnson et al. |
| 2006/0247520 A1 | 11/2006 | McGee |
| 2007/0049817 A1 | 3/2007 | Preiss et al. |
| 2007/0299351 A1 | 12/2007 | Harlev et al. |
| 2007/0299352 A1 | 12/2007 | Harlev et al. |
| 2008/0009711 A1 | 1/2008 | Govari et al. |
| 2008/0242976 A1 | 10/2008 | Robertson et al. |
| 2009/0005846 A1 | 1/2009 | Zhu et al. |
| 2009/0076483 A1 | 3/2009 | Danehom |
| 2009/0171201 A1 | 7/2009 | Olson |
| 2009/0203992 A1 | 8/2009 | Govari et al. |
| 2009/0262109 A1 | 10/2009 | Markowitz et al. |
| 2009/0264778 A1 | 10/2009 | Markovitz et al. |
| 2012/0059249 A1 | 3/2012 | Verard et al. |
| 2012/0078129 A1 | 3/2012 | Bailin |
| 2013/0079628 A1* | 3/2013 | Groszmann ....... A61M 25/0127 600/424 |
| 2014/0275913 A1* | 9/2014 | Hill .................. A61B 5/065 600/373 |
| 2014/0275991 A1 | 9/2014 | Potter et al. |
| 2016/0045133 A1 | 2/2016 | Balachandran et al. |
| 2016/0061599 A1 | 3/2016 | Zeng et al. |
| 2016/0113709 A1 | 4/2016 | Maor |
| 2017/0020669 A1 | 1/2017 | Bartels et al. |
| 2018/0240237 A1* | 8/2018 | Donhowe ............ G06T 7/0014 |
| 2019/0336035 A1 | 11/2019 | Dichterman et al. |
| 2020/0000368 A1 | 1/2020 | Ben-Haim et al. |
| 2020/0085504 A1 | 3/2020 | Schwartz et al. |
| 2021/0128009 A1 | 5/2021 | Ben-Haim |

FOREIGN PATENT DOCUMENTS

| | | |
|---|---|---|
| CN | 102056537 | 5/2011 |
| CN | 103687533 | 3/2014 |
| CN | 105491952 | 4/2016 |
| CN | 105377135 | 6/2022 |
| EP | 0974936 | 1/2000 |
| EP | 1767166 | 3/2007 |
| EP | 2667823 | 12/2013 |
| EP | 3430999 | 1/2019 |
| JP | 2003/527164 | 9/2003 |
| RU | 2009142646 | 3/2010 |
| WO | WO 98/01069 | 1/1998 |
| WO | WO 2006/055286 | 5/2006 |
| WO | WO 2008/097767 | 8/2008 |
| WO | WO 2010/129095 | 11/2010 |
| WO | WO 2011/142931 | 11/2011 |
| WO | WO 2012/092016 | 7/2012 |
| WO | WO 2012/102928 | 8/2012 |
| WO | WO 2014/036439 | 3/2014 |
| WO | 2014091418 | * 6/2014 |
| WO | WO 2014/118535 | 8/2014 |
| WO | WO 2014/182822 | 11/2014 |
| WO | WO 2016/033599 | 3/2016 |
| WO | WO 2018/011757 | 1/2018 |
| WO | WO 2018/078540 | 5/2018 |
| WO | WO 2018/130974 | 7/2018 |
| WO | WO 2019/034944 | 2/2019 |
| WO | WO 2021/048420 | 3/2021 |

OTHER PUBLICATIONS

International Preliminary Report on Patentability dated May 9, 2019 From the International Bureau of WIPO Re. Application No. PCT/IB2017/056616. (8 Pages).
International Preliminary Report on Patentability dated Aug. 22, 2019 From the International Bureau of WIPO Re. Application No. PCT/IB2018/050784. (11 Pages).
International Preliminary Report on Patentability dated Jul. 25, 2019 From the International Bureau of WIPO Re. Application No. PCT/IB2018/050192. (8 Pages).
International Preliminary Report on Patentability dated Feb. 27, 2020 From the International Bureau of WIPO Re. Application No. PCT/IB2018/055344. (8 Pages).
International Preliminary Report on Patentability dated Feb. 27, 2020 From the International Bureau of WIPO Re. Application No. PCT/IB2018/056158. (8 Pages).
International Search Report and the Written Opinion dated Feb. 1, 2018 From the International Searching Authority Re. Application No. PCT/IB2017/056616. (14 Pages).
International Search Report and the Written Opinion dated May 9, 2018 From the International Searching Authority Re. Application No. PCT/IB2018/050192. (16 Pages).
International Search Report and the Written Opinion dated Nov. 30, 2018 From the International Searching Authority Re. Application No. PCT/IB2018/055344. (15 Pages).
Crospon "Esophageal Treatment by Esoflip®", Crospon, Product Sheet, 4 P., 2017.
Crospon "Flip® Technology", Crospon, Product Sheet, 6 P., 2017.
Myronenko et al. "Non-Rigid Point Set Registration: Coherent Point Drift", Advances in Neural Information Processing Systems, NIPS, 19: 1009-1016, 2009.
International Preliminary Report on Patentability dated Mar. 15, 2022 From the International Bureau of WIPO Re. Application No. PCT/EP2020/075566. (17 Pages).
Interview Summary dated May 3, 2022 from US Patent and Trademark Office Re. U.S. Appl. No. 16/484,501. (3 pages).
Invitation to Pay Additional Fees, Communication Relating to the Results of the Partial International Search and the Provisional

(56) References Cited

OTHER PUBLICATIONS

Opinion dated Dec. 8, 2020 From the International Searching Authority Re. Application No. PCT/EP2020/075566. (24 Pages).
Official Action dated May 5, 2021 from the US Patent and Trademark Office Re. U.S. Appl. No. 16/476,875. (35 pages).
Notification of Office Action and Search Report dated Jan. 11, 2022 From the State Intellectual Property Office of the People's Republic of China Re. Application No. 201880022135.4. (8 Pages).
Notification Regarding Third-Party Preissuance Submission dated Jan. 29, 2021 From the US Patent and Trademark Office Re. U.S. Appl. No. 16/338,710.(2 Pages).
Third Party IDS Submission under 37 CFR 1.290 filed on Jan. 14, 2021 From the US Patent and Trademark Office Re. U.S. Appl. No. 16/338,710.(2 Pages).
Official Action dated Jun. 4, 2021 from the US Patent and Trademark Office Re. U.S. Appl. No. 16/338,710. (22 pages).
Official Action dated Jan. 27, 2022 From the US Patent and Trademark Office Re. U.S. Appl. No. 16/484,501. (36 Pages).
Notification of Office Action and Search Report dated Nov. 10, 2022 From the State Intellectual Property Office of the People's Republic of China Re. Application No. 201880055476.1 and its Summary in English. (15 Pages).
Bailin et al. "Direct Visualization of the Slow Pathway Using Voltage Gradient Mapping: A Novel Approach for Successful Ablation of Atrioventricular Nodal Reentry Tachycardia", EP Europace, 13(8): 1188-1194, Published Apr. 19, 2011.
Casella et al. "Rationale and Design of the NO-PARTY Trial: NearZero Fluoroscopic Exposure During Catheter Ablation of Supraventricular Arrhythmias in Young Patients", Cardiology in the Young, 22(5): 539-546, Sep. 13, 2012.
Eitel et al. "EnSite Elocity™ Cardiac Mapping System: A New Platform for 3D Mapping of Cardiac Arrhithmias", Expert Review of Medical Devices, 7(2): 185-192, Published Jan. 9, 2014.

\* cited by examiner

RECONSTRUCTION OF AN ANATOMICAL STRUCTURE FROM INTRABODY MEASUREMENTS

RELATED APPLICATIONS

This application is a National Phase of PCT Patent Application No. PCT/IB2018/055344 having International filing date of Jul. 18, 2018, which claims the benefit of priority under 35 USC § 119(e) of U.S. Provisional Patent Application Nos. 62/693,478 filed on Jul. 3, 2018 and 62/546,775 filed on Aug. 17, 2017.

PCT Patent Application No. PCT/IB2018/055344 is also a Continuation-In-Part (CIP) of PCT Patent Application PCT/IB2018/050192 having International filing date of Jan. 12, 2018, which claims the benefit of priority under 35 USC § 119(e) of U.S. Provisional Patent Application Nos. 62/445,433 filed on Jan. 12, 2017 and 62/546,775 filed on Aug. 17, 2017.

The contents of the above applications are all incorporated by reference as if fully set forth herein in their entirety.

FIELD AND BACKGROUND OF THE INVENTION

The present invention, in some embodiments thereof, relates to the field of navigation of body cavities by intrabody probes, and more particularly, to reconstruction of body cavity shape from measurements by intrabody probes.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems.

SUMMARY OF THE INVENTION

Some examples of embodiments of the invention follows. It should be noted that some embodiments of the invention include features from multiple examples and/or can include fewer than all features described in one example.

Example 1

A method of reconstructing a shape of a volume of a part of a subject based on intrabody measurements of a plurality of crossing electromagnetic fields established within the volume, the method comprising:

receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;

generating, by computer circuitry and based on said measurement samples, a transformation that transforms measurement samples to geometric positions;

transforming, using said generated transformation fewer than half of the measurements in said set of measurement samples into a set of geometric positions; and reconstructing the shape of said volume from said set of geometric positions.

Example 2

A method according to example 1, wherein transforming fewer than half of the measurements, comprises transforming using fewer than 25% of the measurements, said measurements selected to increase a spatial uniformity of said measurement samples.

Example 3

A method according to example 1 or example 2, comprising normalizing said measurement samples prior to said generating a transformation.

Example 4

The method of any of examples 1-3, wherein the generating is performed without use of a distance to a reference position outside of said part of the subject.

Example 5

The method of any one of examples 1-4, wherein the generating is performed without use of an orientation or direction to a reference position outside of said part of the subject.

Example 6

The method of any one of examples 1 to 5, wherein the generating is performed independent of any information about the shape of said volume.

Example 7

The method of any of examples 1-6, wherein said reconstructing the shape of said volume from said set of geometric positions comprises reconstructing based on said set of geometric positions and an external reference position.

Example 8

The method of any of examples 1-7, wherein said generating comprises using at least 30 positions of said set as reference positions for other positions of said set.

Example 9

The method of any of examples 1-8, wherein said generating uses only reference positions within said part of a subject.

Example 10

A method according to any of examples 1-9, wherein said generating is constrained using one or more constraints.

Example 11

A method according to example 10, wherein said one or more constraints comprise a constraint on relative positions of a plurality of positions to which measurement samples are transformed.

Example 12

A method according to example 11, wherein said constraint applies to geometrical relationships between local positions, all within a radius of less than 20% of a maximal radius of said reconstructed volume.

Example 13

A method according to example 12, wherein a constraint comprises a coherence requirement.

Example 14

A method according to any of examples 11-13, wherein said geometrical relationship comprises distance.

Example 15

A method according to any of examples 10-14, wherein said one or more constraints comprise a constraint on the measurement samples.

Example 16

A method according to any of examples 10-15, wherein said one or more constraints comprise a constraint on a relationship between one or more measurement samples and one or more of said set of positions.

Example 17

A method according to any of examples 10-16, wherein said generating comprises allowing two samples acquired at locations having a known distance therebetween to be transformed into positions at a different distance therebetween.

Example 18

A method according to any of examples 1-17, wherein said generated transformation is not isotropic and varies by at least an order of magnitude.

Example 19

A method according to any of examples 1-18, wherein generating a transformation comprises searching for a transformation under conditions of one or more constraints.

Example 20

The method of example 19, wherein generating a transformation comprises
test-generating a plurality of transformations from the measurements based on different parameters;
evaluating each of the plurality of transformations according to a cost function; and
generating the transformation based on the evaluating.

Example 21

The method of example 20, wherein a plurality of pairs of measurements, which are transformed into a corresponding plurality of pairs of positions, are associated with a desired pair-distance, and the cost function comprises a distance distortion penalty term that increases with an increase in absolute value of a difference between the distance within a said pair of positions and its corresponding desired pair-distances.

Example 22

The method of any one of examples 20-21, wherein generating the plurality of test-transformations comprises ignoring measurements, provided that said ignoring decreases the cost function by more than a predetermined decrease.

Example 23

The method of any one of examples 20-22, wherein the cost function comprises an anti-flattening penalty term wherein the anti-flattening penalty term increases as variance measured along an axis of the set of measurement samples becomes reduced relative to other axes of said set.

Example 24

The method of any one of examples 20 to 22, wherein the cost function comprises a sum of the multiplicative inverses of scaling coefficients used to perform the transforming.

Example 25

A method according to any of examples 1-24, wherein generating a transformation comprises modifying an existing transformation based on addition of measurement samples.

Example 26

The method of any one of examples 1-25, wherein generating a transformation comprises minimizing variability in distances between positions assigned to nearby measurements.

Example 27

The method of example 26, wherein said minimizing is applied to subsets of measurements of the crossing electromagnetic fields measured substantially simultaneously by at least two sensors carried on the intrabody probe.

Example 28

The method of example 27, wherein a criterion of reducing variability comprises reducing differences between a transformation-based distance between transformed measurements and a known distance between locations of said measurements.

Example 29

The method of any of examples 1-28, wherein: said generating comprises determining for each of said crossing electromagnetic fields a corresponding scaling coefficient, applicable to scale measurements of each said crossing electromagnetic field for said transformation into positions.

Example 30

The method of example 29, wherein the scaling coefficients define together a vector a, and the measurements define together a measurement matrix X, and the scaling coefficients are applicable to each set member according to an expression product diag(a)X.

Example 31

The method of any one of examples 29-30, wherein said generating comprises determining positional displacements applicable to each scaled measurement of each of the crossing electromagnetic fields.

Example 32

The method of example 31, wherein the displacements are determined based on an intrinsic geometry of a measurement cloud consisting of the measurements.

Example 33

The method of any of examples 1-32, comprising scaling the measurement samples along different axes defined according to said crossing fields prior to said generating.

Example 34

The method of any of examples 1-33, comprising adjusting said set of positions and/or said shape responsive to a geometrical constraint after said transforming.

Example 35

The method of any of examples 1-34, comprising reducing a dimension of said measurement samples before said transforming.

Example 36

The method of any of examples 1-35, comprising scaling, translating and/or orientating said set of positions or said shape after said transforming.

Example 37

The method of any of examples 1-36, wherein said measurement samples comprise voltage measurements of said fields.

Example 38

The method of any of examples 1-37, wherein said measurement samples comprise simultaneous measurements of multiple fields at one point, wherein each field has a different variation in a parameter thereof as a function of time.

Example 39

The method of any of examples 1-37, wherein said measurement samples comprise at least 8 measurement values per measurement sample.

Example 40

The method of any of examples 1-39, wherein each position in said set of position includes a 3D spatial position.

Example 41

The method of any of examples 1-40, wherein each position in said set of position includes a timestamp.

Example 42

The method of any of examples 1-41, wherein each position in said set of position includes a phase indication for a physiological cycle.

Example 43

The method of any of examples 1-42, wherein at least one of said measured fields are generated by said probe.

Example 44

A method according to any of examples 1-43, wherein reconstructing the shape comprises reconstructing the shape from the set of geometrical positions using a ball-pivoting algorithm.

Example 45

A method according to any of examples 1-44, wherein reconstructing the shape comprises reconstructing the shape from the set of geometrical positions using topological operators including dilation and erosion.

Example 46

A method according to any of examples 1-45, wherein reconstructing the shape comprises reconstructing the shape of a heart or a part thereof.

Example 47

An apparatus for reconstructing a body cavity shape of a subject based on intrabody measurements of a plurality of crossing electromagnetic fields established within the body cavity, the apparatus comprising:
  computer circuitry, configured to
  receive measurements of the crossing electromagnetic fields using at least two sensors carried on an intrabody probe, the measuring being carried out with the probe at multiple locations in the body cavity; and
  reconstruct a 3D model of the body cavity shape based on comparison between the measurements, by finding a transformation from said measurements to a geometric space, using fewer than half of said measurements;
  and
  a display, configured to display at least an indication of the reconstructed 3D model.

Example 48

The apparatus of example 47, wherein the comparison of the measurements comprises comparison of distances between the measurements.

Example 49

A system for reconstructing a body cavity shape of a subject, the system configured to carry out any one of examples 1-46.

Example 50

A method of reconstructing a shape of a volume of a part of a subject based on intrabody measurements of a plurality of crossing electromagnetic fields established within the volume, the method comprising:
  receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;

generating, by computer circuitry and based on said measurement samples, a transformation that transforms measurement samples to geometric positions; wherein the generating is performed without use of a distance to a reference position outside of said part of the subject;

transforming, using said generated transformation, said set of measurement samples into a set of geometric positions;

and reconstructing the shape of said volume from said set of geometric positions.

Example 51

A method of reconstructing a shape of a volume of a part of a subject based on intrabody measurements of a plurality of crossing electromagnetic fields established within the volume, the method comprising:

receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;

generating, by computer circuitry and based on said measurement samples, a transformation that transforms measurement samples to geometric positions; wherein the generating is performed without use of an orientation or direction to a reference position outside of said part of the subject;

transforming, using said generated transformation, said set of measurement samples into a set of geometric positions;

and reconstructing the shape of said volume from said set of geometric positions.

Example 52

A method of reconstructing a shape of a volume of a part of a subject based on intrabody measurements of a plurality of crossing electromagnetic fields established within the volume, the method comprising:

receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;

generating, by computer circuitry and based on said measurement samples, a transformation that transforms measurement samples to geometric positions, wherein said generating uses only reference positions within said part of a subject;

transforming, using said generated transformation, said set of measurement samples into a set of geometric positions;

and reconstructing the shape of said volume from said set of geometric positions.

Example 53

A method of reconstructing a shape of a volume of a part of a subject based on intrabody measurements of a plurality of crossing electromagnetic fields established within the volume, the method comprising:

receiving, by computer circuitry, measurements of the crossing electromagnetic fields carried out using at least one sensor carried on an intrabody probe, the measuring being carried out with the probe at multiple locations in the volume, to provide a set of measurement samples, each taken at a location;

generating, by computer circuitry and based on said measurement samples, a transformation that transforms measurement samples to geometric positions, wherein said generating is constrained using one or more constraints;

transforming, using said generated transformation, said set of measurement samples into a set of geometric positions;

and reconstructing the shape of said volume from said set of geometric positions.

Some additional examples follow:

Additional Example 1

A method of reconstructing a body cavity shape of a subject based on intrabody measurements of a plurality of crossing electromagnetic fields established within the body cavity, the method comprising:

receiving, by computer circuitry, measurements of the crossing electromagnetic fields carried out using at least two sensors carried on an intrabody probe with a geometrical relationship between them, the measuring being carried out with the probe at multiple locations in the body cavity; and reconstructing, using the computer circuitry, positions at which the measurements were taken relative to each other, based on applying one or more constraints on a reconstruction using different ones of the measurements, the constraints defining a relationship between measurements and/or positions; and displaying a model of the body cavity shape based on the reconstructed positions.

Additional Example 2

The method of additional example 1, wherein the reconstructing is performed without use of a distance to an external reference measurement.

Additional Example 3

The method of any one of additional examples 1-2, wherein the reconstructing is performed without use of an orientation or direction to an external reference measurement.

Additional Example 4

The method of any one of additional examples 1-3, wherein the comparison of the different ones of the measurements comprises comparison of distances between the measurements.

Additional Example 5

The method of any one of additional examples 1-4, wherein the reconstructing comprises assigning the measurements of the crossing electromagnetic fields to locations so that variability in distances between sister locations is minimized.

Additional Example 6

The method of additional example 5, wherein sister locations are locations assigned to sister measurements, and sister measurements are measurements of the crossing electromagnetic fields measured substantially simultaneously by the at least two sensors carried on the intrabody probe at the known distance from each other.

Additional Example 7

The method of additional example 6, wherein a criterion of reducing variability comprises reducing differences between distances of sister locations and the known distance.

Additional Example 8

The method of additional example 1, wherein: the reconstructing comprises determining for each of said crossing electromagnetic fields a corresponding scaling coefficient, applicable to scale measurements of each said crossing electromagnetic field.

Additional Example 9

The method of additional example 8, wherein the scaling coefficients define together a vector a, and the measurements define together a measurement matrix X, and the scaling coefficients are applicable to each set member according to an expression product diag(a)X.

Additional Example 10

The method of any one of additional examples 8-9, wherein the reconstructing comprises determining displacements applicable to each scaled measurement of each of the crossing electromagnetic fields.

Additional Example 11

The method of additional example 10, wherein the displacements are determined based on an intrinsic geometry of a measurement cloud consisting of the measurements.

Additional Example 12

The method of any one of additional examples 1-11, wherein the reconstructing comprises:
reconstructing a plurality of reconstructions from the measurements based on different parameters;
evaluating each of the plurality of reconstructions according to a cost function; and
providing a reconstructions for the displaying, based on the evaluating.

Additional Example 13

The method of additional example 12, wherein each pair of sister measurements is associated with a desired sister distance, and the cost function comprises a distance distortion penalty term that increases as absolute differences between sister distances and their corresponding targeted sister distances increase.

Additional Example 18

A method according to any one of the preceding additional examples, wherein displaying a model of the body cavity shape based on the reconstructed positions comprises generating the model from the reconstructed positions using a ball-pivoting algorithm.

Additional Example 19

A method according to any one of the preceding additional examples, wherein displaying a model of the body cavity shape based on the reconstructed positions comprises generating the model from the reconstructed positions using dilation and erosion.

Additional Example 20

The method according to any one of the preceding additional examples, wherein the reconstructing is absent prior information on the body cavity shape.

Additional Example 22

The method of any one of the preceding additional examples, wherein the reconstruction comprises searching for a transformation that minimizes a cost function, and the cost function is configured to penalize transformations into R-clouds which are relatively collapsed along one dimension.

Additional Example 24

An apparatus for reconstructing a body cavity shape of a subject based on intrabody measurements of a plurality of crossing electromagnetic fields established within the body cavity, the apparatus comprising:
computer circuitry, configured to
receive measurements of the crossing electromagnetic fields using at least two sensors carried on an intrabody probe, the measuring being carried out with the probe at multiple locations in the body cavity; and
reconstruct a 3D model of the body cavity shape based on comparison between the measurements; and
a display, configured to display the reconstructed 3D model.

Additional Example 25

The apparatus of additional example 24, wherein the comparison of the measurements comprises comparison of distances between the measurements.

Additional Example 26

A system for reconstructing a body cavity shape of a subject, the system configured to carry out any one of additional examples 1 to 23.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings.

DESCRIPTION OF SPECIFIC EMBODIMENTS OF THE INVENTION

Figure 1A:
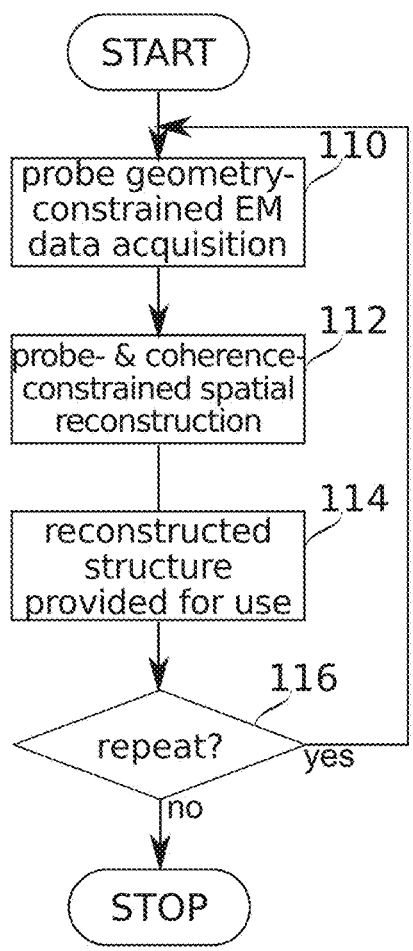
FIG. 1A is a schematic flowchart of a method for reconstructing a body cavity shape using an intrabody probe, according to some exemplary embodiments of the present disclosure.

The present invention, in some embodiments thereof, relates to the field of navigation of body cavities by intrabody probes, and more particularly, to reconstruction of body cavity shape from measurements by intrabody probes.

Overview

An aspect of some embodiments of the present invention relates to reconstruction of a body cavity shape of a subject (e.g., a patient undergoing a catheterization procedure) based on measurements from a plurality of sensors (e.g., an intrabody probe carrying a plurality of sensors such as electrodes, optionally occupying known spaced positions relative to the geometry of the intrabody probe). The term "cavity" is used as a specific example in various of the embodiments of the invention described herein, as a probe can have relative freedom of movement in such a cavity. However, the methods and apparatus described herein may also be used for body volumes that are not completely hollow (e.g., volumes of body parts), for example, with a probe damaging the tissue in the volume to collect measurements at different locations or with a probe moving within natural channels, such as blood vessels, in the volume.

In some embodiments, the reconstruction (process) may include generating a 3D model of the body volume shape (a resulting reconstruction product). For example, a transformation (also referred to herein as transform or transform function) transferring measurements to locations may be defined using some parameters, and values for such parameters, under which the transformation obeys some constraints are searched to provide a transformation from a cloud of measurements to a corresponding cloud of locations which may be represented as a set of geometrical positions. The 3D model of the body cavity may be obtained from this cloud of locations using a known method, for example, the ball pivoting algorithm or using erosion and dilation topological operations applied to geometric positions (optionally on a shell) or using other shell reconstructing methods, for example, finding abounding shell and smoothing it. It is noted that this last act, of reconstructing the shape is optional and some embodiments may use the set of geometrical position for uses other than 3D shape reconstruction. In particular, in any of the embodiments described below, "reconstruction" methods may include transforming but the actual reconstruction of a shape may be omitted.

In some embodiments, the reconstruction process and/or in particular the transformation, is based (substantially) only on measurements and rules (for example constrains) pertaining to relationships between such measurements and/or positions, and is independent of one or more (or all) of specified frame of reference, such as a patient's bed, a prior knowledge of the body cavity shape, a pre-acquired image of the body cavity shape, or the like. In some embodiments, the reconstruction process is guided by known spatial constraints such as distances between the relative positions of the plurality of sensors on the probe. Optionally, local spatial calibration defined by constraints on a transformation from measurements to locations is used, optionally in combination with constraints on the spatial coherence of such a transformation. An example of the concept of spatial coherence is explained in passages under the subtitle "Coherence constraints on reconstruction". In some embodiments of the invention, constraints are applied to sets of measured values (also termed "cloud of measurements") and are used for reconstruction, for example, by comparing, aligning and/or mathematically processing of such measured values. For example, a mathematical processing may include fitting a model which explains the measured values. In some embodiments of the invention, constraints are applied to the measurements (cloud of measurements) and are used for reconstruction—for example: may be used for generating and/or selecting a transformation function from measurement space to position space.

In some embodiments of the invention, a plurality of measurements and/or locations are used as reference points for other locations and/or measurements for generating the transformation, for example, at least 10, at least 20, at least 50 or intermediate numbers of measurements and/or locations are used as references, for, for example, at least 10, at least 20, at least 50 or intermediate numbers of other measurements and/or locations. For example, 10 or more points may serve as references (e.g., for spatial comparison purposes) to 10 or more other points.

In some embodiments of the invention, while the measurements are used to generate a transformation, not all the measurements are so used and/or are transformed. For example, more than 50%, 70%, 90%, 95% or intermediate percentages of measurements are ignored for generating and/or using the transformation. Optionally, a transformation (e.g., of a heart chamber) uses at least 50, 100, 1000, 5000, 10,000 and/or intermediate numbers of measurements.

In some embodiments of the invention, the constraints used for generating a transformation are not known ahead of time and are calculated as part of the reconstruction process. In others, the constraints may be estimated ahead of time but optionally modified due to the reconstruction. For example, reconstruction may be based on a fixed distance between sensors (e.g., electrodes) on a catheter or other probe. Optionally, this fixed distance is recalculated based on the reconstruction, for example, changing in order to support a better reconstruction (e.g., which has a lower apparent error based on the measurements acquired). Optionally or additionally, in some embodiments data on the shape of an organ, for example, it being hollow and possibly generally spheroid or ellipsoid, may be used. Optionally, no data on exact (e.g., within 10% or 5% or better) orientation and/or scaling is used during reconstruction, optionally after reconstruction, such data is used.

As used herein, the term "reconstruction" is used (as are related word forms, e.g., "reconstruct" and "reconstructing") to indicate a process of and/or process product from the generation of a representation of a three dimensional (3-D) shape of a target, based on position data used as indications of positions within the target. Herein, positions "within" a target should be understood to include periphery and/or surface positions of the target.

In some embodiments, reconstruction includes mapping from a set of measurements in a position data space (e.g., measurements of a plurality of distinguishable electromagnetic fields, wherein each of the fields contributes at least one dimension to the position data space) to corresponding positions in a physical/geometric space at which those measurements are made. In some embodiments, reconstruction includes mapping from V-cloud to R-cloud.

Figure 2:
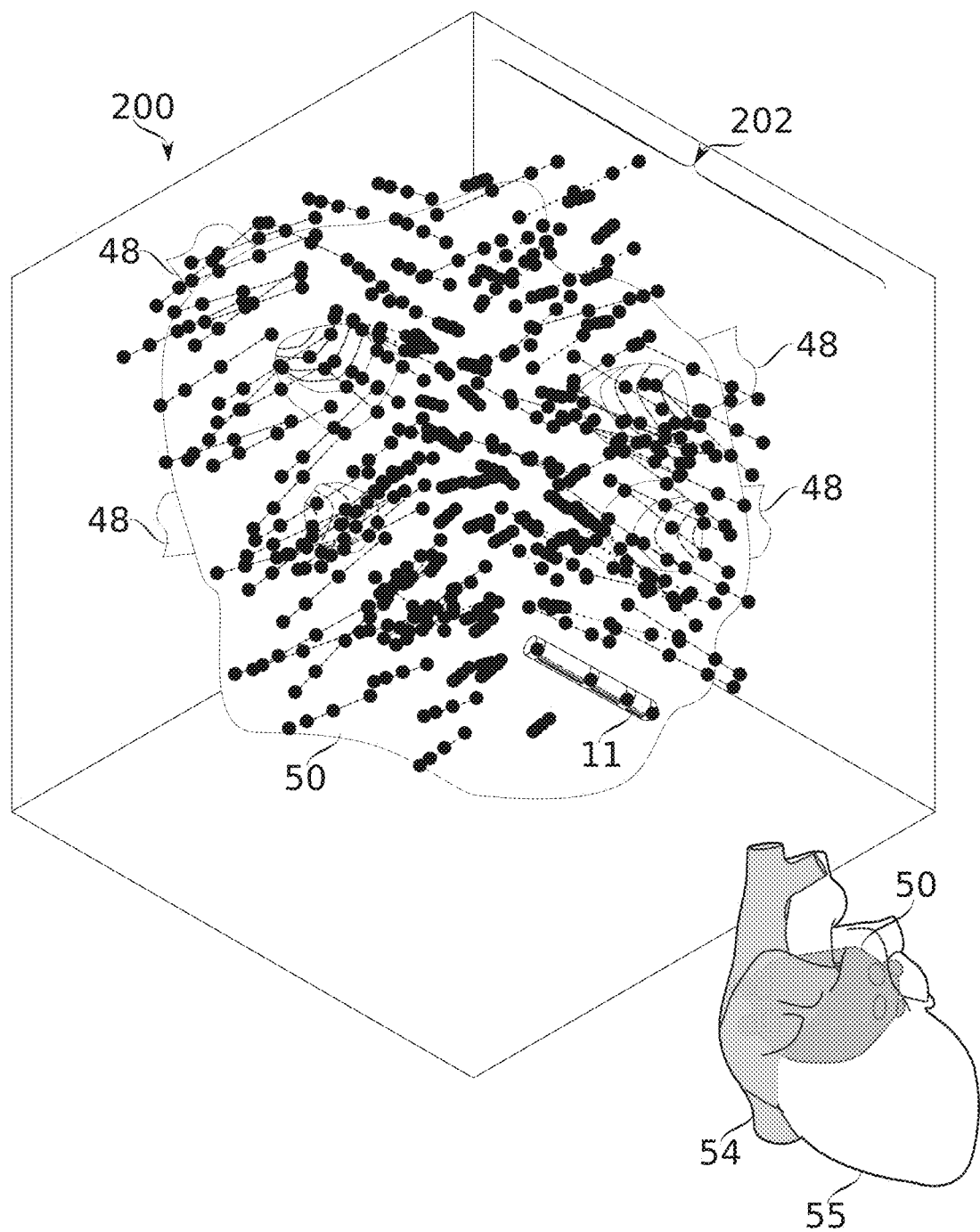
FIG. 2 schematically represents sample positions of a voltage sample cloud shown mapped via a voltage/spatial mapping to a space representing a cavity of a left atrium of a heart.

The collection of measurements (e.g., of voltage measurements or other electrical and/or other measurements, for example as measured from intrabody probe) is optionally referred to as a "V-cloud"; that is, a cloud of measurements in measurement space. The term "V-cloud" may also refer to a voltage sample cloud, for example as illustrated in FIG. 2. The term V-cloud may refer to set of measurement samples. The measurements are, for example, of crossing electromagnetic fields, for example, voltage measurements and/or impedance measurements. The measurements may be measurements of the crossing electromagnetic fields carried out using sensor(s) carried on an intrabody probe, the measuring being carried out with the probe at multiple locations in the body cavity.

While the application, in many embodiments, focuses on electric fields and in particular voltage measurements, it is noted that methods as described herein may be applied to other field measurements, for example, measurements of AC or pulsed magnetic fields and measurement of ultrasonic and/or optical fields. For example, suitable sensors may be mounted on the probe and suitable field sources may be provided outside the body. In some embodiments, suitable sensors and suitable field sources may be mounted on the probe (or otherwise connected to probe electrodes which may be used for transmitting). Optionally, the same electrodes of the probe may be used for transmitting and receiving (measuring).

More generally, every parameter characterizing the electromagnetic field may serve to measure the electromagnetic fields. Herein, the term "physical space" is used to refer to the range of physical locations over which the target extends, and the term "measurement space" is used to refer to the range over which the measurements extend. The physical space is at least three-dimensional, as it has height, width, and depth (and optionally also time), and the dimensionality of the measurement space depends, inter-alia, on the number of frequencies used for the measurements (or other means for distinguishing fields, such as symbol encoding), where, for example, each frequency corresponds to one dimension. The collection of positions in the physical space, to which the measurements making the V-cloud are transformed, is optionally referred to as an "R-cloud". R-cloud may also refer to a cloud of locations, which may be represented as a set of geometrical positions. In some embodiments, the 3-D shape of the reconstruction is represented as a 3-D mesh, for example, a 3-D mesh that bounds all the positions in the R-cloud. Optionally, the 3-D mesh is defined by the path of a sphere or other geometrical shape sliding over the R-cloud; wherein the size of the sphere defining how deeply the sphere can penetrate between mesh points, so that the mesh surface is made relatively smooth. In some embodiments of the invention, the 3-D shape is represented as a set of voxels or using a different non-mesh representation. It is noted that while the fields may be crossing simultaneously, in some embodiments the fields are not simultaneously active so they do not cross at particular points in time.

It should be emphasized that the conversion, for example by transforming measurement samples from a V-cloud to positions in an R-cloud, in some embodiments, is performed based on relationships among the measurements of the V-cloud (and/or relationships among results of transformation into the R-cloud), and optionally, relationships between measurements of the V-cloud (and/or results of transformation into the R-cloud) and known distances between the sensors that measure these measurements, and without use of an externally specified spatial frame of reference.

In some cases, the term mapping is used to reflect a correspondence between samples in the V-cloud and positions in the R-cloud. This should not be confused with intrabody mapping whereby a probe is used to collect data at various locations and a map of this data is later used (e.g., by a physician), for example, for navigation.

In some embodiments, the reconstruction and/or transformation is performed without using information regarding the location and/or orientation of an external reference, such as any object outside of the reconstructed region. For example, information regarding the location of the patient's bed, a fiducial marker on the patient's body, or the like, is not required for the reconstruction to take place. Thus, the patient may move (e.g., in respect to the bed, or move his arm so as to change the orientation of his heart inside his body) without affecting the reconstruction. The reconstruction and/or transformation may be carried out without being provided with measurement results or estimate of an orientation and/or direction with respect to one or more external (e.g., external to the set of geometrical positions being used for reconstruction and/or other than provided by the probe and/or other than being within a reconstructed organ and/or reconstructed shape) reference locations.

Furthermore, the reconstruction and/or transformation may take place absent any prior information on the body cavity shape to be reconstructed, and, in some embodiments, does not require a pre-acquired image of the body cavity (or other volume). By "external location" is meant a location outside of the resulting R-cloud, for example, a location outside the body of a patient within which the measurement of the V-cloud is performed, or, for example, a location more than 2 cm, 5 cm, 8 cm or intermediate distances away from the part of body being reconstructed. For example, in some embodiments, the V-cloud alone is used to create an R-cloud in a physical space defined without reference to reference points, landmarks, etc. which exist outside of what is available by transformation from the V-cloud itself. Optionally, orientation of the R-cloud (e.g., for purposes of presentation) is determined from features of the V-cloud and/or reconstructed R-cloud. For example, arrangements of R-cloud features such as blood vessels, valves, appendages, wall curvatures, and the like may be used to identify anatomical axes, rather than the anatomical axes being imposed from separately measured constraints.

In some embodiments, reconstructing a body cavity shape of a subject based on intrabody measurements of a plurality of crossing electromagnetic fields is performed based on relationships among the measurements and/or positions, and without use of an externally specified spatial frame of reference. For example, the reconstructing is performed without using any external reference locations.

In some embodiments of the present invention, the target whose shape is to be reconstructed, generally referred to herein as "the target" is a body cavity; wherein the positions indicated by the position data comprise positions within the body cavity shape. The reconstructed representation models at least the target's shape. Optionally, the reconstructed representation represents additional target properties associated with the target shape and/or locations thereon, for example, tissue type, electrical and/or dielectric properties, or another property.

The process of reconstruction is optionally supplemented by further information such as a template shape that is transformed to match available position data and/or used as a template shape to which available position data are transformed. In some embodiments, the reconstructed representation comprises and/or is presentable as an image of the target shape. For example, a reconstructed 3-D representation modeling a body cavity is rendered to an image of the body cavity using 3-D rendering software. Optionally, a reconstructed 3-D representation is subject to pre-processing transformation of its position data (e.g., unwrapping, flattening, or another transformation) before production of an image of the reconstructed representation.

The term "position data" is used herein to refer generally to data used to determine spatial positions. In some embodiments, at least some of the position data used are obtained in the form of measurements of one or more physical characteristics of the tissue environment at a probe's current position. The probe, in some embodiments, is an electrode probe, and the measurements are electrical measurements. Additionally or alternatively, position data comprises image data. Position data can also be provided as constraints, e.g., to provide context to other position data and help in defining the spatial position that the position data indicates.

Herein the term "constraint" is used in several descriptions to refer to conditions imposed on a transformation from measurement space to physical space. Constraints may refer to conditions imposed on a transformation from V-cloud to R-cloud. The constraints may reflect information and/or assumptions that limit possible measurements, locations (in physical space), and relationships between measurements and locations. Constraints are optionally not used as "hard constraints", i.e., sometimes, they may not be fully obeyed, e.g., simultaneous measurements from a plurality of electrodes may be "constrained" to be assigned to locations separated by fixed distances from each other, but in practice may be assigned to locations of slightly different distances. This may occur due, for example, to measurement errors, competing constraints, features of an algorithm used for minimization of error in assigned positions, etc. As used herein, the term "to minimize" and its inflections (such as minimizing, minimization, etc.) refer to attempt to reach a smallest (or close to smallest) possible value under given conditions, but does not guarantee that the attempt is fully successful. For example, in some embodiments, minimization is carried out iteratively with a convergence criterion, determining when to stop the iterations. Applying a different convergence criterion may lead to a smaller value (e.g., by spending on the minimization longer computation time). Still, the value obtained is referred to as minimized, although a smaller value could have been found, for example, by a different minimization mechanism, by a different convergence condition, etc.

In some embodiments, the intrabody probe is a catheter probe moved within the body cavity (e.g., a heart chamber such as an atrium or ventricle of a mammalian heart) to different positions at which sets of measurement samples are taken from the plurality of sensors. Such "sets" are optionally taken to be comprised of measurements taken at substantially the same time and/or while the catheter probe remains substantially in a same position, so that members of each set may be related to one another through application of mutual position constraints (such as known relative distance).

The plurality of sensors, in some embodiments, are probe-borne detection elements of measurement-taking devices; e.g., electrodes, or another device, for example, magnetic field sensor, sound field detector, photon detector, or the like. As used herein, the term "sensor" is used to indicate any device capable of measuring and/or sensing the field, for example any sensor for measuring electrical fields. Sensor may include or may be electrodes, e.g., electrodes provided on intrabody probe. In some embodiments, sensor(s) may be used to measure and/or sense V-cloud. In some embodiments, sensors may be used also to transmit (e.g., one or more electrodes used for sensing may also be used for transmitting electrical fields). Sensor-produced position data suitable for use with some embodiments of the current invention comprise sensed data which "tags" or otherwise helps identify particular positions occupied by the data-acquiring sensor. In some embodiments, the identifying is based on sensing positions within one or more artificially established fields of electrical voltages, sound (e.g., ultrasound), magnetic forces, electromagnetic radiation, particle radiation, and/or another field. Herein, electrode-based sensing of electrical voltages is used as a main example, but it should be understood that other position sensing methods are optionally used with methods described herein, changed as necessary.

The measurements are of one or more parameters treated singly or in combination as identifying of particular locations within the body cavity for purposes of reconstruction and in particular, for example, generating a transformation. Optionally, the parameters are treated as being identifiers of particular locations under particular conditions (e.g., heart-beat phase and/or respiratory phase). In some embodiments, the measurements comprise measurements of voltages within crossed, time-varying electromagnetic fields.

To distinguish the fields, in some embodiments, the crossed electromagnetic fields vary at distinguishable frequencies and/or use a different temporal code. As used herein, crossed or crossing fields are fields directed in directions that are not parallel to each other, nor anti-parallel, so that the direction of each field crosses the directions of all the other fields. Crossing fields may allow assigning to each point in space a unique combination of field values, provided the number of the crossing fields is not smaller than the dimensionality of the space.

For example, for mapping a three dimensional space, at least three crossing fields may be required, and more may be used. A larger number of crossing fields may provide information usable, for example, for noise reduction and/or improvement of robustness in comparison to robustness achievable with only three crossing fields. The voltage gradients of the crossed electromagnetic fields are used, in some embodiments, to define axes indicating spatial position as a function of measured voltage. Since the voltage gradients are ordinarily curved, and/or otherwise irregular, the conversion to axis-defined position generally relies on the use of some form of transformation. Optionally, the transformation is dynamic (e.g., changing as a function of contact quality, movement artifacts, and the like).

In some embodiments, the body cavity shape is reconstructed to obtain a representation of a void region limited in its extents by surrounding tissue (e.g., a heart chamber, vascular lumen, gastrointestinal space, and/or urinary tract lumen). Additionally or alternatively, properties of the surrounding tissue are also included in the reconstruction, for example by associating additional measurements to positions at boundaries of the body cavity shape. The additional measurements may be additional to the electromagnetic field measurements, for example, measurements of electrical activity. Properties can include measured states of tissue such as myocardial electrical activity, dielectric properties of tissue, nearby locations of hard, soft, and/or void-filled body structures, etc.

In some embodiments, reconstruction of a body cavity shape and/or navigation in a body cavity using the reconstruction may be obtained by calculating a transform function T(X) applicable to each measurement x in a set of measurements X to obtain Y; which may be, for example, a reconstruction of a body cavity (e.g., if reconstruction is sought) or a position within a reconstruction (e.g., if navigation is to be guided). Measurements X may comprise measurements taken from a plurality of different sensors (e.g. electrodes) mounted on a probe moved within the body cavity. A transform function transforming measurements in measurement space to locations in physical space may be referred to herein as a measurement-to-location transform or mapping. A transform function transforming V-cloud to R-cloud may be referred to herein as a measurement-to-location transform or mapping.

In some embodiments, a pre-acquired image and/or other data of the body cavity may be available, e.g., a CT image of the body cavity, and used for the reconstruction and/or navigation in the body cavity. For example, it may be used for simulating expected voltage gradients at different regions in the target, and this identification may be used as a constraint on the transform, e.g., that when a given voltage gradient (e.g., between two electrodes) is measured, a transform transforming it to a region where the same (or similar) gradient was simulated to exist will be preferred over transforms transforming it to other regions.

In some embodiments, methods described herein for reconstruction may be used to update a pre-acquired image of a body part (e.g., body cavity or other volume) (e.g., a pre acquired anatomical image, for example a CT image) to account for changes occurring in the body part from the time when the image was acquired. For example, after a CT image was obtained, the patient may be treated (e.g., by providing medicine or other procedures) which may change the body part (e.g., expand or contract—the heart, for example, can change average size as a function of heartbeat rate, instantaneous size as a function of heartbeat cycle, or for other reasons), such change may be calculated, e.g., based on a set of measurements of the changed body part. The calculated change may be applied to the pre-acquired anatomical image to reconstruct an updated anatomical image (e.g., by moving voxels representing tissue in the image) which may correspond to a current state of the body part. There may also be updating of a previous reconstruction carried out by a different intrabody probe mapping method, optionally the same mapping method.

In some embodiments, reconstructing a body cavity is based on intrabody measurements of a plurality of crossing electromagnetic fields established within the volume. The reconstruction may comprise: receiving measurements of the crossing electromagnetic fields carried out using sensor(s) carried on an intrabody probe, the measuring being carried out with the probe at multiple locations in the body cavity, to provide a set of measurement samples, each taken at a location; generating based on said measurement samples, a transformation that transforms measurement samples to geometric positions; wherein the generating is performed without use of a distance to a reference position outside of the body cavity; transforming, using the generated transformation, said set of measurement samples into a set of geometric positions; and reconstructing the shape of the body cavity from said set of geometric positions.

In some embodiments, reconstructing a body cavity is based on intrabody measurements of a plurality of crossing electromagnetic fields established within the volume. The reconstruction may comprise: receiving measurements of the crossing electromagnetic fields carried out using sensor(s) carried on an intrabody probe, the measuring being carried out with the probe at multiple locations in the body cavity, to provide a set of measurement samples, each taken at a location; generating based on said measurement samples, a transformation that transforms measurement samples to geometric positions; wherein the generating is performed without use of an orientation or direction to a reference position outside of said body cavity; transforming, using the generated transformation, said set of measurement samples into a set of geometric positions; and reconstructing the shape of the body cavity from said set of geometric positions.

In some embodiments, reconstructing a body cavity is based on intrabody measurements of a plurality of crossing electromagnetic fields established within the volume. The reconstruction may comprise: receiving measurements of the crossing electromagnetic fields carried out using sensor(s) carried on an intrabody probe, the measuring being carried out with the probe at multiple locations in the body cavity, to provide a set of measurement samples, each taken at a location; generating based on said measurement samples, a transformation that transforms measurement samples to geometric positions; wherein the generating uses only reference positions within the body cavity; transforming, using the generated transformation, said set of measurement samples into a set of geometric positions; and reconstructing the shape of the body cavity from said set of geometric positions.

In some embodiments, reconstructing a body cavity is based on intrabody measurements of a plurality of crossing electromagnetic fields established within the volume. The reconstruction may comprise: receiving measurements of the crossing electromagnetic fields carried out using sensor(s) carried on an intrabody probe, the measuring being carried out with the probe at multiple locations in the body cavity, to provide a set of measurement samples, each taken at a location; generating based on said measurement samples, a transformation that transforms measurement samples to geometric positions; wherein the generating is constrained using one or more constraints; transforming, using the generated transformation, said set of measurement samples into a set of geometric positions; and reconstructing the shape of the body cavity from said set of geometric positions.

In some embodiments, generating a 3D model a body cavity may comprise: receiving a V-cloud, generating based on the V-cloud, a transformation that transforms V-cloud to an R-cloud; wherein the generating is constrained using one or more constraints; transforming, using the generated transformation, said V-cloud into R-cloud; and generating a 3D model of the body cavity from said R-cloud.

In some embodiments, reconstruction of a body cavity shape, and/or navigation in a body cavity (which may be guided based on a reconstruction), optionally comprises imposing different constraints on how the reconstruction should be performed using the set of measurements. The constraints may include, for example, any suitable constraint described herein or combination of two or more thereof. One or more of the constraints described in relation to reconstruction of a body part may be used for navigation in a body part, e.g., navigation of a probe in the part during a diagnosis and/or treatment procedure.

Exemplary Local Spatial Position Constraints on Reconstruction

In some embodiments, reconstruction (and/or in particular transformation generation) of a body cavity shape and/or navigation in a body cavity may be obtained by first assuming local spatial position constraints which are consistent with the physical conditions applying to individual sets of measurements (like the known relative distance of measuring sensors at the time the measurements were taken). In some embodiments, this assumption is combined with use of a multidimensional scaling (MDS) algorithm. MDS algorithms refer to a class of algorithms wherein objects (in some embodiments, measurements of voltage) are placed in an N-dimensional space (e.g., as described herein, the three dimensional space of a body cavity) so that between-object distances are preserved as well as possible (given all other, potentially competing, constraints). In some embodiments, the geometrical configuration of sensors on an intrabody probe provides the between-object distances, allowing an MDS approach to be used for reconstruction of a body part. In some embodiments, the configuration is fixed (e.g., a rigid catheter section). In other embodiments, the configuration may be flexible (e.g., a flexible probe section or multiple probes), however, there may still be useful constraints on the relative positions of probe sections, such as possible distances between sensors due to probe flexibility and deformability limitations and/or other properties. In addition, estimations of geometrical properties of the probe (or probes) and interrelations between sensors carried thereon may be used, for example, probe position values and/or sensor position values provided by position sensors and/or restrictions on movement provided by nearby structure and/or based on possible speed of movement of parts of the probe. It is noted that many of these constraints are local (e.g., relate to volumes with a diameter of less than 50%, 20%, 10% or intermediate percentages of a largest dimension of the reconstructed shape). In some embodiments, more global constraints are used, for example, on an overall shape of the transformation, on a uniformity of the transformation (e.g., as compared to a generic transformation based on generally expected behavior of electric fields in the body) and/or based on expected distances between closest simultaneous measurements.

In some embodiments of the invention, several sets of measurements x are obtained in X; each set x being made up of a plurality of measurements $x_i$, $x_j$, ... measured simultaneously by different sensors i,j on a same probe; and with distances (e.g., or other geometrical constraints) between at least some of the sensors being known or estimated (e.g., including bounded), so that the distances can be used as a constraint. Moreover, in some embodiments, more than one measurement is made from each sensor (e.g., measurements of different electrical fields, e.g., of fields having different frequencies), so that the set of measurements in total includes, e.g., $x_{i_{1,2}}$, ..., $x_{j_{1,2}}$ ..., ..... It is noted that these constraints may be recalculated as part of the reconstruction.

Measurements in a set are optionally taken substantially simultaneously, i.e., while the probe remains in substantially the same position. Moreover, in some embodiments, the different measurement locations on the probe optionally have known spatial relationships to one another, which comprise, in some embodiments, local spatial position constraints. Reconstruction of the body cavity shape may be guided based on these known spatial relationships; for example, in some embodiments, a transform function T(x) on a each member of group of measurements X comprising the set of measurements x may be calculated such that $|T(X_i)-T(X_j)| \approx d_{ij}$; $d_{ij}$ being the distance between electrode, and electrode 3.

For example, in some embodiments, the electrodes are each at a known distance and/or angle from one another due to a fixed geometry of the intrabody probe to which they are mounted. Alternatively, in some embodiments, electrodes are in variable relative positions, and the variation accounted for based on information such as parameters of deployment (e.g., how expanded a basket-shaped intrabody probe is at a moment of measurement), and/or on further measurements (for example, of force as an indication of probe deformation, inter-electrode conductance as an indication of inter-electrode distance, etc.). Optionally, additional constraints on the relative orientation of the measurement locations are also used. Such constraints are optionally known, for example, from geometrical/anatomical constraints on the procedure itself.

Optionally, measurements in each set are substantially simultaneous. Herein, "substantially simultaneous" should be understood to mean that the measurements of each set may be obtained:
actually simultaneously (i.e., with partially or wholly overlapping measurement periods),
close enough in time that motions of the intrabody probe during acquisition of the set can be neglected, and/or
close enough in time that skew due to small movements during sampling of a set of measurements can be dependably factored out and/or adjusted for if necessary (e.g., by use of time-weighted averaging of time-adjacent samples).

Optionally, a collection of measurements is considered as a set of measurements mutually constrained in relative position (e.g., fixed at particular relative distances and/or relative angles, at variable but known distances or angles, for example by use of an encoder, etc.), without a requirement for substantial simultaneity of measurement. For example, multiple measurements at multiple times from an intrabody probe are optionally taken while a portion of the intrabody probe remains anchored at one or more regions. Relative movements of other intrabody probe portions, assuming they are known (by use of a movement encoder, for example) can then be applied to determine a relative position constraint. These measurements are optionally related to one another through use of the fixed anchor and the known bending parameters to provide calibration. It can be understood from this, and it should be understood to apply generally, that a measurement (also known as a "measurement sample") optionally is treated as a member of a plurality of "sets" of measurements, where members of each set may be related to one another through application of different mutual position constraints.

For simplicity, and for purposes of description herein, sets of simultaneous measurements from corresponding electrodes of a fixed-shape probe are often used in examples. However, it should be understood that other configurations of sensors, and/or other methods of obtaining a spatially calibrated "ruler" to constrain distances between them are optionally used in some embodiments of the present invention. In some embodiments, the constrained distances may be used to ensure that the target shape is reconstructed so that the distance between the electrodes (e.g., in mm) is kept approximately the same all around the reconstructed shape, even if the difference between their readings (e.g., in mV) changes substantially from one place to another. For example, in some embodiments, the length of the catheter is reconstructed to be the same within ±15% even though the voltage gradient between the same electrodes changes by a factor of 10 or more.

Herein, voltages measured substantially simultaneously by two electrodes separated from each other by a fixed distance (e.g., because they are fixed to a rigid probe portion), may be referred to as sister measurements; the locations assigned to such measurements may be referred to as sister locations; and the distances between sister locations may be referred to as sister distances. The fixed distance itself may be referred to as a desired sister distance.

In some embodiments, a transform function to be found is defined as comprising two terms: one which gives a roughly scaled transformation of V-cloud measurements into an R-cloud, and a second which applies displacements to that roughly scaled R-cloud. The second term potentially helps overcome at least some of the electrical field non-linearities and/or non-orthogonality which may exist in the roughly-scaled transformation.

The rough-scaling term of the displacement approach of some embodiments of the invention can be understood, for example, by envisaging each measurement set x of the measurements X to be first "copied" from a coordinate system in a measurement space, wherein each of the measurement space axes is, e.g., an axis of measurement values for one of a respective plurality of crossing electrical fields; to a coordinate system in a physical space, wherein different positions along the axes represent different locations in physical space. This copying may be carried out with a different scale along each axis; for example: a voltage difference of 1 mV measured along a horizontal axis in the measurement space may correspond to a distance of 3 mm along the horizontal axis of the physical space, and a voltage of 1 mV measured along a vertical axis in the measurement space, may correspond to a distance of 2 mm in the physical space. In notation form, the voltage points X may be envisaged to be first "copied" to initial location points Y, e.g., by a scaling transformation Y=diag(a)X, where a is, in some embodiments, a vector comprising scaling coefficients a=($a_x$,$a_y$,$a_z$), with units of distance/measurement (e.g., mm/mV). diag(a) indicates the matrix diagonalizing vector a. With the addition of a displacement term W, the initial location points diag(a)X are displaced by displacement W to have the proper local scaling (i.e., to make sister distances in Y optimally correspond to the known distances between the sensors). It is noted that while the axes in the physical space may be orthogonal, this does not limit the method to embodiments where the fields themselves are orthogonal to each other, or even close to orthogonality (e.g., the axes may be, for example, 20 degrees or more off axis, for example).

The axes in the physical space are provided as a convenient means for describing locations in space, and the transformation from the measurements to the positions by the rough-scaling term is arbitrary. Still, the more orthogonal are the fields, the less arbitrary is this transformation, and the computational effort required to find the optimal transformation may be smaller. In some embodiments of the invention, the rough-scaling term is mainly used for transforming the data from units of voltage (or other measurement) to units of length. In addition, if the data implies a need to stretch the reconstruction along some direction, the rough-scaling term can allow doing so using a smaller number of actions than would be required if only W was available for applying such stretching (e.g., in case the rough-scaling term was predetermined to be the same for all the fields.

The displacement term W can be decomposed in different ways in order to guide the search for the individual displacements that make it up. In some embodiments, accordingly, the displacement W is expressed as a multiplication of two matrices: W=UW', with U being a representation of X in a coordinate system "natural" to X, and W' being a matrix of coefficients (displacement coefficients) which give the magnitude of displacements applied within the same "natural" coordinate system, also referred to herein as a coordinate system that preserves the "intrinsic geometry" of X.

This intrinsic geometry, in some embodiments, is defined as comprising a set of linearly independent features (referred to as characteristic vectors or eigenvectors v of a similarity matrix, reflecting similarity between sampled measurements) which "sum up" (after individual scaling of the eigenvectors v, each by its eigenvalue) to produce an equivalent representation of X.

Decomposition of X into eigenvectors, in some embodiments, has the effect of separating features according to their spatial frequencies. This property is optionally be used in relation to maintaining spatial coherence, for example as discussed hereinbelow.

In some embodiments, a kernel K is defined as a matrix that expresses a measure of the distances between each pair of measurements:

$$K_{i,j} = K(x_i, x_j) = e^{\frac{-\|x_i - x_j\|^2}{2\sigma^2}}$$

This form of a kernel is optionally referred to as a radial basis function kernel, and is an example of a similarity matrix. The sigma parameter is a free variable, which optionally is set to be about 0.1. Optionally, the kernel K is normalized to a normalized kernel $\tilde{K}$, for example by one of:

$$S = \text{diag}\sum_j K_{i,j} \quad \tilde{K} = \frac{K}{S}$$

or $$S_i = \text{diag}\sum_j K_{i,j} \quad S_j = \text{diag}\sum_i K_{i,j} \quad \tilde{K} = \frac{K}{\sqrt{S_i S_j}}$$

or $$S = \text{diag}(K \cdot 1n) \quad \tilde{K} = S^{1/2} K S^{-1/2} \text{ wherein } 1n = \begin{bmatrix} 1 \\ 1 \\ \ldots \\ 1 \end{bmatrix}$$

The normalized kernel $\tilde{K}$ is decomposed to find U, for example, using the Graph Laplacian, such that for the k most significant eigenvectors u:

The eigenvector matrix U is: U=[$u_1$, ... $u_k$]
The eigenvalue matrix V is: V=diag([$\lambda_1$, ... $\lambda_k$])
And the decomposition satisfies: $\tilde{K}u = \lambda u$ Putting the terms just described together results in an X (measurement) to Y (position) transformation which may be expressed by the equation Y=diag(a)X+UW'.

Each set of a and W' provides a configuration that gives a generally different transformation of X to Y. To find the transformation that provides a best fit between sister distances and the desired sister distances (e.g., known distances between the sensors on the probe), a penalty may be associated with each deviation of the sister distances from the known distances, and this penalty minimized by known minimization procedures. Other penalties described herein are also optionally applied, e.g., by addition to the penalty on the difference between sister locations and known distances between sensors on the probe. A choice of a and W' with a minimal penalty result gives, from the point of view of the algorithm and its particular cost function, the "correct" Y from the given X.

Coherence Constraints on Reconstruction

In some embodiments, reconstruction of a body cavity shape and/or navigation in a body cavity using such a reconstruction may be obtained by imposing coherence constraints, e.g., a coherence model, on a transformation, a set of measurements and/or a set of geometrical positions after transformation.

In some embodiments of the invention, the coherence constraints are added to constraints on relative positions assigned to sensors (e.g., to the above-mentioned constraints of having sister distances similar to desired sister distances). An example for a coherence constraint may be that two measurements made at nearby regions in space are assumed to produce measurement values which are also "nearby" in the measurement space under some metric (e.g., change in voltage of a certain number, for example, 5, 3, 2 of the crossing fields is less than, for example, 30%, 20%, 10% or intermediate percentages). Similarly, the transformation of measurements to locations may be constrained so that every two measurements of "nearby" values are transformed to locations close to each other, under some metric. In some embodiments of the invention, "nearby" is defined as a function of the range of the reconstructed volume, for example, a distance of less than 30%, 20%, 10%, 5% or intermediate percentages of a maximum dimension of the reconstructed volume. Optionally or additionally, "nearby" is defined as a function of time (e.g., how long would it take or did it take a probe to move between positions, for example, 30 ms, 20 ms, 10 ms, 1 ms or smaller or intermediate times. Optionally or additionally, nearby is defined as function of the probe geometry, for example, less than 10×, 5×, 2× or intermediate multiples of a smallest or largest distance between electrodes on a catheter.

It is noted that a same constraint (e.g., coherence or known distance deviation) may be considered as a single constraint (e.g., applies to all the data) or as a plurality of separate constraints (e.g., applies separately to each data point or pairs thereof. In some embodiments, processing is simplified by aggregating constraints so that they are treated as one for optimization purposes. For example, a distance constraint may be defined as a single constraint on all distances and electrode pairs, which may be relaxed or enforced as a single constraint.

A coherence criterion may be set to require that the transformation transforming measurements to locations would be smooth, that is, that small differences in measurements in one place in the measurement space will not result in much larger difference in locations than in a neighboring place. Since sensors on the probe are at neighboring places, such a constraint may be applied on sister distances, that is, that sister distances don't change abruptly from one place of the probe to another. This may be achieved, for example, by using a cost function penalizing transformation making use of high frequency components, and the overall penalty (also referred to herein as "cost") may be minimized (by reducing the contribution of high frequency components to the transformation) in order to find a coherent transformation. It is noted that even if a transformation is smooth, it may be vary, for example, by a factor of 2, 3, 4 or more in one or more dimensions, at measurement locations that are not adjacent (e.g., >10% of volume diameter away).

For example, a coherence criterion may be set by setting a penalty to each of the k eigenvector components of matrix U, and this penalty may be higher as the frequency of the component is higher, and increase as the displacements along this component are larger. This way, distributions that result from transformations that include only displacements along low frequency components would nearly not be penalized, and those that result from transformations that include displacements along components of very high frequencies will be penalized heavily. A minimization procedure may be applied to minimize the penalty, to find a transformation that results in sister distances that change smoothly (e.g., transformations with displacements mainly along small frequency components), which is an example of a coherence criterion. Additionally, a coherence criterion is optionally influenced by the direction of the voltage gradient (i.e., a smaller change in gradient direction is "more coherent"), and/or by the rate of change in the gradient itself (and/or its direction) and/or any higher order gradient derivative.

Additionally or alternatively, in some embodiments, coherence of a transformation result is enhanced by how many eigenvectors are used (the value of k). In some embodiments, k is around 50-250; optionally or alternatively, k is a value around 20-25% of the total number of measurement vectors x in X. For example, if only the k lowest-frequency components are used, the larger is k, the less coherent, potentially, is the transformation. However, larger k (that is, allowing transformations along more components of U) results in larger flexibility and better chance to minimize other terms in the cost function (e.g., the requirement for sister distances that are similar to the desired sister distances).

A metric by which distances are measured for defining coherence and/or sister distances, can be, for example, the Euclidean distance. In some embodiments, the metric may be a "natural" distance, for example, an Euclidian distance defined in the natural geometry of the measurements cloud, that is, over the components of the U matrix. In some embodiments, the metric may be a distance in a measurement-defined vector space (i.e., a vector space comprising a plurality of different measured parameters as vector components), but may also be more involved than that.

Optionally, the coherence constraint can be expressed as $\Delta X_{ij} \propto \Delta Y_{ij}$ where $\Delta X_{ij}$ is a change between two locations i,j of measured values in X (for example, changed measurements of voltage with respect to a plurality of crossed voltage gradient-defined axes), and $\Delta Y_{ij}$ is a change in the spatial position (e.g., distance, under a suitable metric) between the two locations i,j, within the body cavity to be reconstructed, Y.

The proportionality sign $\propto$ should be understood to refer to any suitable coherence metric and/or algorithm (coherence model), not necessarily constant uniform proportionality. For example, a proportionality parameter is optionally allowed to vary (e.g., with a factor of at least 2, 3, 4 or intermediate or greater values) over the domain of measurement values. In some embodiments, the coherence model allows the proportionality parameter to vary smoothly, and/or according to a model of expected behavior, e.g., varying smoothly everywhere except near the edges or other particular zones of the mapped space.

As mentioned, in either physical space or measurement space, distances are not necessarily direct Euclidean distances. In some embodiments, for example, the measurements may form a measurement cloud (in some measurement vector space, for example), and the spatial positions to which the measurements are transformed may form a position cloud. In some embodiments, a natural distance between two measurements may be defined as the length of the shortest path that goes between the two measurements only through the measurement cloud. A path going only through a cloud is referred to herein as an intra-cloud path. Similarly, a natural distance between two spatial positions may be defined as the length of the shortest path that goes between the two spatial positions only through the position cloud (that is, the shortest intra-cloud path in space). In some embodiments, the measurement cloud may be segmented, in the sense that it includes distinct segments; for example, a central segment connected to each of a plurality of peripheral segments.

The peripheral segments may be interconnected only by pathways passing into the central segment from one segment, and back out of it to the other. In such embodiments, two peripheral segments may have points (e.g., measurements) that are nearby in the Euclidean sense, but the natural distance between them is long, as every intra-cloud path between them goes via the central segment. In such embodiments, measuring coherence using natural distances may preserve the segmentation of the measurement cloud, so that the position cloud remains similarly segmented. That is, a transform requiring coherence in terms of natural distances may transform a segmented measurement cloud into similarly segmented spatial positions cloud. Such a transform (whether based on intra-cloud coherence or preserving the segmentation by different means) may be referred to herein as a segmentation preserving transform. A segmentation preserving transform is potentially suitable to preserving features of heart chambers; for example, for preserving the pulmonary veins connected to the left atrium and separated from each other.

An example of a segmentation preserving method of transforming a segmented measurement cloud into a similarly segmented position cloud may include assigning each measurement to a segment in the measurement cloud; and transforming each measurement to a position in a segmented spatial position cloud requiring that measurements assigned to a same segment in the measurement cloud are transformed to a same segment in spatial position cloud and measurements assigned to different segments in the measurement cloud are transformed to different segments in the spatial position cloud. Such segmentation preserving method may replace a Euclidean-distance based coherence condition, or be used in addition. For example, in some embodiments, the coherence may be primarily based on Euclidean distances, with segment preservation used to protect against segments coalescing, e.g., by disallowing influence on the coherence model by differences between points whose Euclidean distance is sufficiently shorter than their natural distance.

Combination of Local Scaling and Other Constraints

In some embodiments, the approaches of local spatial constraint (e.g., on sister distances) and a coherence-related constraint are used in a combined method of transformation (e.g., generating a transformation meeting these constraints). Outputs of each are optionally reconciled by use of an error (equivalently referred to as cost, penalty or "energy") reducing weighting scheme, for example as now described.

Initially, in some embodiments, the detailed, or optionally even the overall geometry defined by a "true" body cavity shape Y is unknown, but still, a useful approximation may be obtained by a transformation that transforms the measurements according to the applied constraints. The target for "usefulness" of the approximation is optionally dependent on the particulars of the procedure, and even of particular tasks within the procedure; and there can be a plurality of criteria for evaluating the accuracy of reconstruction, optionally applied simultaneously (e.g., as concurrent penalty weightings), and/or separately (e.g., to obtain reconstructions optimized for different sets of penalty weights). In some embodiments, for example, the target for "useful approximation" is to be able to place adjacent small lesions next to each other within some relative margin of error as part of an ablation procedure; for example, an error within 0.5 mm, 1 mm, 2 mm, 4 mm, 8 mm, or some other intermediate margin of error. Additionally or alternatively, another target for useful approximation is positioning a linked chain (or other grouping) of small lesions within some margin of error relative to landmarks of a target tissue; for example, an error within 1 mm, 2 mm, 4 mm, 8 mm, or another intermediate margin of error.

In some embodiments, the measurements are known to be obtained by sensors fixed at known distances from one another, e.g., because they were obtained from a plurality of different sensors positioned at fixed distances on an intrabody probe. However, the known relative position constraint is not limited to the use of sensors arranged in a linear, ruler-like configuration. For example, in some embodiments, the sensors are arranged in pairs, where each two electrodes in a pair are so close that the catheter cannot practically fold between them, but the inter-pair distances are large enough so that the catheter may fold between pairs. In such an embodiment, intra-pair distances may be known, and inter-pair distances may be unknown. It has been found that the intra-pair distances may be sufficient for obtaining useful approximations. The cost function optionally comprises another constraint based on distance and/or relative angle of measurements. Expressed in notation, for example, the measurements are position-constrained such that a transform yielding distance $|T(X_i)-T(X_j)|=\Delta Y'_{ij}$ can be found, with a result that is potentially a good approximation of the actual distance. Optionally, the transform is found by a process of "energy" or error/penalty reduction as just outlined.

Considering local spatial calibration (e.g., MDS-used, and/or sister distances-based) constraints alone, the relative positions of each separate set of measurements (e.g., a set of measurements taken at different times and/or at different locations in the target) are unlinked. The measurements themselves are subject to measurement noise. Therefore, there may remain uncertainty about how different measurement sets should be related to one another in space.

In some embodiments, this problem is alleviated at least in part by incorporating into a reconstruction algorithm assumptions about coherence between distances in the measurement space and distances in the physical space. Optionally, coherence and local spatial calibration constraints are weighted relative to each other to achieve reduced transformation error and/or reconstruction (in general) error.

Conceptually, the weighting can be thought of as allowing mutual position constraints to act as a ruler, measuring differences between positions in units of distances between electrodes, and influencing and/or partially overriding the local conditions of coherence. Conversely, the constraint of coherence may help to assign different sets of measurements to positions in space, while mitigating distorting effects of measurement noise. As more measurements are made, the limits of the body cavity in which the probe is moving will limit the extent of movements, so that the reconstruction Y' potentially grows to more closely resemble the actual shape of the cavity Y (herein, the notation Y' may be used to designate a reconstruction in contexts where its distinctiveness from the actual cavity shape is being emphasized).

In some embodiments, for example, the transform T is defined as a transform that minimizes a suitably weighted joint error in satisfying both the coherence condition and local spatial constraints. For example, error with respect to local spatial constraints is optionally found from $|T(X_i)-T(X_j)|=\Delta Y'_{ij} \approx \Delta Y_{ij}$, where the error is in the deviation of distances in Y' from known real-world distances in Y (e.g., error is $|Y'-Y|$, or another suitable error metric). Similarly, error with respect to coherence is optionally found from $\Delta X \propto \Delta Y'' \approx \Delta Y'$, where the error is in the differences in Y' from the coherence-modeled output Y'' (e.g., error is $|Y'-Y''|$, or another suitable error metric). Minimization of error is by any suitable technique, for example, statistical analysis and/or gradient descent. The symbol $\approx$ is used herein to show that discrepancies between the terms on its both sides (in this case, between T(x) and Y), are minimized by use of a suitable reconstruction procedure, although equality cannot be guaranteed.

In some embodiments, a reconstruction of Y is produced exclusively or almost exclusively based on sensor measurements, their known distances, and optionally an assumed coherence model.

In some embodiments, a reconstruction of Y is produced exclusively or almost exclusively based on imposing local spatial position constraints and optionally coherence constraints on a set of measurements.

In some embodiments, a coherent transformation may be obtained by a method using spectrum decomposition, for example, by a diffusion map algorithm. In some embodiments, such a transformation may be segmentation preserving. For example, embodiments are described herein using the concept of displacement optionally are modified to preserve coherence by the selection and/or weighting of components, along which the displacements occur, according to their spatial spectrum frequency.

Each constraint may be embodied by applying a penalty to a transform insofar as the transform violates the constraint. For example, the constraint to have the sister distances as accurate to their known distance as possible may be embodied in a "penalty" applied to transformations that generate sister distances that deviate from the known "ruler" length: the larger the deviation—the larger the penalty. Thus, adjusting the transform to reduce the penalty applies a criterion for reducing the variability in the sister distances. In some embodiments, reducing variability in sister distances reduces differences between sister distances and the desired sister distances. In some embodiments, a cost function penalty that encourages having the sister distance as similar as possible to the known distance will be in addition to a cost function penalty that encourages the sister distance to be kept as constant as possible across the transformation. In some embodiments, a cost function penalty that encourages minimizing differences between sister distances and the desired sister distances may result in reduced variability of the sister distances without posing an explicit constraint on the variability.

A coherence constraint may be, for example, that W is smooth; for example smooth in the sense that if it is represented as a combination of displacements along linearly independent spatial components of different spatial frequencies, it includes only or primarily displacements along components of low spatial frequencies.

Eigenvectors of high frequency are typically more influenced by noise in the measurement cloud, than by major structural characteristics of the cloud. Thus, taking into account only the eigenvectors associated with the lowest frequencies allows grasping the major structure of the cloud while cleaning part of the noise, and ensures, for example, that the displacement UW' would be of at least some smoothness.

Furthermore, reducing the contribution of eigenvectors of the highest frequencies reduces the dimensionality of the problem, as the potential displacement W' is limited to displacements along the low frequency eigenvectors (and linear combinations thereof). This may be thought of as defining in the cloud some sub-clouds (which may also be referred to as segments) that together reproduce the major structural characteristics of the cloud, and limit the displacements to be within these sub-clouds. Therefore, this method may be considered segmentation preserving.

The constraint to have the displacement change smoothly, and in a coherent manner, may be achieved by applying a "penalty" to the various components of the displacement: the higher the spatial frequency of a component, the larger is the penalty to its contribution. Once a displacement W that minimizes the overall penalty (e.g., a sum, optionally a weighted sum, of the penalty for sister distance variability and the penalty for high spatial frequencies) is obtained, it may be used to displace the initial locations to their new locations, which represent a location cloud that may be used for reconstruction of the body-part. Going from a location cloud (e.g., a set of geometric positions) to a reconstruction (i.e., a model where the points in the location cloud are interconnected to form a mesh that defines outer borders to the cloud) are known in the art and are not generally a subject of the present disclosure. An example method may be found, for example, at Bernardini, Fausto, Joshua Mittleman, Holly E. Rushmeier, Claudio T. Silva and Gabriel Taubin. "The ball-pivoting algorithm for surface reconstruction." *IEEE Transactions on Visualization and Computer Graphics* 5 (1999): 349-359, the disclosure of which is incorporated herein by reference. Therefore, the terms location cloud (or R cloud) and reconstruction are used herein interchangeably. Finding W that minimizes the penalty may be carried out using standard minimization procedures.

In some embodiments, the coherence criterion is implied using the intrinsic geometry of the V-cloud, and need not be specified as a separate mechanism in the operation of the algorithm. This may be achieved, for example, by defining the smoothness criterion (which gets a larger penalty the larger it is) as $W^TVW$, where V is a diagonal matrix of the eigenvalues that correspond to the eigenvectors making up U.

Optionally, a few further conditions are set to guide the reconstruction process—for example, broad assumptions about the orientation and voltage ranges of electromagnetic fields being measured, positions of landmarks, and/or global constraints on positions and/or orientations which the intrabody probe can physically reach based on its size, flexibility, entry point to a chamber, etc. In some embodiments detailed initial conditions are set for the reconstruction. In some embodiments of the invention, such initial conditions do not include a reference point or frame which is used to define the positions of measurements relative to the point, before transformation and/or not used as part of the transformation.

Additional Constraints on Reconstruction

An aspect of some embodiments of the present invention relates to the use of additional constraints to create a body cavity reconstruction and/or more specifically a transformation, based on constraints of coherence and local spatial position, e.g., the geometrical configuration of sensors on an intrabody probe. Optionally, the additional constraints are based on additional information to that used to shape or constrain the reconstruction just described.

Anatomical Data

In some embodiments, the additional information comprises known anatomical data. Optionally, the anatomical data is fairly detailed and particular to the patient. For example, the anatomical data may be obtained directly from the patient, such as from segmentations of MRI or CT data, and/or from a reconstruction using other data, for example, a previous reconstruction created based on mapping of electrical measurements (e.g., for updating a previous reconstruction and/or transformation as opposed to building a new transformation and/or for modifying/updating a previous transformation using old measurement samples and new measurement samples, with the previous transformation optionally a starting point in the search space). Optionally, the anatomical data are less particularly matched to the patient, e.g., obtained from atlas data (e.g., matched to patient age, gender, weight, etc.). Optionally, the anatomical data is partial; for example, comprising specifications of relative distances between anatomical landmarks to which a reconstruction is scaled. For example, the reconstruction may be constrained so that separately known distances between anatomical landmarks, known independently of the measurements, are consistent with distances assigned between V-cloud measurements taken at the anatomical landmarks, and the known distances between the sensors. Moreover, the separately known distances between the landmark positions, combined with measurements taken by sensors at the anatomical landmarks. may provide data on the measurement gradient (e.g., in mV/mm) at the landmarks. Measurement differences between the landmarks (e.g., in mV) may then be divided by the gradient to obtain a physical distance between the landmarks (e.g., in mm). In some embodiments, such physical distance is constrained to be in accord with the additional information available for the reconstruction process. In some cases, anatomical information includes restricting measurements to be along a line or within a defined space, based on anatomical limitations and/or expected interaction of probe manipulation and the anatomy. For example, retracting a catheter may be expected to define a line along a wall of the heart, and all measurements may be constrained to lie alone a line (e.g., with some restricted width and/or curvature), in the reconstruction space.

Such additional information can be obtained from CT data, MRI data, atlas data, previous reconstructions, or any other suitable source. In some embodiments, the anatomical data, e.g., an anatomical image or data of a body cavity, may be used for imposing similarity constraints on the reconstruction, e.g., such that the reconstructed body part may be similar to what is expected from the anatomical data Y, for example: transform T(x) may be calculated such that T(X)≈Y, where Y is based on the anatomical data.

Optionally, this transformation is used as an initial state at the beginning of a procedure, and replaced and/or refined as more position data become available.

In some embodiments, landmarks are identified by constraints on movement of the probe itself. For example, a wall of a cavity may be identified at a region never crossed by the probe. In some embodiments, landmarks are identified based on characteristic dielectric and/or electrical conduction properties in the vicinity of the landmark.

In some embodiments, maps of how the measurement values are expected to distribute in space (at least approximately) are used as constraints. For use in navigation, this can be based, for example, on simulations of electromagnetic field voltages in space, based on considerations of electrode configurations and/or body tissue dielectric properties.

In some embodiments of the invention, position sensing by other means, such as optical, ultrasonic, magnetic or electromagnetic field based methods is used as constraints on the reconstruction. For example, two points indicated by a position sensor to be within a distance of, for example, 1 mm, are constrained to remain at that distance. Optionally, such constraint is flexible and may be modified to obtain a better transformation. Such position data, if available, may also be used for reconstructing the cavity from the R-cloud, generating scaling and/or generating orientation information. In another example, imaging data, such as x-ray data or from an intrabody or external ultrasound imager are used to provide constraints.

In some embodiments of the invention, anatomical constraints are used as constraints on the sensed fields. For example, a tissue location is used as a constraint by defining how it may affect the shape of the electric fields (e.g., as evidenced by the transformation at that location). As can be appreciated, like with other constraints, the transformation generation process may cause a tissue location and/or tissue properties to change.

It is noted that in some embodiments the initial set of samples may be deformed due to existence of field deformation caused by surrounding tissue (e.g., as noted in the above "FIELD GRADIENT-BASED REMOTE IMAGING" application. Optionally, measurement points which show such deformation (e.g., or assumed to have such, based on a low density of measurements in their local), are preserved together with the deformation, which may indicate the shape of remotely (e.g., non-contacted) located tissue. Optionally, such shape indicated by such points is used as a constraint on transformation and/or for determining the reconstructed volume (e.g., as indicating points near the surface Auxiliary Fields An aspect of some embodiments of the present invention relates to the use of auxiliary fields to reconstruct a body cavity based on the constraints of coherence and the geometrical configuration of sensors on an intrabody probe.

In some embodiments of the invention, three electromagnetic fields may be sufficient for the reconstruction, but more may be used. The three electromagnetic fields may be generated by (transmitted from) body surface electrodes configured to establish three crossed, time-varying electrical fields, such that there is some significant component of voltage change in each cardinal direction (X, Y, and Z). Where separate pairs of opposed body surface electrodes are used for each axis (e.g., members of each pair connected in a common circuit, this optionally comprises a six-electrode configuration. In some embodiments of the invention, electromagnetic fields are also generated (transmitted) between non-opposed body surface electrodes, in any suitable combination (pairwise, and/or between groups of electrodes). In some embodiments, supplementary electromagnetic fields generated between body surface electrodes in addition to the first three, are also used for the reconstruction. These "supplementary" fields are not necessarily optimal for primary use in intrabody probe navigation; for example, because their gradients are not very linear in a region of interest, and/or because they are not oriented to provide steep gradients in the region of interest. However, taken as a set of supplementary fields, they provide a source of spatially-ordered sensing data which is used, in some embodiments of the invention, to help in constraining the reconstruction and/or improving accuracy.

In some embodiments of the invention when more than three fields are used, a method of dimension reduction may be applied on the measured data. For example, a set of measurements of 10 fields at a location may be reduced in dimension into three or four dimensions. Methods of dimension reduction known in the art may be used. In some embodiments of the invention, the dimension reconstruction uses machine learning techniques to determine which of several possible reductions provide a best solution. This may be performed for a set of patients. Alternatively or additionally, dimensional reduction may be practiced per patient, for example, as an example of a constraint applied to the transform, the constraint being—weights on the various fields and/or indications which field values to combine, with changes in weights indicating which fields and/or combinations thereof take part in the transformations.

Alternatively or additionally, the three (or other number) best fields may be selected for use. Optionally, the selection of which fields to use may vary over the reconstruction volume. Optionally, there is an overlap in fields used at adjacent locations, so as to assist in ensuring coherence between transform functions in two locations in the reconstruction volume.

Periodically Varying Data

An aspect of some embodiments of the present disclosure relates to the use of periodically-varying data to constrain a transformation of measurements into a reconstruction of a body cavity.

In some embodiments, measurements in X potentially fail to be uniquely mappable to positions in a body cavity reconstruction Y' due to changes in tissue structure over time. For example, the shape of the heart, as well as shapes of various chambers of the heart, are changed during respiration, and, naturally, also during a heartbeat. For example, human heart typically beats between 1 and 2 times a second, and if data is collected at a rate of 100 times per second, data are collected from about 50 to 100 different phases of the heart. Collecting data when the body cavity is at different shapes might affect the reconstruction undesirably. For example, the variation of heart shape during a heartbeat might cause a small location inside the heart to be smeared over a larger portion of the reconstruction. In some embodiments, periodically varying data indicative of the periodical variation in the body cavity shape are collected at the same time the crossed electromagnetic fields are measured. This data may contain, for example, heartbeat rate, ECG signals, etc. In some embodiments, this periodically-varying data is used to reduce the effect of the periodic change in the body cavity shape on the reconstruction of the body cavity.

For example, movements of tissue due to respiration and/or heartbeat can change the shape of the voltage distribution of electromagnetic fields in a heart chamber, so that a probe which is fixed in position still measures phasic voltage changes. In some embodiments of the present disclosure, a transform from measurement space to physical space is defined to be dependent not only on the measurements of the electromagnetic fields X, but also on one or more periodically varying variables, also referred to herein as phasic variables. For example, T optionally depends on the state of phasic variables $\theta$ for respiration phase, and/or $\varphi$ for heartbeat phase to yield $T(X,\varphi,\theta)=Y'$. Optionally the transform result Y' is phase-stabilized so that it approximates a static cavity shape Y (e.g., a "snapshot" of a heart cavity at some particular phase of the heartbeat cycle and/or the respiratory cycle). Optionally, Y' is dynamic, approximating a phase-dynamic cavity shape $Y(\varphi,\theta)$. Optionally, there is a combination of phase-stabilization and phase-dynamism; for example, stabilization/dynamism with respect to selected reconstructed areas and/or with respect to particular time-dependent processes.

In some embodiments of the invention, data allowing phase-independent identification of reconstruction regions is obtained by pressing an intrabody probe against a moving tissue region to essentially immobilize the tissue relative to the probe. Measurements measured under this condition, referred to herein as "static measurements", may change over time mainly as a function of the phasic changes. Minimizing the effect of periodic changes in the body cavity shape on the transform may "clean" the transform from the effect of the periodic changes, and bring about a static reconstruction that is less smeared than would be obtained without such minimization.

In some embodiments, a transform may be generated under a constraint that a measurement cloud collected when the probe was immobilized in relation to the tissue, would be transformed to a location cloud of minimal radius in the physical space, thus minimizing the effect of the periodic tissue change on the transform. More generally, the transform may be constrained to minimize the volume in physical space to which static measurements are transformed. In some embodiments, such a transform is used to transform measurements taken when the probe is not immobilized, so as to minimize the effect of the periodic shape change on the obtained reconstruction. In some embodiments, the physician controlling the probe may indicate time periods when he believes the probe is immobilized in relation to the tissue, and only data collected during these time periods are used for generating the transform, which is afterwards used to transform data collected at all times.

In some embodiments, phasic motion is taken into account, by allowing a same voltage measurement to be associated with different locations, depending on the phase (e.g. of respiration and/or heart-beat) at which the measurement was made. This may be accomplished by using time varying data indicative of the phase of the body cavity as input, so that the input has more than 3 dimensions, for example, three voltages of the crossing electromagnetic fields, one respiratory phase, and one heart-beat phase. In such an example, the distance between measurements (e.g., as appears in the above-mentioned kernel) is defined in a 5-dimensional space (e.g., or a 2D array of 3D spaces). In some embodiments, such a definition of the kernel allows transforming differently data collected at different phases, and providing a reconstruction where the effect of the phasic motion is minimized.

It should be noted that the fixed-position technique also potentially makes measurements at both a contacting electrode (in direct contact with tissue), and at non-contacting electrodes (spaced from the tissue). Fully out-of-contact measurement sets can potentially be incorporated into the reconstruction based on similarities to measurements made while contact was at a fixed tissue region of reference, potentially helping to propagate phase-influenced information into regions more distant from body cavity walls at which the fixed-position technique can be applied. In particular, phase-influenced measurements during free movements of a probe potentially mix movement of the probe itself (e.g., due to being jostled at an anchoring position), with changes to the environment. Some degree of statistical separation between movement of the probe and of movement of nearby tissue is optionally obtained by comparing immobilized and non-immobilized measurement readings from nearby positions.

In some embodiments, non-repeating time-dependent changes in tissue state are accounted for by a transform. For example, there may be changes to the voltage gradient of an electromagnetic field due to changes in overall tissue thickness and/or chamber size during a procedure. This can be due, for example, to changes in patient hydration, and/or to changes in edema state of tissue surrounding the body cavity (e.g., triggered by ablation). Changes in heart rate can also potentially cause changes in tissue thickness/heart chamber size, as a faster heart rate results in less relaxation of tissue between beats. Optionally, these effects are measured, for example, by use of periodic spot-checks to determine the thickness of reference regions of tissue, information which is optionally used to update the reconstruction. In some embodiments, modeling is used (e.g., modeling of chamber size/tissue thickness as a function of heart rate) to make suitable adjustments to the transform. Again, the transform results Y' are optionally dynamic (e.g., showing time-dependent changes), stabilized (e.g., suppressing changes by accounting for their effects), or any suitable combination of the two.

Measures to Reduce Artefactual Flattening of a Reconstruction

Potentially, the transformation of a V-cloud to an R-cloud produces an intermediate result where scaling along one of physical spatial dimensions is inconsistent with results of the other spatial dimensions. For example, in the transform $Y=\text{diag}(a)X+UW'$, with $a=(a_x,a_y,a_z)$, one or more of the vector components $a_x$, $a_y$, $a_z$ may be too small with respect to another of the components. Where two of the components are scaled about equally, and a third is scaled too small, the resulting R-cloud may collapse along that third component's direction, assuming to a "pancake" or "pita" shape. Such a dimension collapse may occur, for example, if known distances among sister locations which receive penalties for being distorted tend to be oriented parallel in a particular plane. For example, a probe with a linear-shaped distal end carrying the electrodes may enter a reconstructed space in a direction substantially perpendicular to a particular wall, resulting in less sampling of the reconstructed space with the probe oriented parallel to that wall. Under some circumstances, for example, when all the measurements (or a large portion thereof) are from lines perpendicular to a particular wall, penalty minimization may result in aligning all the location points of the location cloud in one (or nearly in one) plane.

In some embodiments, R-cloud flattening is resisted (optionally as a pre-processing step) by finding the natural axes of the V-cloud (e.g., by a statistical method such as principle component analysis), and then adjusting scaling along the axes as necessary to ensure that the variance is the same along all the axes; optionally while also ensuring that the variance along each axis is also independent of the variance in the other axes (i.e., the covariance is zero). Optionally, the adjusted V-cloud is then used as the direct input to a V-cloud to R-cloud transformation. This pre-processing step is also referred to herein as "whitening", by analogy with image processing to achieve white balance of red/green/blue channel color images (each channel corresponding to a spatial axis, in the analogy) that might be "collapsed" in one or more channels (e.g., due to illumination conditions).

Additionally or alternatively, in some embodiments, the choice of constant vector a is subject to an anti-flattening penalty term based on a cost function such as the harmonic average (e.g., the sum of the multiplicative inverses) of its components:

$$\frac{1}{a_x} + \frac{1}{a_y} + \frac{1}{a_z},$$

optionally suitably normalized (e.g., to the Euclidean length of a). Then, should one of the components $a_x$, $a_y$, $a_z$ become small compared to the others, the penalty associated with this distortion rises quickly. Potentially, this prevents a flattened R-cloud result from attracting the cost-minimizing algorithm which seeks a vector a, the components of which have been observed to be generally similar to each other in a correctly-proportioned R-cloud, in accordance with some embodiments of the invention.

Outliers

An aspect of some embodiments of the present invention relates to the removal of potential outlier measurements from contribution to the determination of a transformation that converts a V-cloud to an R-cloud. In some embodiments, the outliers may also be removed from the V-cloud itself, and so will not be represented in the R-cloud.

For variety of reasons (e.g., intermittent changes in circuit properties and/or electrical interference from the environment), measurements obtained for use as part of the V-cloud are subject to potential errors. Detecting this error may be performed by analyzing individual measurements, for example: as lying within or outside a range of expected values, and/or as lying well within or at some extreme of a range of actually observed values. Measurements which appear erroneous in one or more of these senses may be classified as outlier measurements, or "outliers".

Outlier measurements which may be acquired during collection of V-cloud measurements are optionally removed from use at any stage of data processing, e.g., during measurement itself, during transforming a V-cloud to an R-cloud, and/or after formation of the R-cloud. In some embodiments, expected ranges applied in outlier detection are at least partially based on filters such as threshold rules, statistical rules, and/or rules limiting how quickly and/or by how much measurements may change from moment to moment.

In some embodiments of the invention, at least some outlier removal is performed during the process of discovering an optimal (e.g., penalty function-minimizing) transformation converting a V-cloud to an R-cloud, based on the effects of a measurement on the optimization process itself. Intermediate results of optimization are used for the purpose of detecting outliers. In turn, optionally removing outliers and/or their influence from the results of R-cloud reconstruction potentially affects how identification of the optimal transformation proceeds.

In some embodiments, outlier identification comprises use of a penalty term that increases as the similarity between distances of sister locations in the R-cloud and desired sister distances decreases (a distance distortion penalty), indicating outlier sister measurements. The overall penalty minimization process optionally calculates a distance distortion penalty as part of finding a V-cloud to R-cloud transformation with the aim of preserving known distances.

It is noted that such automated removal of measurements according to a positive effect on the transformation may be used also for measurements that are not outliers. Optionally, a step of transform improvement comprises test-removing one or more samples and checking the effect of such removal on transform score. Optionally, a plurality of different measurements and/or sets thereof are so removed. Optionally, a transformation is considered stable if removing random samples does not significantly affect the transform and/or its sore (e.g., having less than a threshold size effect).

Sampling

An aspect of some embodiments of the invention relates to transforming fewer than all measurements from V-cloud to R-cloud. In some embodiments of the invention, measurements that appear redundant are ignored. For example, multiple samples taken at similar times and/or with similar values may be ignored. Optionally or additionally, samples are selected to provide a spatial uniformity. In one example, V-cloud is partitioned, for example, based on voltage levels and in each partition no more than a certain number of samples are used. Optionally or additionally, a uniformity or diversity of samples may be desired (e.g., samples at similar times and/or similar physiological cycles). Optionally or additionally, samples are selected based on continuity in V-cloud and/or R-cloud. In some embodiments of the invention, samples are selected statistically (e.g., based on a random number generator) and based on the transformation generated form these samples, a second, larger set of samples which appear to cover the cavity relatively uniformly, are selected. For example, for each unit space of a certain size, for example, between 2 and 10 mm cubes, a maximum number of samples may be defined.

In some embodiments of the invention, it is desired that samples form locations only briefly visited be used, e.g., for completeness, while ignoring multiple samples of an often visited location.

In some embodiments of the invention, the total number of samples to be used is defined. Optionally, when new samples are measured, older samples and/or samples in proximity to new samples, but which are older (e.g., above a threshold) are dropped.

In some embodiments of the invention, one set of samples is used for generating the transformation and a different set is actually transformed. The different set may be larger or smaller, for example, by a factor of at least 2, 10, 20, 50, 100 or intermediate values.

In some embodiments of the invention, the number of samples may depend on the importance of a region. Optionally, a user may indicate a region at which a larger or smaller number of sample sis to be used, for example, a region of greater interest. Indication may be, for example, by indicating interest and/or by anatomical labeling and/or task specific data (e.g., PV locations if the task is PVI).

In some embodiments of the invention, the volume of the V-cloud is divided into voxels (e.g., of equal volume and/or shape, optionally size weighted by a salience value), and one (or other number) of measurements used from each such voxel. In some embodiments of the invention, a measurement includes measurements taken simultaneously by all the catheter electrodes.

In some embodiments of the invention, the number of measurements to be is decided (e.g., 1000, 5000, 10,000, or smaller or intermediate or greater numbers) and the number of voxels is selected accordingly. Each voxel is checked to see if it is populated or not. If the number of populated voxels is smaller than the decided number of measurements, the voxels may be subdivided or the V-cloud re-divided into a larger number of voxels until the decided number of voxels is populated. In some cases, the shape of the voxels may be modified and/or voxels combined in order to reach a desired voxel-measurement population status. In some cases, evaluation of voxel occupancy is statistical, in that only a sample of the voxels are tested and the resulting occupancy level evaluated based thereon.

Normalization

An aspect of some embodiments of the invention relates to normalizing values in V-cloud. Optionally, values are normalized along axes (e.g., for each field being measured. Optionally, normalization is to a fixed range, for example, 0 . . . 1 or −1 . . . 1

For example, each Vx measurement is normalized so that the voltage at the pad Vx+ is 1 and the voltage on the pad VX− is 0 (e.g., a voltage measurement of zero may be mapped to 0.5).

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Exemplary Methods and Systems for Tissue Geometry Reconstruction from Intrabody Probe Data Reference is now made to FIG. 1A, which is a schematic flowchart of a method for reconstructing a representation of a body cavity using an intrabody probe 11 (shown, for example, in FIG. 12), according to some exemplary embodiments of the present disclosure. Further reference is made to FIG. 12, which schematically represents a navigation and treatment system 1 used with a reconstruction service module 21, according to some exemplary embodiments of the present disclosure.

Acquisition of Spatial Position Data from Electric Field Measurements

In some embodiments, a method of acquiring position data (as noted above—data that can be used to find a position value) comprises inducing at least one time-varying electromagnetic (EM) field 4 (for example, three or more crossing electromagnetic fields, each of a different frequency) generated by an electromagnetic field generator/measurer 10 (which is optionally itself comprised of a plurality of field generation modules) using electrodes such as body surface electrodes 5 across a region of body 2 including a body tissue region 7 that is targeted to be navigated by catheter 9 comprising catheter probe 11. Herein, examples shown with respect to a catheter probe 11 should be understood to be optionally applicable to any navigable intrabody probe 11 suitably configured for obtaining electromagnetic field voltage readings by at least two sensors distanced from each other by a known distance. Typically, the time varying electromagnetic field is induced with a total inter-electrode voltage (body surface-to-body surface) of one volt or less, at a frequency of between about 10 kHz and about 1 MHz.

At block 110, in some embodiments, position data is acquired from an intrabody probe (e.g., catheter probe 11), from each of a plurality (e.g., 2, 3, 4 or more) of sensing electrodes 3 on the probe which act as sensors to measure electromagnetic field data indicative of position. It is noted that a single electrode may be sufficient, for example, if some other local constraint is used, for example, based on a predefined movement speed (e.g., value or range) of the electrode.

In some embodiments of the invention, the sensing electrodes 3 are in a known spacing relative to one another; for example, fixed at certain distances from one another. Alternatively, if the sensing electrode 3 spacing is dynamic (e.g. because the probe 11 can bend), the spacing can be estimated to change in correlation with parameters of probe operation (e.g., active deformation) and/or measured contact (e.g., deformation correlated with measurements of contact force). The known spacing is used, in some embodiments, as part of the data used in the reconstruction of the body cavity (e.g., a lumen of a hollow organ such as a heart chamber) within which the intrabody probe moves.

In some embodiments, position data is received by computer circuitry, e.g., from the sensors in real time or from a computer memory that saves data received from the sensors.

Before continuing with discussion of elements of FIG. 1A, reference is now made to FIG. 2, which schematically represents schematically represents sample positions of a voltage sample cloud shown mapped via a voltage/spatial mapping to a space representing a cavity of a left atrium 50 of a heart 55. (Some embodiments may reconstruct other and/or additional parts of the heart, for example, the right atrium, the right ventricle, the left ventricle, valves and/or blood vessels leading in and/or out of the heart, such as the aorta and/or vena cava and/or coronary sinus and/or coronary arteries and/or pulmonary arteries and/or veins; some embodiments reconstruct other cavities in the body, such as abdominal cavity, GI cavities (e.g., stomach), the bladder and/or the brain. In some embodiments, the cavity includes tissue, for example, substantially homogenous tissue, for example, in the case of the liver or within brain tissue, and measurements may be taken in solid tissue or from within blood vessels or other natural lumens which pass through the tissue.) The figure shows positions (dots generally marked as 202) in left atrium 50. The dots represent locations at which voltage measurements were taken for reconstructing a shape of left atrium 50. The voltage measurement taken at locations 202 may serve as an example of position data indicative of the positions of locations 202. It is noted that additional voltage measurements, of activation potential activity, for example, may be taken as well.

A ventral view of a section of the wall of left atrium 50 is shown in the background of locations 202; including roots of four pulmonary veins 48. The semi-transparent heart 55 drawn in ventral view at the lower-right side of FIG. 2 (and in other figures herein) is provided for orientation to the anatomy of the heart. Right heart atrium 54 (semi-transparent light gray region) is visible from the ventral of the heart. As drawn, left atrium 50 is shown as the darkest region, positioned on the far side of heart 55 (in the same orientation as the larger left atrial wall section in the main part of FIG. 2).

The locations 202 are drawn in clusters of four sister positions connected by a dotted line. Each cluster of sister positions represents electrode positions of a four-electrode probe 11 (shown at lower right of LA 50). For purposes of illustration, only some of locations 202 are shown. For live sampling during a procedure, a sampling rate of several samples per second is used. The number of samples per second may be, e.g., at least 10, 25, 50, 100, or an intermediate number of samples per second). Herein, figures showing a straight-line, four-electrode probe with irregular spacing between the electrodes are used for the purpose of providing examples. Optionally, any multi-electrode probe suitable for introduction to the body cavity of interest can be used. One potential advantage of some embodiments of the present invention is that it is suitable for use with a wide variety of intrabody probes which are already commercially available, and may be in widespread use.

In some embodiments, a probe 11 having 2, 3, 4, 5, 6, 7, 8 or more electrodes 3 is used. Measurements taken from the electrodes at substantially the same time optionally include or define a set of measurements from electrodes constrained in their relative positions by a known geometry of their arrangement, or at least by the distance between them. Optionally, well-characterized movements of the probe (bending near a fixed location, axial translations of the catheter, etc.) are used as parameters indicative of bending to help to define known geometrical rearrangements among sets of measurements taken at different times.

The electrode 3 spacing is optionally at any suitable distance, and may be regular or irregular among different pairs of electrodes. In some embodiments, an intrabody probe comprises a rigid section, with electrodes fixed to the rigid section at known (e.g., predetermined and/or measurable) distances from each other. In some embodiments an intrabody probe comprises multiple flexible probe segments (arranged to open to a predetermined and/or measurable spread-out configuration of inter-electrode distances, e.g., in a "basket"-type and/or "umbrella"-type configuration), each bearing a plurality of electrodes in a configuration extending therealong. Potentially, measuring from more and/or more widely distributed electrodes speeds up reconstruction, e.g., allows "snapshot"-type mapping of a cavity in which the probe is deployed.

Additionally or alternatively, in some embodiments, electrodes are positioned on a flexible member which can assume a curved shape (e.g., by its own predisposition to bend, under remote control, and/or in response to contact force); optionally to the extent of forming a circular and/or spiral configuration. A catheter carrying such a probe is sometimes referred to as a "lasso" catheter. In some lasso catheters, the electrodes are arranged in pairs, wherein the distance between electrodes within a pair is small enough to be fixed even when the catheter as a whole curves. Accordingly, some lasso catheters may include 10 electrodes that define 45 electrode pairs, among which 5 pairs are characterized by a fixed inter-electrode distance, and the inter-electrode distances in the other 40 pairs are not fixed. The relative positions of the electrodes on the flexible member are optionally calculated from knowing a control state of the flexible member, and the effect of that control state on the flexible member geometry.

Optionally, electrodes of the flexible member transmit electrical signals between each other, and the level of the electrical signal is used to calculate a distance and/or a constraint thereon. In some embodiments, a catheter includes one or more pairs of electrodes with known intra-pair distance (i.e., known distance between the members of the pair), and unknown inter-pair distances (i.e. unknown distances between the pairs or between electrodes that belong to different pairs). In some embodiments, only two electrodes with known distance between them is included in the catheter probe. In some embodiments, the distances between some electrodes on the catheter probe are known, and the distances between some electrodes on the same catheter probe is unknown. All these may be used in embodiments of the invention, as one inter-electrode distance is sufficient to provide a "ruler" to be used in the reconstruction as described below in the context of block 112, although a larger number of known distances may yield a better reconstruction. A reconstruction may be identified as better than another if it provides a more useful approximation of the target than the other reconstruction.

In some embodiments, a plurality of probes is used. Optionally, a first probe (a straight probe or a flexible member probe, for example) is used to obtain position data used to reconstruct the target space, and a second probe (e.g., an ablation probe) is guided to one or more selected positions within the target space, based on the reconstruction, and on measurements made by electrodes of the second probe which correlate with measurements assigned to positions based on the position data obtained from the first probe.

Optionally, sensors in the catheter rely on wireless transmission to transmit measurement to be recorded and processed.

Probe Structure-Constrained and Coherence-Constrained Reconstruction

At block 112, in some embodiments, the known spacing of sensing electrodes 3 is used in voltage/spatial mapping, whereby the body cavity shape is reconstructed from voltage measurements measured by probe electrodes 3.

A major principle of the reconstruction and/or in particular transformation from V-cloud to R-cloud may be understood as using the structure of the intrabody probe as a kind of ruler. As this ruler is moved among multiple locations, it does not change its length. In some embodiments, possible transforms are weighted by the degree to which they keep this length constant. In embodiments where this is the only criterion for choosing a transform, the transform that keeps this length most constant is chosen to be used for the voltage/spatial mapping. Naturally, when distances between more than two electrodes are known, there are more rulers that should be fixed.

For example, in transforming each measurement made by one sensor at one instance to a corresponding location (corresponding to the location of the sensor at the instance), it is desirable that measurements taken by two sensors, spaced from each other by 2 mm (for example), are transformed to two locations, spaced from each other by 2 mm. At least, if the two measurements are transformed to locations 3 mm apart from each other, it is desirable that this distance of 3 mm is the same regardless of where the probe is. The requirement for a fixed length of the ruler may be translated to a requirement of a flexible transformation between measurement gradient and location gradient. For example, the distance between the location assigned to sensor 1 and to sensor 2 is always to be the same, even if the difference in voltages measured by sensor 1 and sensor 2 varies appreciably (for example, by a factor of 10 or more).

In some embodiments, a method of finding a transform that keeps the sister distances (i.e., distances between locations assigned to two positions of a ruler) constant comprises an optimization process. This can be understood as starting with a trial transform, estimating the degree to which rulers lengths change under this transform, and iteratively changing the transform to reduce this degree, until a minimal degree of change of rulers lengths (and/or maximal stability of rulers lengths) is achieved.

In some embodiments, the trial transform is changed iteratively not only to maximize the stability of rulers lengths, but also to satisfy one or more additional constraints in some weighted combination. In terms of the "ruler" concept, the ruler length is allowed to get a little longer or a little shorter in some region (and/or for some particular measurement) if that helps to produce a reconstruction which does a sufficiently better job of maintaining another constraint criterion overall. In algorithmic terms, there is a "cost" to increasing change of the ruler length, and a "cost" to increasing failure to maintain any other criteria; and the result chosen is the one that minimizes their joint cost (optionally weighted using predefined weights).

It should be appreciated that the rulers need not be fixed, rather they define a constraint with a certain weight. In some embodiments, a constrain may, a-priori be flexibly defined, for example, defining a range of possible distances (optionally with a distribution function). For example, if a constraint rule defines a range of possible distances, the actual distance determined by the transformation can be expected to change as a better transformation is found.

One general type of constraint criterion used, in some embodiments, is to maintain the spatial coherence of the transformation, for example by one of the methods described in the Overview. The general principle of coherence is that positions nearby in space should also be nearby in their other properties (and the closer in position, the closer in their properties); and in particular, nearby in the values measured in them to produce position data. For example, one kind of coherent transform is a transform that transforms more-similar voltage readings to more-nearby locations, and less-similar voltage readings to locations further away from each other. In some embodiments, distance between measurements is defined according to the natural distance between them. For example, in some embodiments, the voltages of three different electrical fields are measured as indications of position. These measurements may be represented as points in a three-dimensional space. For example, a Cartesian system of axes may be used to present the voltage readings, when a reading of, say, 10 mW at each field (e.g., at each frequency) is represented at a point distanced from each of the axes by 10 mm. This way, measurements collected at many instances (say, 6000 measurements taken during 1 minute at a rate of 100 measurements per second) may be represented as a cloud of measurements, referred to herein as a V-cloud. The shape of the V-cloud is very different from the shape of the target, because the fields are not linear as axes in a Cartesian system.

Still, the inventors found that by using coherent transforms that keep ruler length constant or at least constrained, the V-cloud may be transformed into an R-cloud that is a useful approximation of the shape of the target. In some embodiments, the usefulness of the approximation may be enhanced by using natural distances between measurements in the V-cloud and between locations in the R-cloud. The natural distance between two points in a cloud may be the shortest path going from one point to the other without going out of the cloud. The use of natural distance was found to make the transforms segmentation preserving, and avoid or decreases merging of protruding shapes into each other.

As mentioned herein, in some embodiments, one or more additional sources of information are used as constraints during production of a reconstruction. These additional constraints may also be applied flexibly by assigning them costs, and finding a transform that minimizes the overall cost, considering rule length stability, transform coherency, and any other constraint. Examples of additional constraints are described, for example in relation to functionality blocks 1102, 1106, 1108, 1110, and 1112 of FIG. 11.

Display of Reconstructed Structure

At block 114, in some embodiments, a current state of the reconstructed structure produced in block 112 is provided for use. In some embodiments, uses of the reconstructed structure include one or more of:

Display and/or navigation: In some embodiments, a state of a procedure underway within the body cavity is shown in a view that includes a graphic model of the reconstruction. A model of the reconstruction may be any representation of the shape of the body cavity based on the R-cloud, for example, a three-dimensional rendering of a mesh that snugly covers the locations that make together the R-cloud. Optionally, the view also includes a model of intrabody probe 11 at a position within the model of the reconstruction. The position of the probe model in relation to the reconstruction model corresponds to the estimated position of the actual probe in relation to the actual target.

Data indicating actual movements of the probe are optionally used to model probe motions in the displayed reconstruction model, allowing the display to be used as an aid to navigation. In some embodiments, the displayed view comprises a real-time updated view of a scene maintained by a graphical display engine (e.g., a game engine), for example as described in United States Provisional Application Nos. 62/422,705 entitled REAL-TIME DISPLAY OF TISSUE DEFORMATION BY INTERACTIONS WITH AN INTRA-BODY PROBE; 62/422,708 entitled TISSUE MODEL DYNAMIC VISUAL RENDERING; and 62/422,713, REAL-TIME DISPLAY OF TREATMENT-RELATED TISSUE CHANGES USING VIRTUAL MATERIAL; each filed on Nov. 16, 2016, and the contents of each of which are included herein by reference in their entirety. It is noted, however, that in the above-referenced provisional patent applications, the target was modeled by a CT image, while in accordance with some embodiments of the present invention, the target is modeled by a reconstruction model of the target.

Procedure assessment: In some embodiments, the reconstruction is used, together with records of intrabody probe movements, records of other procedure actions (such as treatment activations), and/or measurements of tissue from locations within the reconstructed volume, to generate an assessment of the procedure; e.g., an assessment of current procedure status and/or likelihood of procedure success. Optionally, the assessment is generated as the procedure is underway. Such an assessment is of potential use, for example, in making changes to procedure planning. Optionally, the assessment is generated after a procedure, for example, as an estimate of a likelihood of procedure success. Methods of procedure assessment are described with relation to several different types of procedure outcome estimators, for example in U.S. Provisional Application No. 62/422,748 entitled ESTIMATORS FOR ABLATION EFFECTIVENESS; filed on Nov. 16, 2016, the contents of which are included herein by reference in their entirety.

Procedure planning and/or re-planning: In some embodiments, the reconstruction is used, together with records of intrabody probe movements, other procedure actions (such as treatment activations), and/or measurements of tissue from locations within the reconstructed target, to support planning revisions to a procedure. For example, a line of ablation initially planned for a heart chamber on the basis of pre-procedure imaging is optionally revised to match anatomical details discovered by a reconstruction of the heart chamber, based on movement of the intrabody probe during the procedure itself. Optionally, deviations in treatment execution from an original plan (e.g., missed ablation positions and/or unforeseen delays in ablation) are compensated for based on analysis of details revealed in the reconstruction. The analysis may be by the physician carrying out the procedure and provided with a view of the reconstruction model, or by a processor programmed to analyze the reconstruction. In some embodiments, for example if another treatment procedure is found to be necessary at some time after an original procedure is completed, a reconstruction generated during the original procedure is used as a basis for planning the new treatment procedure.

At block 116, in some embodiments, a decision is made whether or not to return to block 110 and continue acquiring probe geometry-constrained voltage measurements. If so, the flowchart cycles back to use data from block 110 to adjust the reconstruction at block 112 and then provide for use another version of the reconstructed structure. This loop optionally continues for as long as a procedure continues. In some embodiments, the loop continues in order to update the position of the probe model in the reconstruction model. In some embodiments, the position of the probe model is updated, but the reconstruction model is not updated. This may be the case, for example, when the reconstruction model is sufficiently detailed, and further updates may yield no significant additional information for the physician. Unnecessary updates may distract the physician's attention (e.g., by causing the view to flicker).

Accounting for Variability in Voltage/Spatial Mappings

When methods according to some embodiments of the present disclosure are carried out, voltage measured at a given point may change over time; for example, due to movement of tissue around the point where the voltage is being measured. Blood, muscle, bone and air have different impedance properties, and as their relative spatial distribution changes around a heart ventricle (or any other body cavity to be reconstructed), so does the spatial distribution of voltages in the heart ventricle. Accordingly, a static point may be reconstructed to appear at different places due to changing conditions, and any structure reconstructed based on the voltage readings may be reconstructed to have a shape distorted to different extents and in different manners due to the changing conditions. The distortions may also be dynamic, that is, be different at different times. For example, the changing conditions may cause measurements to change, and the changed measurements may cause selection of a different transformation, which, in turn, may reconstruct the static point to appear at a different place.

Figure 3A:
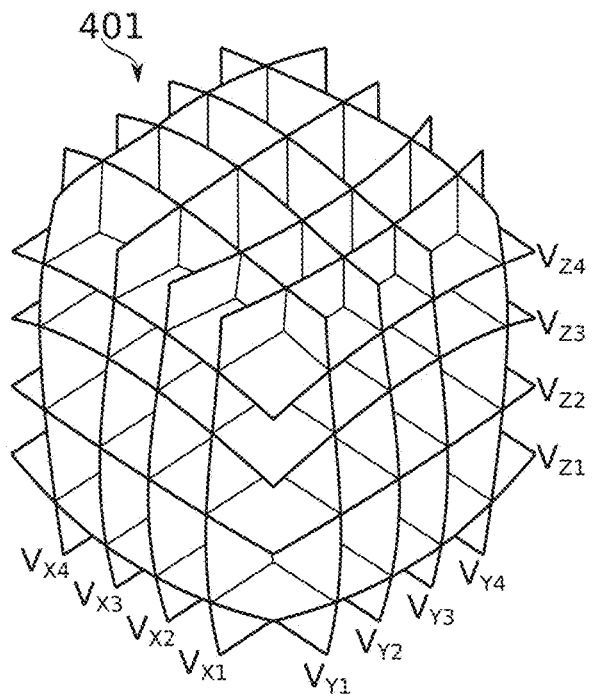
FIGS. 3A-3C schematically represent changes in the spatial distribution of voltages measured within crossing electromagnetic fields as a function of changing conditions such as tissue motion, according to some exemplary embodiments of the present disclosure.
Figure 3B:
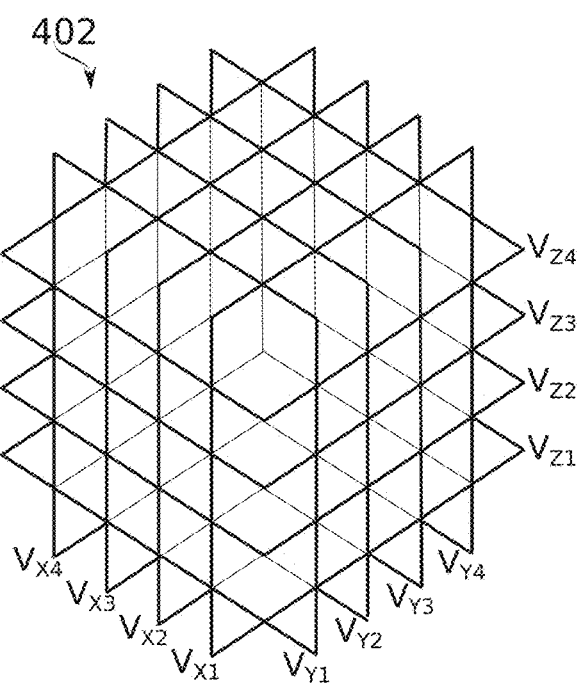
Figure 3C:
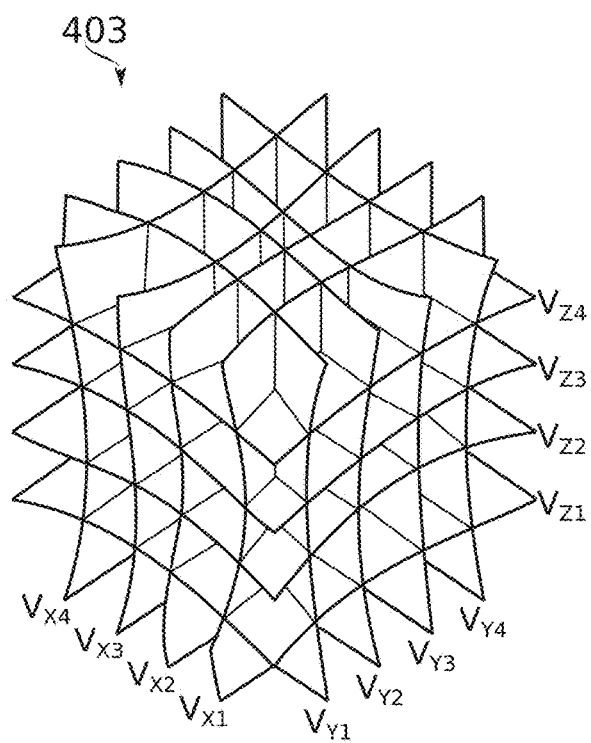

Reference is now made to FIGS. 3A-3C, which schematically represent changes in the spatial distribution of voltages measured within crossing electromagnetic fields under different conditions such as different phases of motion, according to some exemplary embodiments of the present disclosure. For example, each of FIGS. 3A, 3B, and 3C may represent a reconstruction of the same structure (not shown) under different conditions.

Several different types of changes can take place during a procedure which could cause a statically defined voltage/spatial map to fall in and out of registration with reality. Significant among these changes are heartbeat, respiration, and longer-term changes such as changes in hydration state and development of tissue edema.

3-D voltage/spatial mappings 401, 402 and 403 of FIGS. 3A-3C (e.g., as examples of transform functions) together may represent cyclical change in spatial voltage distribution as a function of a parameter such as heartbeat phase and/or respiratory phase. Iso-voltage surfaces VXn, VYn and VZn represent the same voltage in each mapping, but their positions shift due to changes in the environment around them.

Assuming voltages within a reconstructed structure are distributed on a rectangular grid, similar to that drawn in FIG. 3B, mapping 402 may represent a voltage/spatial mapping at a phase where distortion between the structure and its reconstruction are minimal. At another phase, for example, of heart expansion, the reconstruction may take the form of voltage/spatial mapping 401, which is distended outwardly and non-uniformly. At an opposite phase of heart expansion, the voltage/spatial mapping 403 becomes inwardly collapsed: perhaps non-uniformly as shown.

Such distortion over time is just one example of change. There may also be translation of electric fields as a function of phase, and/or of time.

Figure 5A:
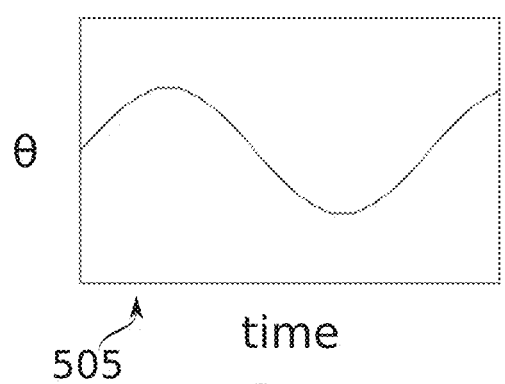
FIGS. 5A-5B schematically represent, respectively, variation over time of a respiration phase $\theta$, and correlated position changes of body tissue, moved during respiration, according to some exemplary embodiments of the present disclosure.
Figure 5B:
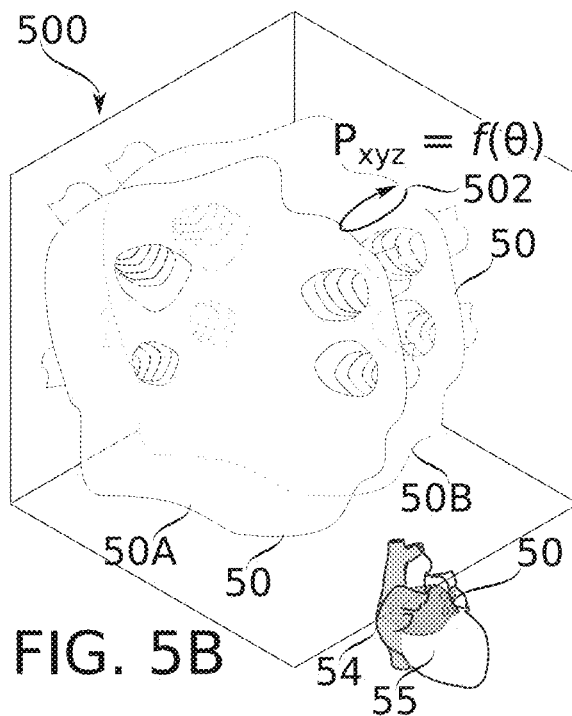
Figure 5E:
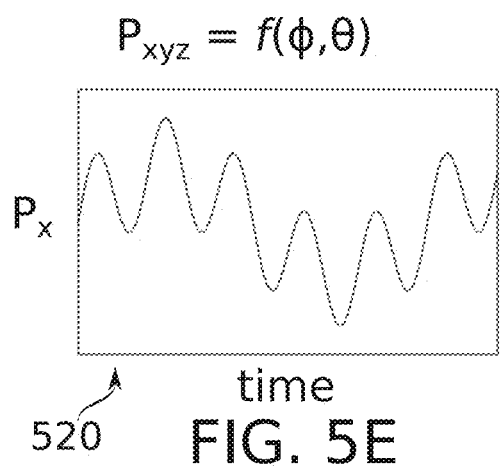
FIG. 5E schematically represents variation over time of a position Px as a function of both heartbeat phase $\phi$ and respiration phase $\theta$, according to some exemplary embodiments of the present disclosure.

Reference is now made to FIGS. 5A-5B, which schematically represent, respectively, variation over time of a respiration phase $\theta$, and correlated position changes of body tissue 50 moving between positions 50A, 50B during respiration, according to some exemplary embodiments of the present disclosure. Further reference is made to FIGS. 5C-5D, which schematically represent, respectively, variation over time of a heartbeat phase $\phi$, and correlated position changes of body tissue 50 moving between positions 50C, 50D by the heartbeat, according to some exemplary embodiments of the present disclosure. Reference is also now made to FIG. 5E, which schematically represents variation over time of a position Px as a function of both heartbeat phase $\phi$ and respiration phase $\theta$, according to some exemplary embodiments of the present disclosure.

In some embodiments of the current invention, phasic distortion of a voltage/spatial mapping is used to help maintain position accuracy in the mapping as a function of heartbeat phase $\phi$, and/or respiration phase $\theta$. Another way to describe this is that the voltage/spatial mapping is converted to a voltage/spatial/phasic mapping—for example a mapping of voltage V into not only X, Y, and Z spatial axes, but also onto phasic axes $\phi$ and/or $\theta$.

For example, considered ideally, a point P in region 502 of a left atrium in a voltage/spatially mapped space 500 (FIG. 5B) describes a path Pxyz as a function of respiration phase $\theta$, which varies over time as shown in graph 505 of FIG. 5A. For purposes of illustration, the path is shown as part of a larger movement of the left atrium 50 comprising a displacement between positions 50A and 50B, but other movements are also possible.

Figure 5C:
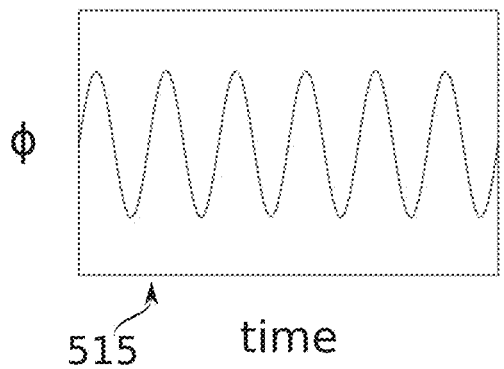
FIGS. 5C-5D schematically represent, respectively, variation over time of a heartbeat phase $\phi$, and correlated position changes of body tissue, moved by the heartbeat, according to some exemplary embodiments of the present disclosure.
Figure 5D:
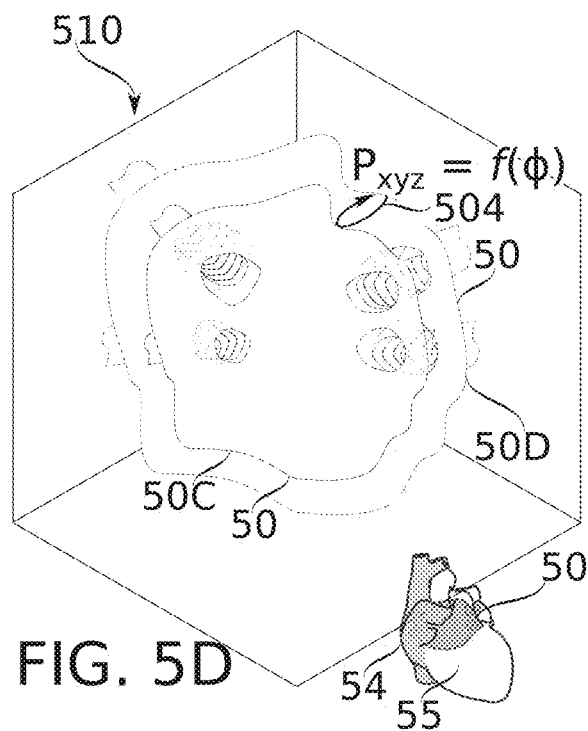

Region 504 of a left atrium in a voltage/spatially mapped space 510 (FIG. 5D) describes another path Pxyz as a function of heartbeat phase ϕ, which varies over time as shown in graph 515 of FIG. 5C (and more quickly than respiration phase θ). Again for purposes of illustration, the path is shown as part of a larger movement of the left atrium 50 comprising periodic contraction and expansion between positions 50C and 50D, but other movements are also possible.

The phase of a heart along a periodic movement (which may be designated above as θ and/or ϕ may be determined, in some embodiments, by measurement. For example, measurement of heartbeat phase optionally uses ECG, oximetry, or pulse meter; and/or measurement of respiratory phase optionally uses a motion sensor, air flow meter, and/or coupling to the operation of a respiratory machine. Optionally, another method of phasic motion measurement is used.

In actuality, since respiration and heartbeat are generally out of phase with one another, the motions experienced by any particular region are subject to more complicated phasic patterns, for example, the phasic pattern of graph 520 of FIG. 5E, which shows a position Px of some region along a single axis as a function of time, where both respiration (varying as θ in FIG. 5A) and heartbeat (varying as ϕ in FIG. 5C) affect position Px.

Figure 12:
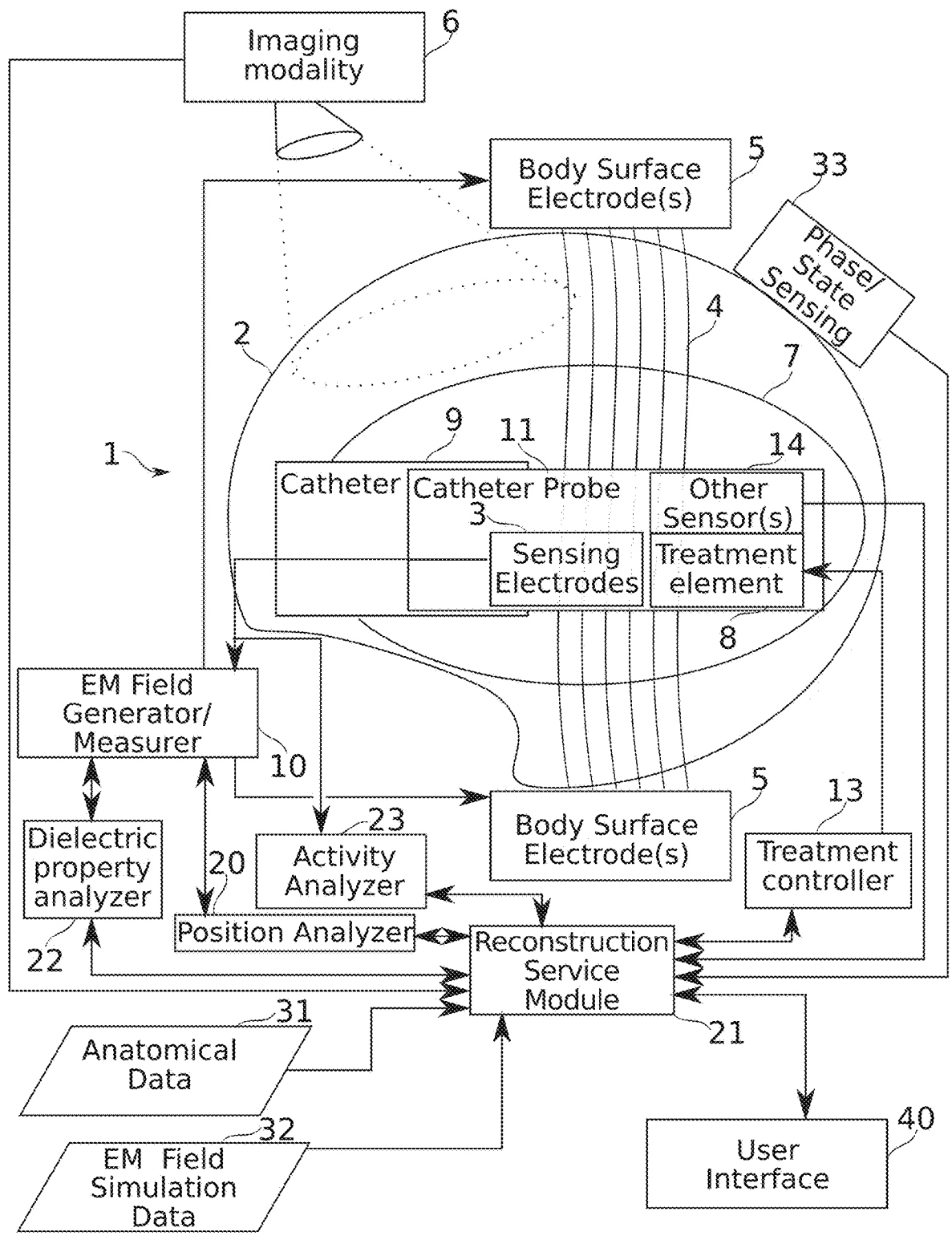
FIG. 12 schematically represents a catheter navigation and treatment system used with a reconstruction service module, according to some exemplary embodiments of the present disclosure.

Given $V_{xyz}=f(\Theta,\Phi)$ for any given region of the voltage/spatial map (i.e., given a voltage/spatial/phasic map), it is a relatively straightforward matter to look up a current position from phase state data provided, for example by means of phase state sensing 33 (FIG. 12).

In some embodiments, the definition of $f(\Theta,\Phi)$ is at least partially based on voltage simulations, imaging, and/or atlas information; e.g., simulations of electrical potential based on how the anatomy is shaped at different phases of respiration and/or heartbeat. Optionally further measurements acquiring voltage measurement data are used to refine a model established by the simulations as a framework (e.g., by weighted combination of simulations and new data).

In some embodiments of the invention, the definition of $f(\Theta,\Phi)$ is at least partially created by "bootstrapping" from acquired voltage measurement data. For example, a stationary probe experiences phasic differences where it sits. Even for a moving probe, correlation and/or frequency analysis can potentially separate phasic changes at a certain set of frequencies from those due to probe motion.

However, it can be difficult in some parts of a procedure to distinguish phasic motions of the probe (e.g., due to period disturbance by contracting tissue) from phasic changes of the electromagnetic field environment. This is mitigated somewhat, in some embodiments, since the positions of main interest are not usually positions of a probe in fixed space as such. Of more interest, in some embodiments, are positions of the probe relative to—and especially, while in contact with—some particular region of (possibly moving) tissue. The effects of positioning errors occurring while the probe moves freely through a body cavity may be of relatively minor consequence. The effects of positioning errors occurring once the probe is in contact with tissue and providing treatment such as ablation, however, can have less marginal consequences.

In some embodiments of the invention, particular treatment is given to phasic voltage changes occurring while a probe is in contact with tissue. With strong enough contact established (e.g., constant contact even in view of heart contractions), it can be assumed, for example, that the probe is always contacting substantially the same tissue portion throughout all phases of respiration and/or heartbeat. Optionally, contact is measured, for example, using a force sensor (an example of "other sensors" 14 of FIG. 12), and/or by use of voltage measurements which dielectrically and/or by impedance indicate contact (for example, via dielectric property analyzer 22), and/or which indicate electrical activity sensed when tissue is contacted (for example, via activity analyzer 23).

In some embodiments, at each position of such contact, a different "phasic function" is optionally derived. Phasic functions in positions in between measured regions, or for times not measured during contact, are optionally created by interpolation. Even if the phasic function data are incomplete around the whole of a body cavity, it is potentially sufficient to define the result in certain regions of greatest interest, which are often, in some embodiments, the regions where treatment is to be applied.

In some embodiments, phasic and/or other time-dependent changes to the shape of a body cavity are modeled (e.g., simulated) with respect to values of a measurable parameter that indicates the changing shape. Actual measurements of voltage are optionally used to constrain this model, potentially allowing time-dependent measurements from a few locations within the body cavity to be used to set the shape dynamics of the entire body cavity. It should be noted that models of changing body cavity shape and simulations of changing voltages within the cavity are optionally both used.

It should be acknowledged that strong contact between heart and probe potentially itself distorts the phasic data (e.g., the heart is being "held in place" by the probe to some degree, and not beating completely naturally). However, it can be understood that this is actually a potential benefit, in some embodiments where a primary concern is for identification of contacted tissue under conditions where strong contact is required.

While phasic changes to a voltage/spatial mapping are potentially among the most disturbing to accurate positioning, there can also be time-evolving changes that are non-phasic. For example, as a procedure progresses over the course of several minutes (e.g., 30-60 minutes or more), there can be changes in the hydration state of the patient which produce a slowly accumulating error in the voltage/spatial mapping being used. In some embodiments, this error is detected by periodically re-visiting one or more sites, and recalibrating the voltage/spatial mapping on the basis of the sequence of observations made. Optionally or alternatively, hydration state is estimated from exogenous data (e.g., by noting relative fluid flux), and a model adjusted to account for expected differences.

Another source of change, related to heartbeat phase, is that average heart size can change as a function of heart rate. A fast-beating heart relaxes less (e.g., because it has less inter-beat time to relax) than a slow-beating one, so that the faster-beating heart effectively is found to shrink. In some embodiments, this effect is extracted by noting changes in voltage measurements that correlate with heart rate. Optionally, a geometrical model of shrinkage as a function of heart rate is used. In some embodiments, the model is calibrated for a larger heart region based on actual observations of heart size change (or, more directly, voltage change) as a function of heart rate in one or a few smaller regions.

Multi-Modality and Multi-Dimensional Mapping

General Use of Intrabody Probe-Acquired Data as Position Data

Figure 1B:
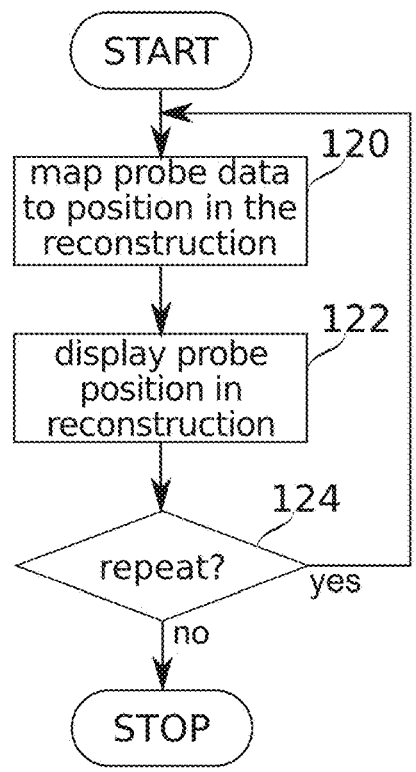
FIG. 1B is a schematic flowchart of a method for using a body cavity reconstruction together with an intrabody probe, according to some exemplary embodiments of the present disclosure.

With particular attention to the use of the reconstruction in display and/or navigation, reference is now made to FIG. 1B, which is a schematic flowchart of a method for using a reconstructed body cavity map together with an intrabody probe, according to some exemplary embodiments of the present disclosure.

At block 120, in some embodiments, data acquired from an intrabody probe 11 in some actual body cavity position is mapped to a position in a spatial reconstruction of that body cavity based on a voltage/spatial mapping, for example, a reconstruction as described in relation to block 112 of FIG. 1A. It is noted that in this sense, the reconstructed cavity "map" is a structure and the acquired data is mapped to positions in this structure and possibly not used in generating the transformations between position data measurement space (e.g., v-cloud) and the map space (e.g., r-cloud). "Mapping" in this context may include acquiring such data at multiple positions to create a data map, indicating data values for different anatomical locations in the body.

At block 122, a view comprising an image showing at least a portion of the reconstruction model is shown, together with a model of the intrabody probe 11 at the position to which it was mapped in block 120. A probe may be mapped to a position according to the positions to which electrodes of the probe are mapped. Electrodes may be mapped to a position based on the readings of position-data that they read. For example, when an electrode reads a voltage, the voltage is transformed to a location (e.g., by a transform as described in relation to block 112), and that location is attributed to the electrode. This way, voltage readings by an electrode are interpreted to be indicative of position of the electrode, and position of an electrode may be interpreted as a position of a catheter (or at least catheter portions).

At block 124, a decision is made to continue repeating blocks 120, 122, and 124 (i.e., the procedure of adjusting the position of the probe in the reconstruction model continues) or not (the flowchart of FIG. 1B ends). Optionally, the mapping and display are performed at an image frame rate of at least 10, 15, 20, 30, 60, 100, or another intermediate frame rate. Optionally, the display can be used and interacted with by a probe operator as if it were a direct display of the intrabody probe 11 itself.

The discussions of FIGS. 1A, 2, 3A-3C, and 5A-5E were primarily in terms of electromagnetic field-guided navigation, where a set of crossed, time-varying electromagnetic fields (typically three crossed fields) are used to provide a frame of reference which can be used by means of voltage measurements. However, the data acquired from an intrabody probe 11 can in principle be one of several other possible data types, for example as is now described in the remainder of this section on multi-modality and multi-dimensional mapping.

Multi-Modality Mapping from Probe-Detected Data

Figure 6:
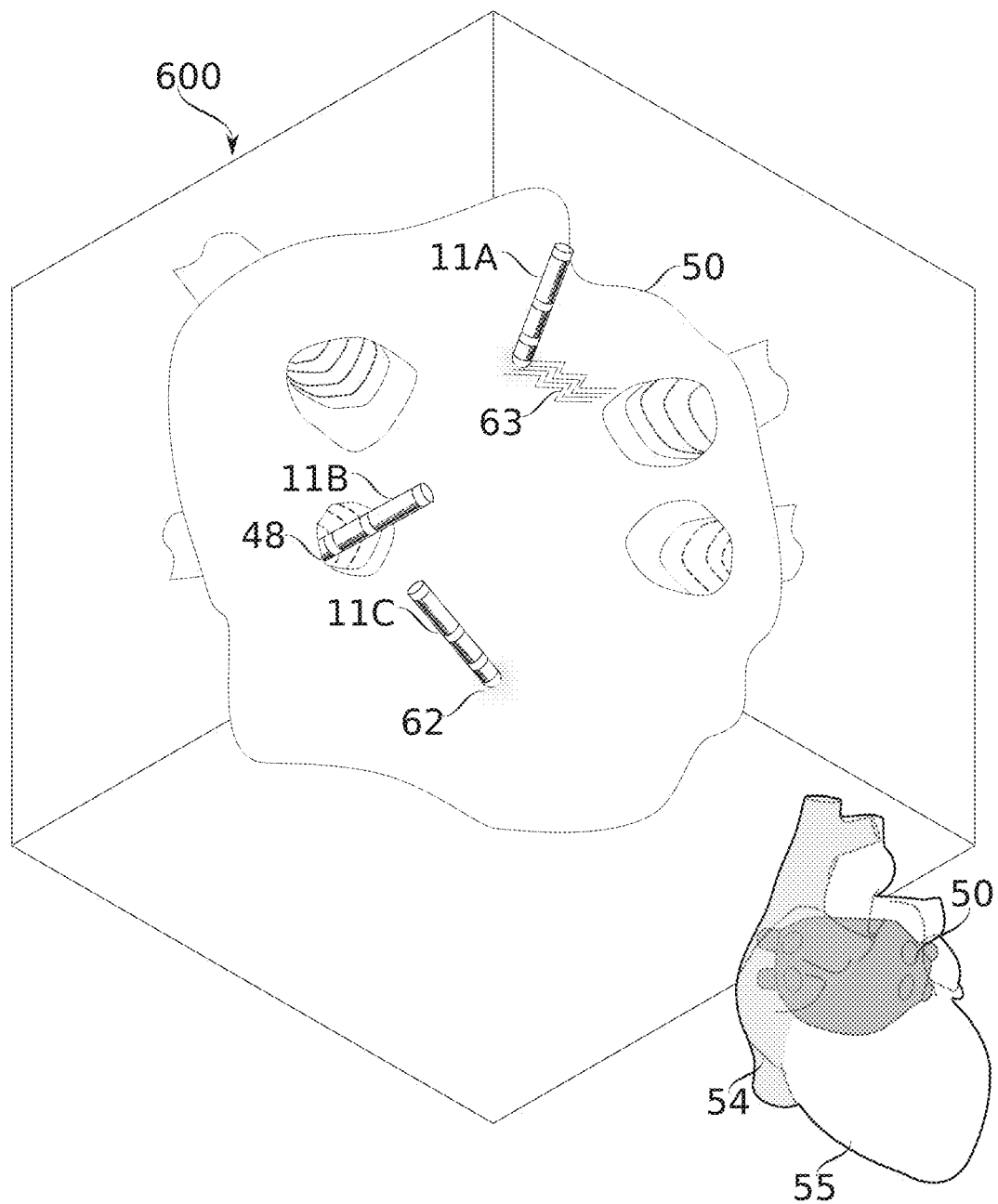
FIG. 6 schematically represents modes of gathering additional position data using an intrabody probe, within a body cavity, according to some exemplary embodiments of the present disclosure.

Reference is now made to FIG. 6, which schematically represents modes of gathering additional position data using intrabody probes 11A, 11B, 11C, within a body cavity, according to some exemplary embodiments of the present disclosure. The probes shown are indicative of different types of data gathering, and do not necessarily imply simultaneous positioning of all the probes.

Probes 11A, 11B, 11C are shown in a space 600 to be mapped, to illustrate acquisition of data from different modalities which can be used to assist in refining and/or using a reconstruction. The different modalities may correspond, in some embodiments, to probe-measured tissue condition sensing data 1105 of FIG. 11. Different types of probe-measured tissue condition sensing are described in relation to each of probes 11A, 11B, 11C.

Probe 11A is shown in the act of measuring endogenous electrical activity 63 in a region of heart atrium wall tissue 50. Optionally, in some embodiments, measured endogenous electrical activity (e.g., an electrogram) is used as an indicator of position, for example, based on a phase delay with which activity is measured at a particular position, compared to some landmark phase, such as the QRS complex of an electrocardiogram (ECG). Optionally, the phase difference is measured relative to an electrode on probe 11A itself, which does not contact the heart atrium wall (also referred to herein as a non-contacting electrode). In some embodiments, the non-contacting electrode may be a ring electrode. Phase-offset correlations between activity measured at the wall and at a non-contacting electrode may potentially help to cancel surrounding noise. This phase delay is optionally treated as creating an additional data dimension applicable across a surface of a heart.

The information gathered this way potentially helps correcting for potential inaccuracies in electro or electromagnetic field-based position data. As an example of such inaccuracies, changes in voltage distribution over time (e.g., as described in relation to FIGS. 5A-5E) could make the same tissue position appear to be slightly different upon a revisit. Registering the electromagnetic field-based position data with electrical activity provides extra information which might prevent unknowingly identifying the revisited (and changed) position with a wrong position, or even help to identify the original position despite its changes.

Probe 11B is shown partially exploring the interior of a root of pulmonary vein 48. Different tissue structures have been found to display noticeably different impedance behaviors which can be gathered by electrodes of an intrabody probe and distinguished through analysis, for example, by a dielectric property analyzer 22 (optionally in communication via electromagnetic field generator/measurer 10 used to operate electrodes 3). In particular, positions within veins and within heart atria are optionally distinguished according to their impedance properties in some embodiments of the present invention, with positions in veins, for example, having the relatively higher impedance value.

In some embodiments, distinguishable dielectric properties of tissue itself can be used as a landmark. Tissue dielectric properties can be measured, for example, as described in International Patent Application No. PCT IB2016/052686 entitled CONTACT QUALITY ASSESSMENT BY DIELECTRIC PROPERTY ANALYSIS, and filed on May 11, 2016, the contents of which are incorporated herein by reference in their entirety.

Impedance changes, for example, due to transitions between two tissue types or between two tissue wall thicknesses, scarring, ablation, edema, and the like) are optionally used as landmarks. Landmarks in turn may be used to register a voltage/spatial mapping to a more accurately determined size. For example, a distance between two landmarks may be known from atlas and/or imaging data; once positions of the two landmarks are known by visiting them and detecting their characteristic properties, the measurements taken at those positions can be constrained to remain at that distance, while other measurement positions are adjusted in between, accordingly.

Additionally or alternatively, such landmarks optionally serve in the re-identification of tissue positions in case of changes to an electromagnetic field-based frame of reference: for example, if an electrode moves, changes its quality of contact, or if a hydration or other state of the patient changes. It is noted that such use of landmarks comprises mapping relative to contact with identified structural features of interest directly, as distinguished from mapping relative to spatially-defined coordinates (at which structural features are supposed to exist). Potentially, this is particularly useful when navigation targets such as in heart atrial wall are in continuous movement relative to spatially-defined coordinates. Optionally, both types of information are used together: for example, a spatial coordinate system is established by measurements of voltages in a spatially distributed electromagnetic fields, and tissue landmarks identified by contact measurements from a probe are assigned coordinates as they are encountered.

Probe 11C is shown in contact with a general region 62 of atrium wall tissue 50 (that is, a region which is not particularly singled out as a landmark). The inventors have found that it is possible, in some embodiments, to detect an anterior-posterior gradient in the size of voltage fluctuations while in contact with atrial heart wall tissue, due to relatively greater anterior movement as a result of heart contraction. Optionally, this fluctuation gradient itself serves as another part of a frame of reference for defining positions in contact with the heart wall.

In some embodiments of the invention, apart from one or more of the various sensing modalities described herein, a position attributed to an intrabody probe 11 (including electrodes 3 thereon) in a spatial frame of reference is constrained by one or more mechanical and/or geometrical considerations (e.g., known shapes of the anatomy constraining motions of the probe). For example, the range of possible positions and/or orientations of a probe known to have entered a region of tissue from a particular entrance point (a vein, artery, or fossa, for example) is optionally restricted to just a plausible subset from all possible positions and/or orientations. Scaling and orientation may also be constrained by such mechanical and/or geometrical considerations. Mechanical constraints on probe shape may also be used in position determinations. Related geometrical and/or mechanical constraints are also discussed herein, for example in relation to FIGS. 10, 1A, and 2.

Other Modalities for Obtaining Voltage/Spatial Mapping Information

Apart from probe-measured sources, other sources of information useful for establishing and/or refining voltage/spatial mapping are available in some embodiments of the invention. It should be understood that these methods of voltage/spatial mapping can optionally be used jointly with the method of FIG. 1A, for example to provide initial maps which are refined by application of the criteria described in relation to block 112, and/or to refine a voltage/spatial mapping provided by the method of FIG. 1A. The combination of techniques can be arranged, for example, by use of a merging algorithm which provides suitable weights to various sources. These sources are now discussed with returning reference to FIG. 12.

To begin with, anatomical data 31 can be sourced from 3-D medical images of the patient, from previously performed mapping-based reconstruction (e.g., using electrical field mapping or another technique such as magnetic mapping or ultrasound mapping) and/or from anatomical atlas data. Optionally, geometrical anatomical landmarks expected from the anatomical data are identified by moving a probe 11 around until it encounters them, and registering voltages to spatial positions according to a characteristic "feature" (such as a wall of a sinus or a cavity of a vein) that is seen in a reconstruction that is formed considering limits imposed on where the probe can travel. Optionally, an overall shape of a voltage-measurement based reconstruction X is subjected to geometrical transformation T to fit the anatomy of a reference geometry Y derived from anatomical data 31. The transformation T (X)≈Y is optionally described, e.g., by the parameters of an optimal fit of an affine transformation. Additionally or alternatively, in some embodiments, the transformation is based on the mapping of corresponding landmarks in X and Y; i.e. the transformation T is found by matching landmark sets X* (which are subsets of X) in the voltage measurement-based reconstruction with corresponding geometrically located landmarks Y* to find T(X*)≈Y*.

Anatomical data can also provide simple constraints to voltage/spatial mapping, for example, by showing in what general region a heart chamber falls compared to the positions of body surface electrodes.

Optionally, anatomical data 31 may be used for constructing more detailed electric or electromagnetic field simulation data 32; for example, as described in International Patent Application No. PCT IB2016/052692, filed May 11, 2016 and entitled FIDUCIAL MARKING FOR IMAGE-ELECTROMAGNETIC FIELD REGISTRATION, the contents of which are incorporated herein by reference in their entirety. The more detailed electromagnetic field simulation data 32 are optionally used to provide a starting point to assign initial positions of intrabody-probe voltage measurements. Alternatively or additionally, the more detailed electromagnetic field simulation data 32 may be used as a post-reconstruction constraint (for example, a criterion which can optionally exclude erroneous measurement values).

Figure 7:
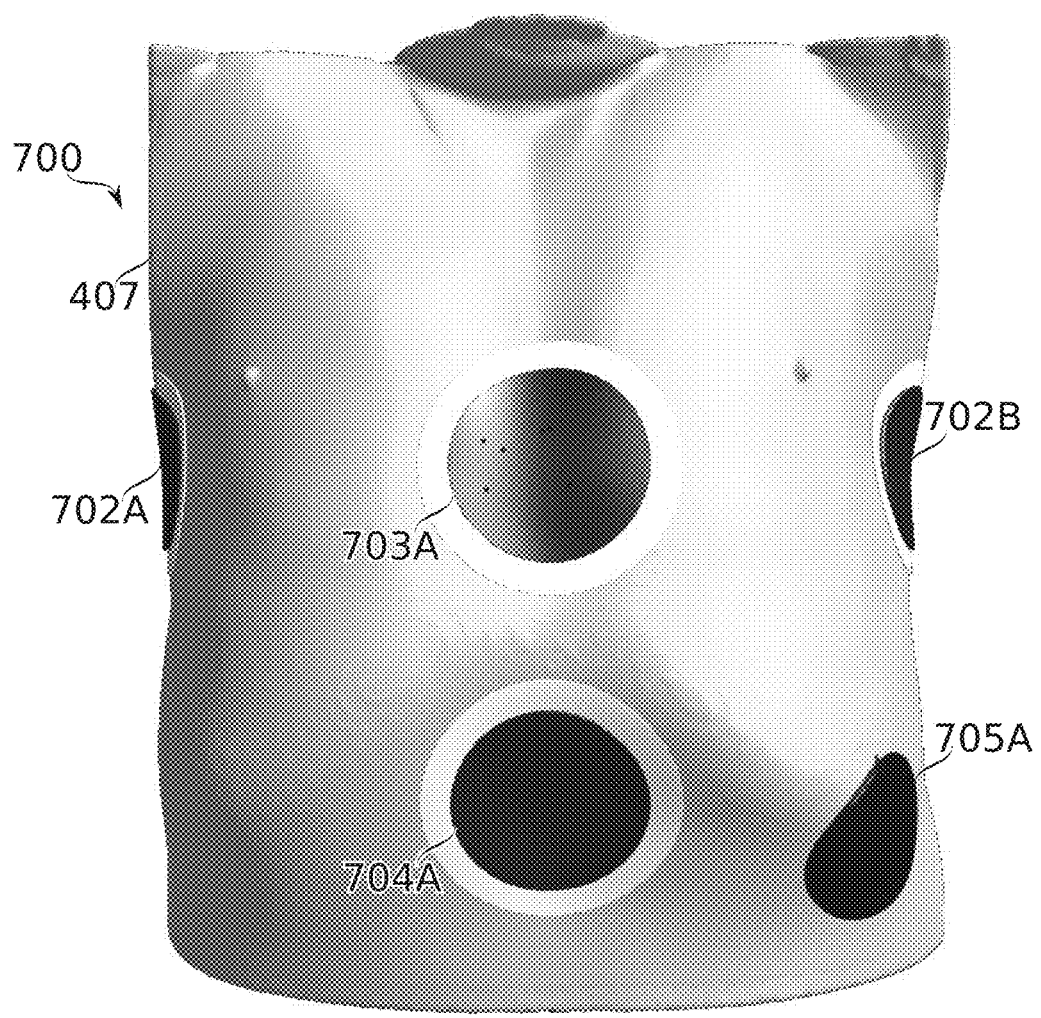
FIG. 7 schematically represents body surface electrodes, positioned on a body for generation of electromagnetic fields used in intrabody mapping and/or navigation, according to some exemplary embodiments of the present disclosure.

Reference is now made to FIG. 7, which schematically represents an electrode configuration 700 comprising body surface electrodes 702A, 702B, 703A, 704A, 705A positioned on a body 407 for generation of electromagnetic fields used in intrabody mapping and/or navigation, according to some exemplary embodiments of the present disclosure. Also, in support of the discussion of figures showing certain anatomical details herein (particularly FIGS. 7-9B), reference is now made to FIG. 4, which schematically represents coordinate systems relative to a human body 407, including an electromagnetic field-defined coordinate system 409 in the region of a heart 55, according to some exemplary embodiments of the present disclosure.

Figure 4:
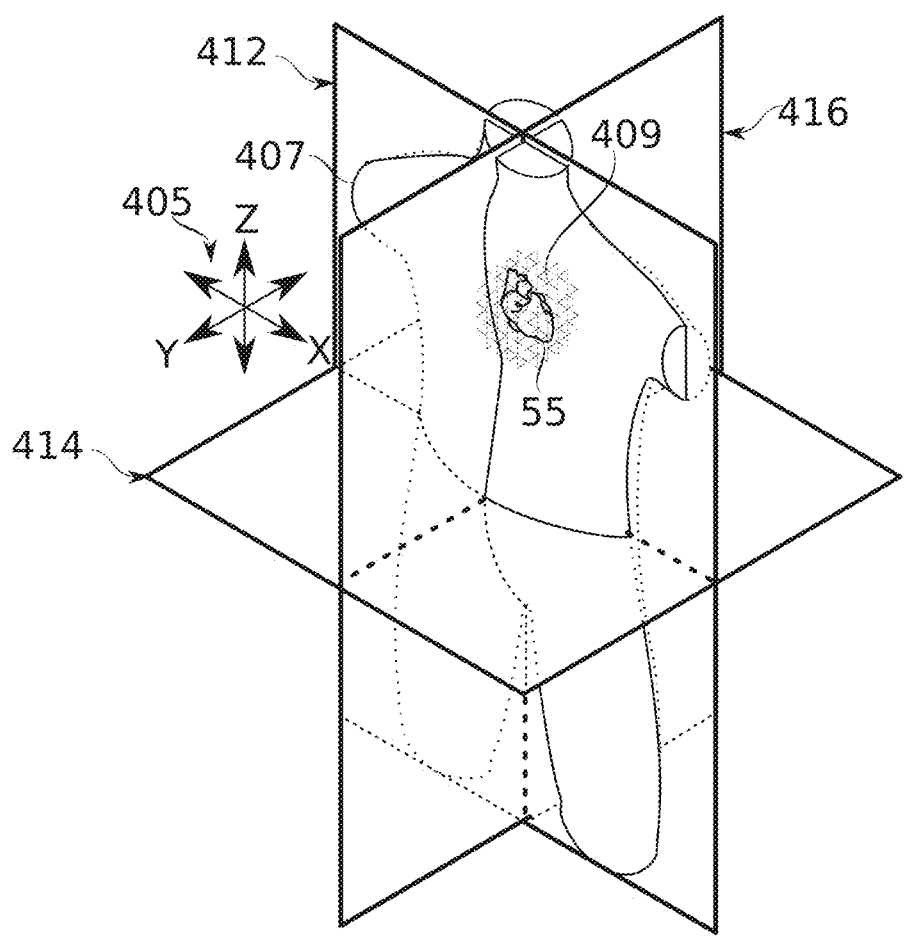
FIG. 4 schematically represents coordinate systems relative to a human body, including an electromagnetic field-defined coordinate system in the region of a heart, according to some exemplary embodiments of the present disclosure.

Shown in FIG. 4 are three cardinal planes 416, 412, and 414: a median plane 416 bisecting a body 407 into left and right portions, a coronal plane 412 bisecting body 407 into ventral (front) and dorsal (back) portions, and a transverse plane 414 bisecting body 407 into top and bottom portions. Axis indicator 405 shows a typical convention used herein for the different anatomical directions—an X axis perpendicular to the median plane, a Y axis perpendicular to the coronal plane, and a Z axis perpendicular to the transverse plane. The co-ordinate system 409 of FIG. 4 may be a "pulsing" coordinate system like that of FIGS. 3A-3C, which provides coordinates for positions within and/or around a body structure of interest during a procedure using an intrabody probe; for example, a heart 55.

Multi-Dimensional Electromagnetic Field Mapping

Figure 8A:
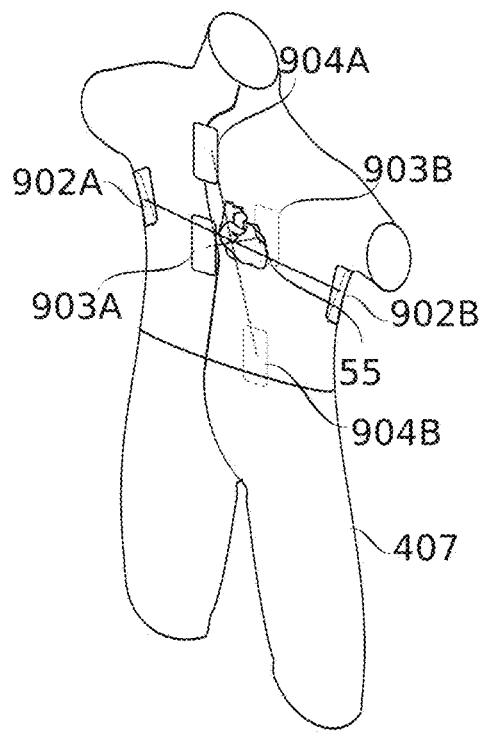
FIGS. 8A-8B schematically represent directions, of principle electromagnetic fields generated by body surface electrodes, according to some exemplary embodiments of the present disclosure.
Figure 8B:
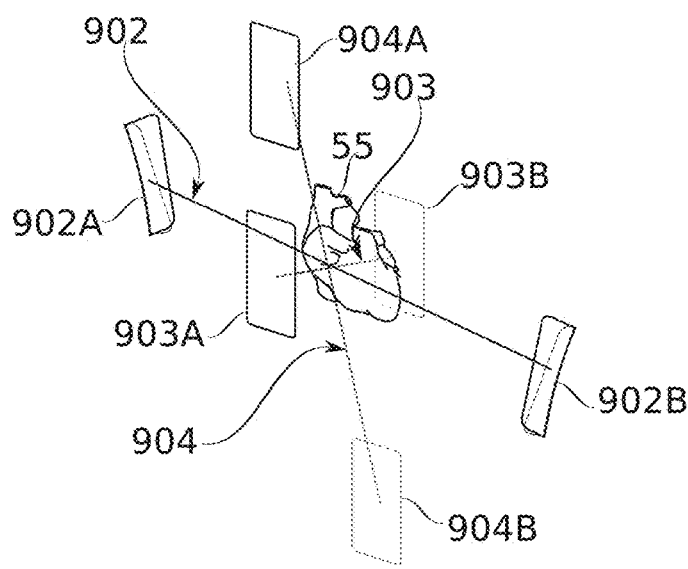

Reference is now made to FIGS. 8A-8B, which schematically represent directions 902, 903, 904 of principle electromagnetic fields generated between body surface electrodes 902A, 902B, 903A, 903B, 904A, 904B, according to some exemplary embodiments of the present disclosure.

Figure 9A:
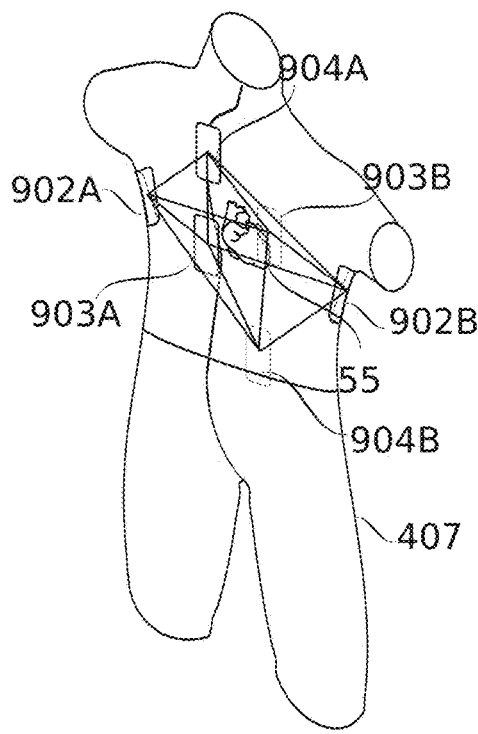
FIGS. 9A-9B schematically represent directions of several auxiliary electromagnetic fields generated by body surface electrodes, according to some exemplary embodiments of the present disclosure.
Figure 9B:
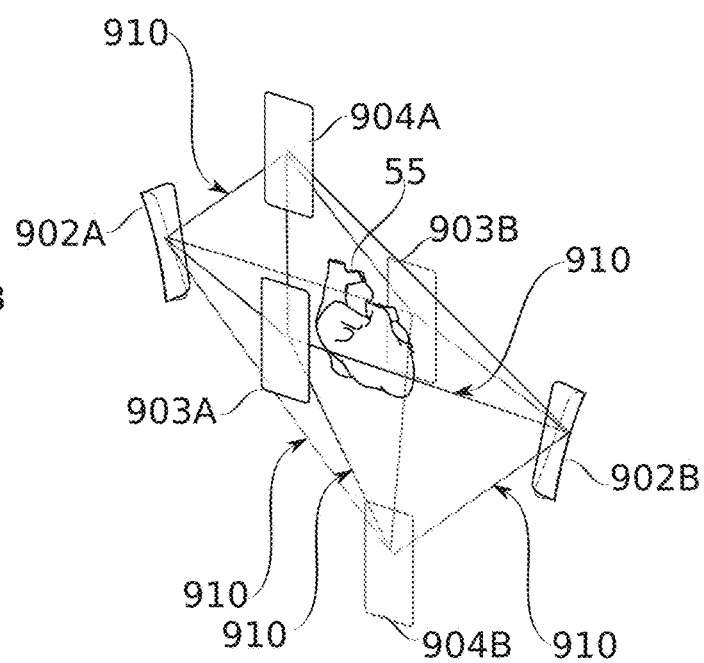

Reference is also made to FIGS. 9A-9B, which schematically represent directions of several auxiliary electromagnetic fields 910 generated between body surface electrodes 902A, 902B, 903A, 903B, 904A, 904B, according to some exemplary embodiments of the present disclosure.

The body surface electrode (or other field generator) and crossed electromagnetic field configuration of FIGS. 8A-8B represents a configuration which may be used for navigation, similar to that of FIG. 7, FIG. 8B is a magnified view of the situation of FIG. 8A, with outlines of body 407 suppressed.

In FIGS. 9A-9B, the same electrode configuration is used, but now including different electrode pairings represented by the directions of auxiliary electromagnetic fields 910. Again, FIG. 9B is a magnified view of the situation of FIG. 9A, with outlines of body 407 suppressed. Optionally, each of these auxiliary pairings is driven at a different time and/or at a different frequency. In some embodiments, analysis of voltage measurements by an intrabody probe (located for example, in the vicinity of heart 55) includes analysis for voltage (or other sensed field parameter) that varies with respect to position within the various auxiliary electromagnetic fields 910. Each such auxiliary field can thereby supply an additional dimension used in reconstruction, potentially increasing the statistical robustness of reconstruction results.

Dynamic Updating of Reconstruction During Use

Figure 1C:
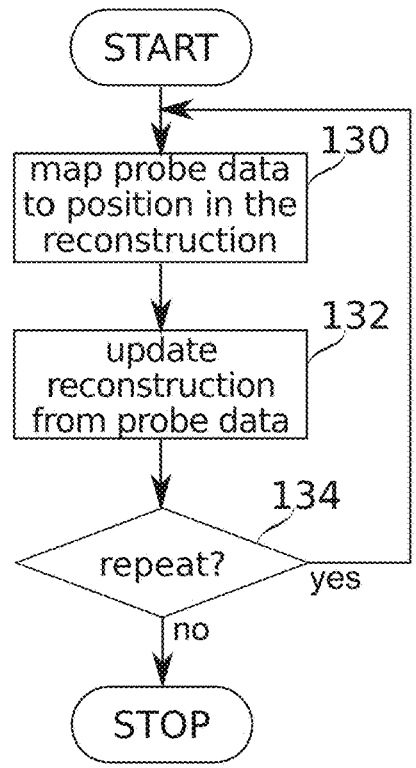
FIG. 1C is a schematic flowchart of a method for updating a body cavity reconstruction based on data from an intrabody probe, according to some exemplary embodiments of the present disclosure.

Reference is now made to FIG. 1C, which is a schematic flowchart of a method for updating a body cavity reconstruction and/or a transformation based on data from an intrabody probe, according to some exemplary embodiments of the present disclosure.

At block 130, in some embodiments, position data acquired from an intrabody probe 11 in some actual body cavity position is mapped (transformed) to a position in a spatial reconstruction of that body cavity based on an existing state of a voltage/spatial mapping, for example, a reconstruction model as described in relation to block 112 of FIG. 1A. The spatial reconstruction of the body cavity at this stage potentially includes sufficient imperfections at the position of the intrabody probe 11 as to require additional refinement before reaching the precision needed for operations of the medical procedure underway.

At block 132, the voltage/spatial mapping is updated, using the position data acquired from the intrabody probe at block 130. In some embodiments, the updated mapping comprises a weighted combination of the new position data, and data previously used in generating the existing state of the voltage/spatial mapping. Optionally, data is dropped according to age and/or if newer data is available for similar positions. Optionally or additionally, the reconstruction is formed using a weighted mixture of old and new positions. Optionally, a moving window is defined for what position data to maintain. Optionally, parts of V-cloud with no new data retain their old data, so the reconstruction can be spatially more complete. Optionally, measurement data is associated with a time stamp in this and/or other embodiments, so as to assist in selecting/using and/or dropping data according to the time of acquisition thereof. This timestamp maybe in addition to a physiological time stamp (e.g., indicating a time in a physiological cycle and/or a phase of the cycle and/or a type of the cycle, such as arrhythmic/normal for heart beats).

In some embodiments of the invention, very old data is maintained to maintain an indication of deformation of the fields caused by nearby tissue.

In some embodiments of the invention, old data is not dropped. Rather, new data is added and then the entire data set is sampled, for example, to a desired sample number and/or density.

At block 134, a decision is made to continue repeating blocks 130, 132, and 134 (i.e., the procedure continues) or not (the procedure ends). Optionally, the mapping and updating are performed at any rate suitable to the rate of data acquisition, for example, at about 0.1 Hz, 0.3 Hz, 1 Hz, 10 Hz, 15 Hz, 20 Hz, 30 Hz, 60 Hz, 100 Hz, or another reconstruction updating rate.

Figure 10:
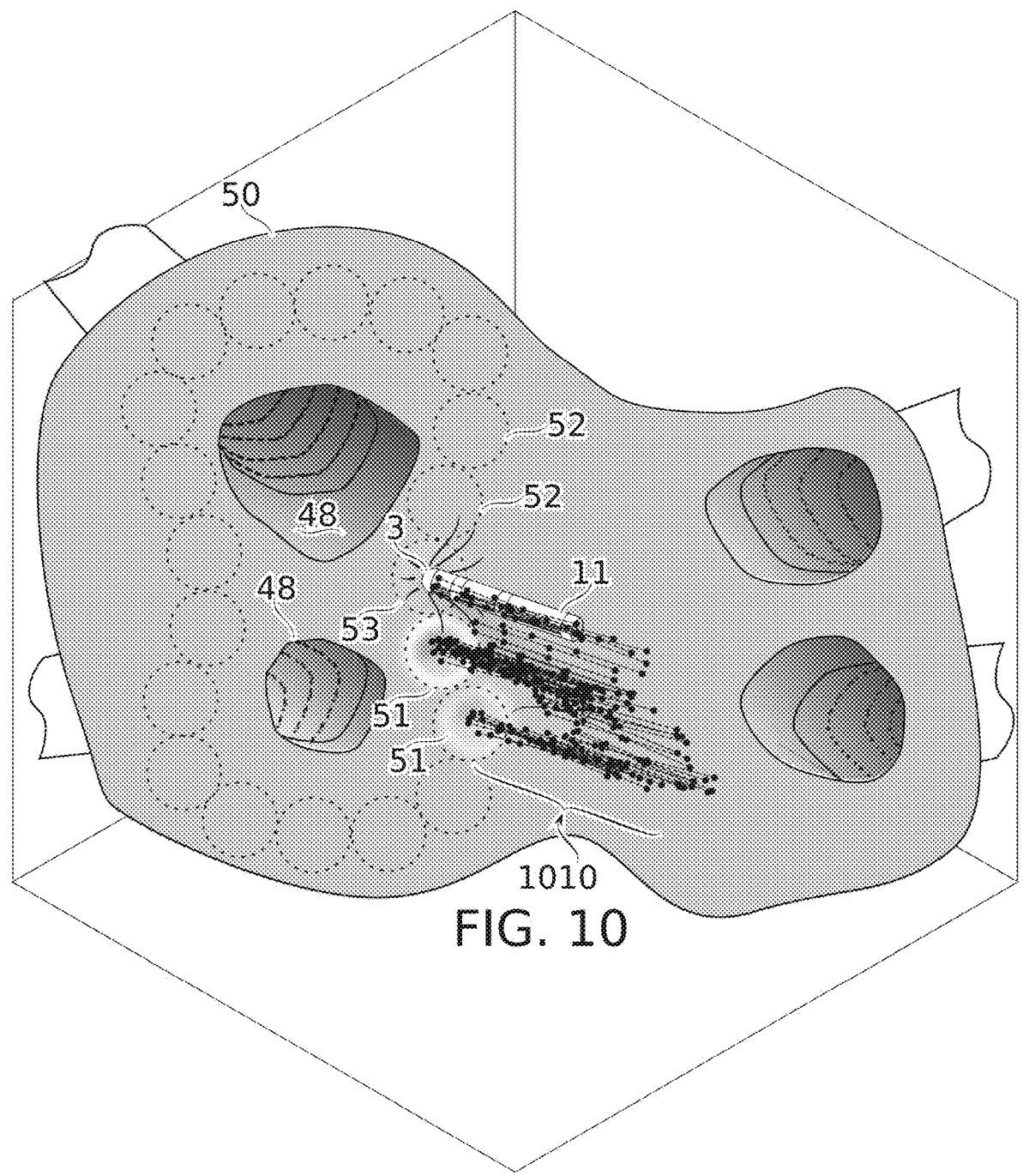
FIG. 10 schematically represents refinement and use of a body cavity reconstruction during lesioning of body cavity tissue, according to some exemplary embodiments of the present disclosure.

Reference is now made to FIG. 10, which schematically represents refinement and use of a of a body cavity reconstruction during lesioning of body cavity tissue, according to some exemplary embodiments of the present disclosure.

In some embodiments, a goal of ablation procedures to treat atrial fibrillation, is to electrically isolate regions of cardiovascular tissue involved in triggering fibrillation episodes from the main body of the heart. In some embodiments, the plan for achieving this goal comprises forming an ablation line in the heart wall comprising a chained-together sequence of smaller lesions. In FIG. 10, circles 52 indicate planned positions for lesions in a left atrial wall tissue 50, in order to isolate electrogenic sources in one or more pulmonary veins 48. Two already placed lesions 51 are shown, as well as a partial lesion 53 in the process of ablation. The relative positioning of placed lesions 51 following the ablation plan can have a significant impact on the prognosis for success, since gaps between the smaller lesions 51 can allow electrical reconnection, and failure of the treatment as a possible result.

In some embodiments of the invention, continual updating of a body cavity reconstruction based on voltage measurement readings from the ablation probe 11 itself as it moves around the heart helps to increase the resolution, precision, and/or accuracy of the body cavity reconstruction at the places where the activity (and, potentially, interest and/or importance to the procedure) is also increased. Moreover, insofar as correct relative placement of the small lesions is a significant factor in procedure success, it is a potential advantage to include recent, nearby position data in the reconstruction which is used to guide subsequent positioning. For example, in some embodiments, locations of already made lesions may be marked on a view of the reconstruction model, e.g., as colored circles of a size indicative of the lesion size. Cloud 1010 represents just the locations, to which the most recent voltage measurements have been transformed during the ongoing formation of an ablation line. The sampling density shown is reduced for purposes of illustration. Voltage measurements are optionally taken at a relatively high frequency compared to the size and motions of the probe, so the spatial sampling interval during careful positioning movements is usually less than about 10% of the probe diameter. For example, a sampling rate of about 100 measurements per second while moving a 1 mm diameter probe about 10 mm per second would result in a measurement every 100 µm). As a result, there will usually be a substantial number of neighboring-position voltage measurements available for use in determining a current ablation probe position in relation to recent ablations.

The creation of small lesions typically requires several seconds of fixed positioning of an ablation probe, so that there is also ample time to acquire phasic information, for example as described in relation to FIGS. 5A-5E. This phasic information can be used in different ways to assist positioning during a procedure, as is now described.

In some embodiments of the current invention, there is a tradeoff, when displaying an intrabody probe position within a heart chamber reconstruction model, between showing phasic motions of the heart and/or probe ("phasic fidelity" in the discussion that follows), and suppressing those motions ("phasic stabilization"). Optionally, actual phasic motions are displayed (insofar as available information allows), with full phasic fidelity, full phasic stability, or some intermediate combination of the two.

Greater phasic fidelity has the potential advantage of making it clearer to an operator what control motions of the intrabody probe (e.g., catheter manipulations) are actually possible, and what their effects are likely to be. For example, as a probe approaches a heart wall, it can intermittently fall in and out of contact with beating tissue. Seeing this clearly represented can help to guide an operator to determine whether more advance is needed to reach the tissue wall before beginning a treatment. Displaying with greater phasic stabilization, on the other hand, has the potential advantage of removing distracting motions from the view of the operator, to facilitate concentration on identifying and reaching a target position.

In some embodiments of the invention, stabilization of/fidelity to phasic motions is divided according to different types of phasic motion. Phasic motion which identically affects both an intrabody probe and the cavity in which it is positioned (e.g., a rigid translation component of phasic motion) will often be of little interest to an operator, since the relative positions of the two remain unchanged by such motion. In some embodiments, this component is preferably suppressed for the operator (e.g., the motion is not reproduced on a view provided to the operator that shows a position of the probe within a reconstruction).

In many situations, beating of a heart results in repeated expansions and contractions that change the relative position of heart wall and intrabody probe. In some embodiments, the heart wall is shown in a substantially fixed position (at least, within the duration of one heartbeat), and the probe is shown to move. Display of this kind of relative motion would be a typical result if phasic changes in electromagnetic field and/or cavity geometry were not specifically accounted for. However, the resulting apparent motion is not only potentially rather artificial-seeming, but it can also be distracting to an operator trying to reach a specific target.

In some embodiments, an optional display mode having greater phasic fidelity represents relative motions due tissue movement as displayed tissue movement, while the probe itself remains relatively stationary in the display. This motion is optionally approximated based in partial data, and does not need to be rendered with best available accuracy to be useful. For example, the whole heart is optionally moved according to a stereotyped phasic pattern with only a small number of parameters being determined from current measurements. This approach could be used to maintain an accurate representation of distance between the tip of an intrabody probe and the tissue it is nearest to, while other phasic movements are represented as suggestive of actual ongoing motion, without necessarily being as accurate.

In some embodiments of the invention, phasic relative probe/tissue motion is optionally divided into both a component due to phasic motion of the tissue, and a component due to phasic motion of the probe because it is disturbed by motion of the tissue. Optionally, separating of these motions is performed (statistically, for example) by comparing changes in the measured environment of the probe 11 when in contact and when not in contact with the tissue wall, for a particular region. Measured out-of-contact motion not accounted for by measured in-contact motion is optionally assigned to be "probe motion". Additionally or alternatively, phasic motions of the probe as such are accounted for based on physical analysis of the motion of anchoring anatomy of the intrabody probe 11 (e.g., movements of fossae and/or vascular roots by which a probe 11 enters a heart). Optionally, such analysis taking into account the extent by which a distal end of the intrabody probe has passed such an anchoring region.

In some embodiments, display of both phasic tissue motion and phasic probe motion are suppressed (phasic stabilization), insofar as some metric of relative position can also be stabilized. For example, displayed distances between a probe 11 and heart wall tissue 50 are optionally displayed relative to some particular phase of the heartbeat cycle. Optionally, for example, when the actual probe position extends past the displayed position of the tissue wall it is near, the displayed probe position is nevertheless maintained at the position of the wall. Optionally, there is some other displayed indication of increased advance of the probe toward the wall, such as distortion of the contacted wall region as if it is experiencing increased force of contact.

Phasic stabilization and phasic fidelity are optionally intermingled, in some embodiments. For example, display of phasic motion of body tissue is substantially suppressed in some embodiments as just described (e.g., walls of a heart chamber are displayed not beating). However, where probe 11 experiences intermittent contacts and/or forces due to phasic motion, a constant or a phase-varying indication (e.g., distortion of tissue or probe) at a region of tissue contact is optionally displayed to indicate this. This indication does not necessarily indicate the phasic motion over the whole displayed representation of the structure undergoing phasic motion.

It should also be noted that phasic intra-beat changes in heart size due to heart beat are optionally treated distinctly from beat-to-beat changes in displayed heart size due to changes in heart rate, for example as described herein in relation to FIGS. 5A-5D.

Inputs and Functions of a Reconstruction Service Module

Figure 11:
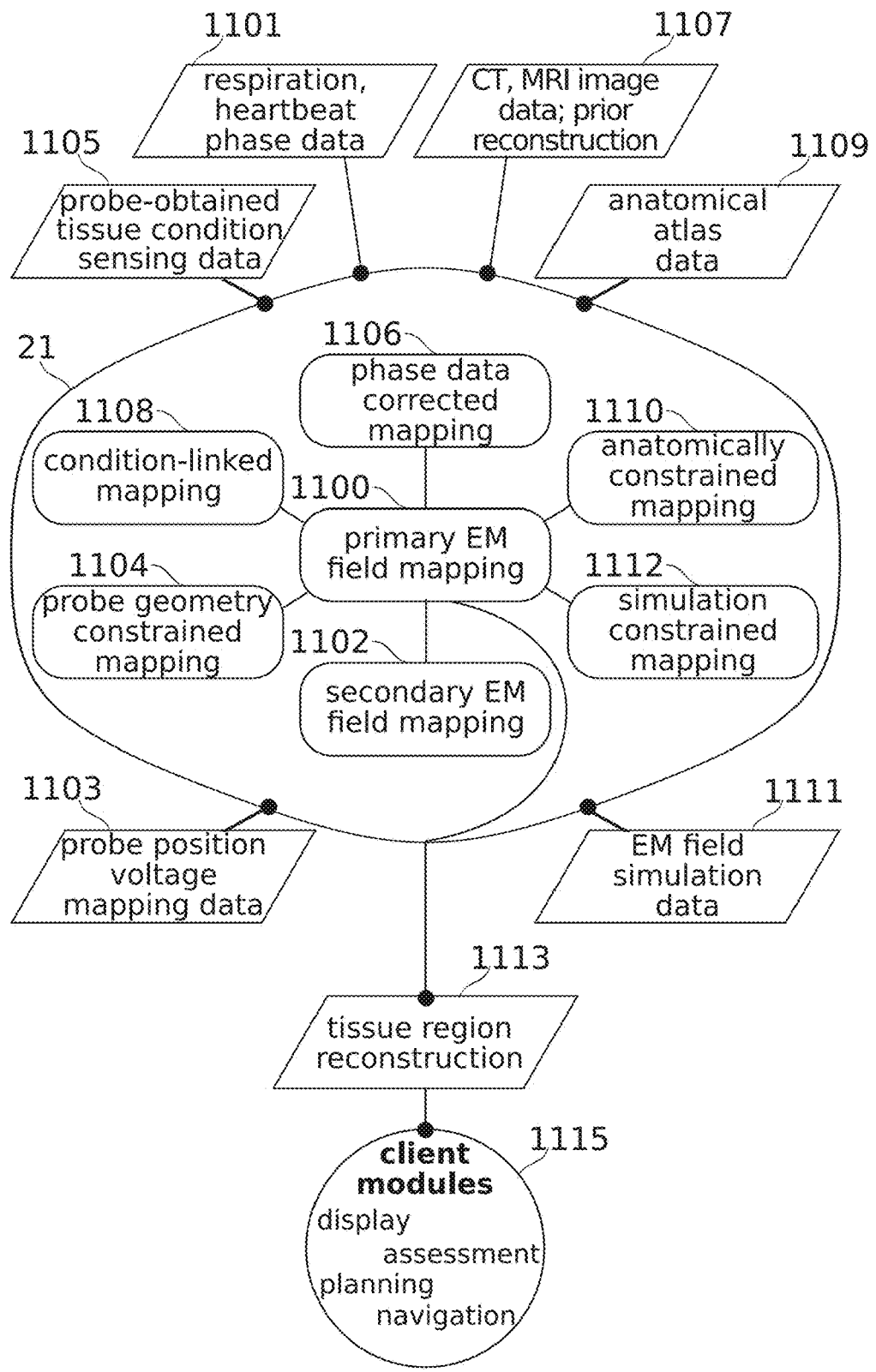
FIG. 11 schematically represents inputs to and functions performed by a reconstruction service module, according to some exemplary embodiments of the present disclosure.

Reference is now made to FIG. 11, which schematically represents inputs to and functions performed by a reconstruction service module 21, according to some exemplary embodiments of the present disclosure.

FIG. 11 collects together functions of reconstruction service module 21 provided in some embodiments of the current invention, and described in relation to the other figures herein, for example as indicated below. Not all functions are provided in every embodiment of the current invention; rather they are optionally provided in any suitable combination of available input and reconstruction-supporting functions described herein. In some embodiments, reconstruction service module 21 is implemented as computer code, optionally in conjunction with digital signal processing (DSP) and/or graphical processing hardware specialized for signal and/or image processing. Implementation is optionally within a single computing device, or distributed among a plurality of computing devices. Each of the functionality blocks 1102, 1104, 1106, 1108, 1110, and 1112 shown within reconstruction service module 21 represents a different contribution to primary (i.e., "overall") EM mapping functionality 1100. Any of these functionality blocks is optionally provided by reconstruction service module 21. Each of functionality blocks 1102, 1104, 1106, 1108, 1110, and 1112 may be understood as contributing to the primary EM field mapping functionality 1100 according to their own specific capabilities. Optionally, contribution to mapping is by any suitable combination of the operations of functionality blocks 1102, 1104, 1106, 1108, 1110, and 1112.

Basic input for reconstruction, in some embodiments, comprises probe position voltage mapping data 1103, which may include, for example, data indicative of voltage measurements made by various electrodes on the probe, where each measurement is associated with an identifier of the electrode that made the measurement, and the frequency at which the measurement was made. The probe position voltage mapping data 1103 optionally are provided with respect to at least three crossed electromagnetic fields, and optionally with respect to any number of electromagnetic fields (for example, as described in relation to FIGS. 8A-8B and 9A-9B).

In some embodiments, and using position voltage mapping data 1103, the probe geometry constrained mapping functionality block 1104 produces a voltage/spatial mapping, for example as detailed in relation to block 112 of FIG. 1A. Optionally, this is performed in conjunction with one or more spatial coherence criteria. In some embodiments, this voltage/spatial mapping serves as a base mapping which the other functionality blocks 1102, 1106, 1108, 1110, and 1112 optionally act upon and modify (as further explained herein below).

As output, reconstruction service module 21 produces a tissue region reconstruction 1113. Reconstruction 1113 in turn is optionally used by one or more client modules 1115. Use of the tissue region reconstruction is detailed, for example, in relation to block 114 of FIG. 1A. Client modules 1115 can be any hardware or software implementation of functionality described in relation to block 114, such as the functionality of display and/or navigation, procedure assessment, procedure planning and/or replanning, or another functionality.

Modifications produced by the remaining functionality blocks 1102, 1106, 1108, 1110, and 1112 are now described in turn.

Optionally, where more than three (for example, four, six, eight, ten or intermediate or to larger number of fields) primary electromagnetic fields are used in generating probe position voltage mapping data 1103, reconstruction service module 21 implements electromagnetic field mapping 1102, using "extra" fields. These can be electrical fields generated using body surface electrodes, for example as described in relation to FIGS. 8A-8B and 9A-9B; using electrodes on other intrabody probes besides that used to sense probe position voltage mapping data 1103; and/or using electrodes on the same probe used for sensing.

Optional first auxiliary inputs 1107 used in some embodiments of the invention may include CT, and/or MRI image data and/or reconstruction data (such as probe position voltage mapping data) obtained from the patient during an earlier procedure, or earlier in the present procedure. Additionally or alternatively, a second set of auxiliary input may include anatomical atlas data 1109. Auxiliary inputs 1107 and 1109 correspond, in some embodiments, to the anatomical data 31 of FIG. 12. Optionally, these auxiliary inputs are used by functions of anatomically constrained mapping functionality block 1110 in reconstruction service module 21. The anatomically constrained mapping functionality block 1110 optionally uses one or more of the auxiliary data inputs 1107, 1109 to help scale and/or orient the tissue region reconstruction 1113. Optionally, one or more of auxiliary inputs 1107, 1109 is used to help identify position sensing errors—for example, a sensed position located in a place that is determined to be not physically accessible may be disregarded in producing tissue region reconstruction 1113.

Optionally, electromagnetic (or just an electrical component) field simulation data 1111 are provided (corresponding, in some embodiments, to electromagnetic field simulation data 32) for use by functions of simulation constrained mapping 1112 in reconstruction service module 21. The electromagnetic field simulation data 1111 is optionally based in turn on one or both of auxiliary input data 1107, and/or 1109. Electromagnetic field simulation is described, for example, in relation to FIG. 7 herein.

Optionally, tissue region reconstruction 1113 includes correction for phases of heartbeat and/or respiration, based on respiration and/or heartbeat data 1101 according to processing by functionality of reconstruction service module 21 for phase data corrected mapping 1106. This is described, for example, in relation to FIGS. 3A-3C and 5A-5E herein.

Optionally, tissue region reconstruction 1113 is generated and/or refined based on probe-measured tissue condition sensing data 1105, as processed, for example, by functionalities of reconstruction service module 21 for condition-linked mapping 1108. This is described, for example, in relation to FIG. 6, herein.

Cost-Function Driven Determination of a V-Cloud to R-Cloud Transform

Figure 13:
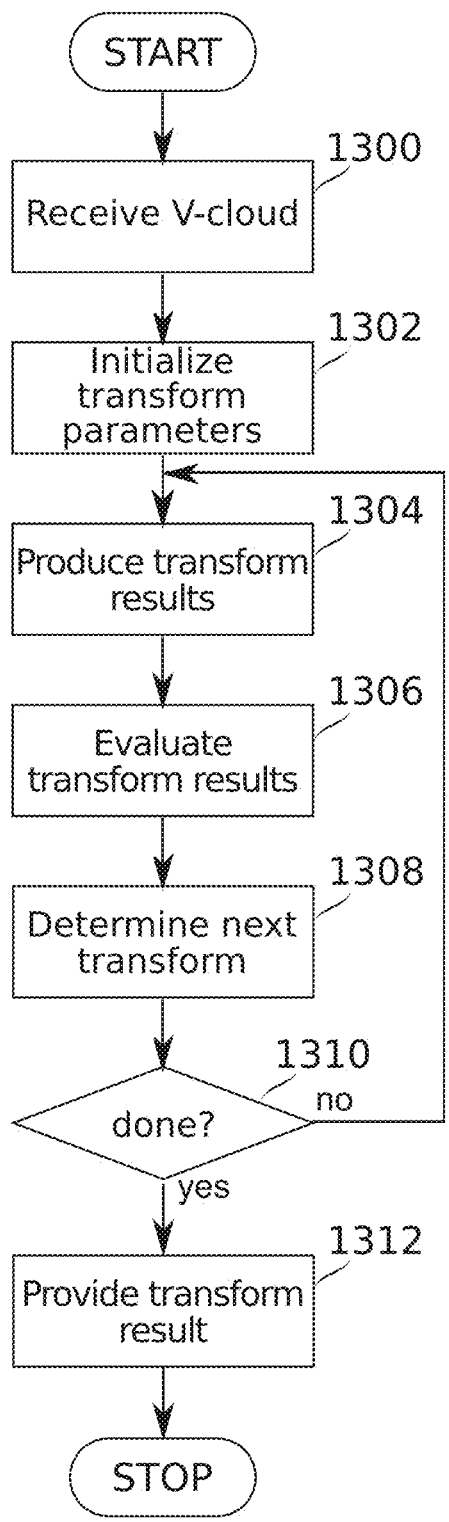
FIG. 13 is a flowchart schematically illustrating a method of transforming a V-cloud to an R-cloud, according to some embodiments of the present disclosure.

Reference is now made to FIG. 13, which is a flowchart schematically illustrating a method of transforming a V-cloud to an R-cloud, according to some embodiments of the present disclosure. The blocks of the flowchart should be understood as indicating principles behind how the transformation method operates; however, the order in which operations described is actually performed potentially differs, e.g., terms described sequentially are optionally calculated substantially simultaneously.

At block 1300, in some embodiments the V-cloud is received. The V-cloud optionally includes a multiplicity of measurement sets. In some embodiments, each measurement set comprises a sub-group of electrical field measurements which will be treated as space-like, in the sense that changes in electrical field measurements (e.g., in mV) along each of the three space-like V-cloud axes correspond roughly to changes in position due to movements of the probe (e.g., in mm) along a spatial dimension. The correspondence is optionally inexact, e.g., comprising significant non-linearities in distance and/or direction; however it optionally serves to form a basis on which corrections (displacements) can be superimposed.

In some embodiments, receiving the V-cloud may also include pre-processing it, for example: shifting all voltage readings to spread around some value (e.g., 0, optionally the readings are spread equally around that value); normalizing the voltage readings, e.g., by dividing by the standard deviation of all the measurements; and/or whitening, as described above.

At block 1302, in some embodiments, initial transformation parameters are determined. In some embodiments, the transformation to be determined divides into two terms: one term which simply scales the "space-like" V-cloud measurements of each set, and another constructed so as to use the intrinsic geometry of the V-cloud measurements impose corrections on the "space-like" V-cloud term in the form of displacements.

In some embodiments, the parameter determining a global transformation of the "space-like" V-cloud term is provided as a vector coefficient a, applicable to generate a simplified transformation of "space-like" V-cloud representation X into an R-cloud Y according to the equation Y=diag(a)X. Each of X and Y optionally comprises a 3×N matrix: three spatial (or space-like) dimensions wide by N measurements long. The components $(a_x, a_y, a_z)$, of vector coefficient a serve to separately scale each of the three "space-like" V-cloud measurement axes, which together comprise each measurement set of the matrix X. The units of these components are, e.g., in mm/mV in embodiments wherein the measurements of X are expressed in mV.

Optionally, initial values for the components of a are chosen arbitrarily, e.g., all set to 1 mm/mV. Optionally, they are selected so that each of the principle dimensional directions in Y is about the same size (e.g., selected to make the R-cloud as "spherical" as the data allow). In some embodiments, task specific data, such a general shape of an organ imaged and/or probe insertion direction, may be used to suggest a different original shape.

In some embodiments, the term that expresses displacement adjustments to be "superimposed" on the term diag (a)X is expressed as UW'. In some embodiments, U is a matrix representing eigenvectors of a kernel of X, this time a k×N matrix, where k is the total number of eigenvectors used (e.g., up to N, optionally fewer). Thus, U may be understood as expressing the V-cloud in its "natural" representation, each of its eigenvectors representing a different, linearly independent feature.

In some embodiments, the remaining matrix coefficient W' is a 3×k matrix that multiplies with k×N eigenvector 'matrix U to provide a new 3×N matrix that describes spatial displacements that are additive (in some embodiments) with the diag(a)X term to provide the full transformation (for a given a and W'): Y=diag(a)X+UW'. Roughly, W' may be understood as encoding how the various features of X re-encoded in U should be weighted in order to improve the expected resemblance of diag(a)X to the actual positions at which measurements were taken.

Optionally, the initial value of W' is, for example, the zero matrix.

At block 1304, in some embodiments, current (initial, or as later adjusted) transformation results are produced: that is, diag(a)X+UW' is evaluated to obtain a current estimate of Y.

Figure 14:
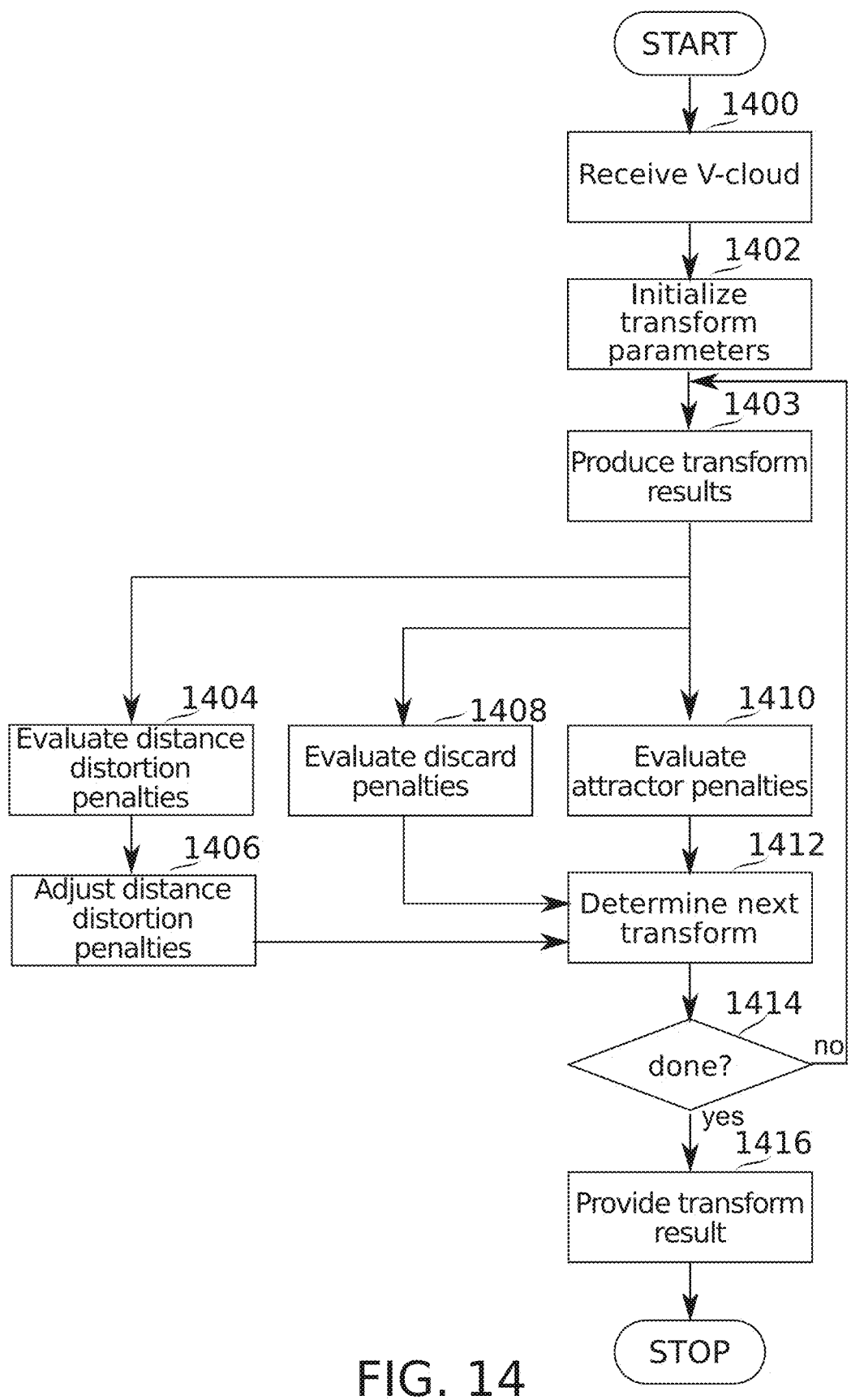
FIG. 14 is a flowchart schematically representing a method of reducing the effect of outlier measurements on a V-cloud to R-cloud transformation, according to some embodiments of the present disclosure.

At block 1306, in some embodiments, the current transformation results are evaluated for how well they meet target criteria used for judging the quality of a transformation. In some embodiments, these target criteria are judged by calculating one or more penalty terms (of a cost function), and then summing all the penalty term calculations together into a single cost. The choice of particular penalty terms includes, in some embodiments one or more of:

- A distance distortion penalty for inter-electrode distances (e.g., distances between sister electrodes for sister measurements) in currently estimated Y which do not match distances known, e.g., from the electrode spacing on a measurement probe that carries them.
- An incoherence penalty for a "lack of smoothness" (coherence) in Y: for example, larger displacements along high spatial frequency components of U indicate, in some embodiments, that less coherence is maintained in the transformation into Y.
- Penalties related to outlier detection/mitigation, for example as described in relation to FIG. 14.

At block 1308, in some embodiments, the evaluation of block 1306 is used to determine what transformation parameters to evaluate next. In some embodiments, this determination comprises making an incremental adjustment to the transformation parameters (e.g., a and W'), guided by the goal of generating new transformation parameters that transform X into a new R-cloud Y which evaluates to have a lower cost than the current result. The details of this are different for different optimization algorithm embodiments, of which several are known in general in the field of optimization. In overview, however: if the evaluation of block 1306 results in a higher cost than some previous evaluation (e.g., the most recent one), then the transformation parameters (e.g., a and W') are considered to have been recently adjusted in "the wrong direction". The next parameter adjustment may, for example, reverse this change, try adjusting a different parameter, and/or adjust in an opposite direction.

At block 1310, in some embodiments, a determination is made as to whether the penalty-minimizing search has reached a termination condition (e.g., a condition where reduction in penalty among search iterations is below some threshold). If not, the flowchart returns to block 1304, wherein the V-cloud to R-cloud transformation is now the newly selected transformation. If the termination condition is met, the flowchart concludes with block 1312.

At block 1312, in some embodiments, a last R-cloud transformation result is produced (and provided as output), based on the current transformation.

Adding New Data

Using standard techniques, the decomposition calculation that determines U (for example as described in the section entitled Local spatial position constraints on reconstruction) is computationally expensive. When new measurement data is acquired, it is a potential advantage to avoid the necessity to perform the entire decomposition each time, for example, in order to allow faster updating of the reconstruction results.

In some embodiments, recalculation of the decomposition is performed based on the following, given new measurements $\hat{X}$ after already having obtained a component decomposition U using older measurements X:

The new kernel $\hat{K}$ is:

$$\hat{K} = K\left(\hat{X}_i, X_j\right)$$

The normalization matrix $\hat{S}$ is: $\text{diag}(\hat{K}\mathbb{1})$

The new decomposition $\hat{U}$ is: $\hat{U} = \hat{S}^{1/2}\hat{K}\hat{S}^{-1/2}UV^{-1}$ And the equation for which a and W' are to be optimized is:

$\hat{Y} = \hat{X}\,\text{diag}(a) + \hat{U}W'$

Outlier Removal

Reference is now made to FIG. 14, which is a flowchart schematically representing a method of reducing the effect of outlier measurements on a V-cloud to R-cloud transformation, according to some embodiments of the present disclosure.

In some embodiments, an outlier-adjusted distance distortion penalty term is used to help identify outlier measurements. Optionally, the outlier-adjusted distance distortion penalty term comprises an outlier identifier $\alpha_{ij}$, which assumes a value 0 for an outlier and 1 for an inlier. In some embodiments, the values are different, but distinguish between an inlier and an outlier.

When the value is 0, the distance is treated as involving an outlier measurement; when the to value is 1, the distance (and so, the measurements that define it, unless it is part of another outlier pair) is considered valid. In some embodiments, the outlier identifier is a number changing continuously between 0 and 1. Optionally, to avoid "intermediate validity" of a distance for values other than 0 and 1, the intermediate values are further penalized, for example as described below. A distance which is finally assigned α=0 ceases to contribute a distance distortion penalty (a distance distortion penalty is a penalty depending on the difference between the sister distance and the physical distance between the electrodes producing it, i.e., a corresponding desired sister distance). For example, by multiplying the distance distortion penalty associated with each electrode pair by the outlier identifier of that pair, outliers don't have any effect on the cost-function term that depends on the distance distortion penalty. Thus, if all the pairs are considered outliers, this term of the cost function zeroes. To prevent that, another term may be added, which provides a penalty for every pair identified as an outlier (discard penalty term). This way, the number of outliers will be minimized because of the discard penalty term, and only pairs having exceptionally large contribution to the distance-distortion penalty are defined as outliers.

It should be emphasized that each $\alpha_{ij}$ is defined per distance, rather than per measurement, in this method. Each measurement of a pair that has a known inter-electrode distance thus is optionally associated with a certain corresponding $\alpha_{ij}$. Since a measurement may be part of the determination of more than one known inter-electrode distance, it may also be associated with more than one $\alpha_{ij}$.

All the a outlier identifiers are optionally available for modification by the cost function-minimizing process. Optionally, the penalty function-minimizing process is able to vary each α through a range of values between 0 and 1. To prevent the process from just tending to reach α=0 for all distances, a complementary penalty term is introduced. The complementary penalty term may, for example increase as α→0, and/or depending on counts of outliers.

In some embodiments, the discard penalty term is calculated for and applied to all sister distances and their defining sister measurements equivalently, without necessarily distinguishing which sister measurement is "responsible" for the distance error. For example, the discard penalty may comprise an optionally constant-scaled sum over (i,j) of $1-\alpha_{ij}$; that is:

$$P_{discard} = \lambda \sum_{i,j} 1 - \alpha_{ij}$$

The scaling constant λ is optionally selected so that the discard penalty balances reduction in the distance distortion penalty so that a preponderance (e.g., at least 95%) of measurements are retained. A larger λ results in fewer measurements being identified as outliers.

In some embodiments, to make sure α is attracted to either 0 or 1 for each distance, another penalty term is introduced (an "attractor penalty"), for example, an appropriately scaled Gaussian or sine function peaking at α=0.5 and approaching 0 as α→0 or α→1. Optionally, α starts at a value of 0.5, and is adjusted gradually upward or downward for each distance during penalty minimization.

FIG. 14 corresponds, in some embodiments, to the outlier-discarding method just described. FIG. 14 is consistent with a simple gradient descent method of penalty minimization; however it should be understood that there are many general optimization methods available for a cost function-driven search of a parameter space for a penalty-minimizing solution, and that the specific method of FIG. 14 is illustrative of any of these methods with changes as necessary. The blocks of the flowchart should be understood as indicating principles behind how the transformation method operates; however, the order in which operations described is actually performed potentially differs, e.g., terms described sequentially are optionally calculated substantially simultaneously.

At block 1400, in some embodiments measurements of the V-cloud are received.

At block 1402, in some embodiments, initial a values are set for all distances in the R-cloud, e.g., α=0.5. Other parameters (e.g., of those affecting other penalty terms for each V-cloud to R-cloud transformation) are optionally also initialized at the same time.

At block 1403, in some embodiments, current (initial, or as later adjusted) transformation results are produced. For example, diag(a)X+UW' is evaluated to obtain a current estimate of Y.

At block 1404, in some embodiments, the distance distortion penalty terms for distances in Y (or in other related or derived constructs) are calculated.

At block 1406, in some embodiments, the distance distortion penalties are multiplied by the current value of α for each term to create an adjust distance distortion penalty. As α decreases for some distance, its adjusted distance distortion penalty also decreases.

At block 1408, in some embodiments, the discard penalties are calculated, for example by the operations represented by the equation:

$$P_{discard} = \lambda \sum_{i,j} 1 - \alpha_{ij}$$

and/or other operations.

At block 1410, in some embodiments, attractor penalties (costs) for each α are calculated, e.g., using penalty terms in a form such as a sine wave or Gaussian that tends to minimize the attractor penalty as α approaches 0 or 1, and increase it for values in-between.

At block 1412, in some embodiments, the resulting penalty value for the V-cloud to R-cloud transformation is used, according to the specifics of the particular penalty-minimizing algorithm implemented, to select (e.g., by adjustment of parameters of the current transformation) a new transformation for evaluation. The resulting penalty value includes at least the outlier-adjusted distance distortion penalty term, the discard penalty term, and the attractor penalty (if applicable).

In some embodiments, this determination comprises making an incremental adjustment to the transformation parameters (e.g., a, W', and W), guided by the goal of generating new transformation parameters that transform X into a new R-cloud Y which evaluates to have a lower cost than the current result. The details of this are different for different optimization algorithm embodiments, of which several are known in the art of optimization. In overview, however: if the evaluation of block 1410 results in a higher cost than some previous evaluation (e.g., the most recent one), then the transformation parameters (e.g., W', and α) are considered to have been recently adjusted "too much" and/or in "the wrong direction". The next parameter adjustment may, for example, reverse or reduce this change, try adjusting a different parameter, and/or adjust in an opposite direction.

At block 1414, in some embodiments, a determination is made as to whether the penalty-minimizing search has reached a termination condition (e.g., a condition where reduction in penalty among search iterations is below some threshold or otherwise defined criterion). If not, the flowchart returns to block 1404, wherein the V-cloud to R-cloud transformation is now the newly selected transformation. If the termination condition is met, the flowchart concludes with block 1416.

At block 1416, in some embodiments, a last R-cloud transformation result is produced (and provided as output), based on the current transformation. This method optionally prevents (or reduces) outliers from being considered in identifying a transformation from V-cloud to R-cloud, and thus may significantly reduce total computation time and distortions of the transformation due to the outliers. However, this method does not necessarily discard any point from the V-cloud or the R-cloud; although outliers may optionally be discarded from the R-cloud based on the outlier determinations just described.

SUMMARY OF SOME INVENTIVE CONCEPTS

In view of the large amounts of detail, it may be appropriate to summarize some of the inventive concepts described above.

In the context of reconstructing a body cavity shape of a subject, the present disclosure provides for displaying a model of the body cavity shape based on analysis of intrabody measurements of crossing electromagnetic fields established within the body cavity. The measurements of the crossing electromagnetic fields may be received by a computer circuitry, which may also be used for determining positions at which the measurements were taken. The measurements are carried out using at least two sensors carried on an intrabody probe with the probe at multiple locations in the body cavity.

The model may be generated from a cloud of electrode positions, at which the measurement were taken, in a manner used in the art for obtaining an outer shell from a point cloud, e.g., using a ball pivoting algorithm. A main potential contribution of some embodiments in the disclosure is in providing ways for reconstructing the positions at which the measurements were taken (also referred to herein as R-cloud) from the measurements themselves and their interrelationships. It is noted that in some embodiments these measurement positions may only be meaningful and/or have a useful precision (e.g., better than 3 cm) as positions with respect to other measurement positions or with respect to an image or other 3D reconstruction which includes such measurement positions. In some embodiments, electrode positions as such are not recovered. Alternatively or additionally, a 3D model is reconstructed which also includes therein positions of a probe while such measurements were taken. In one example, an image of a portion of the heart including an indication of a catheter (or other object) position therein, are reconstructed as a single unit. In another example, such an image of a portion of the heart is reconstructed and a position (and/or orientation) of the catheter with respect to that image is reconstructed.

It is to be noted that positions determined according to some embodiments of the present disclosure are not necessarily the exact positions at which the measurements were taken. In fact, the inventors found evidence to the existence of some electrode positions where no measurements were taken, for example, reconstruction of structural detail that the probe didn't visit. However, the reconstructed positions provide a good approximation to the structure of the body part. In fact, this appears to be the best approximation known to the inventors to be achieved from intrabody measurements.

A unique feature of a reconstruction obtained according to some embodiments of the present disclosure is that the positions are determined one in relation to the other, so that no imposed/external frame of reference is required. Thus, the determination of the R-cloud is based on analysis of distances between determined electrode positions, and is independent of other measurements or knowledge of locations and/or orientation of any object outside the body cavity. In some embodiments, the method does not rely on knowledge of a distance and/or orientation to an external reference object, an orientation of an external reference object, or the like. Therefore, in some embodiments, the R-cloud is meaningful only in terms of its shape, and so is the model generated based on the R-cloud. Their position and orientation in space may be arbitrary.

This lack of reliance on a specified frame of reference is different from some prior art systems and methods, where a catheter is located and/or a body part is reconstructed in reference to an outer frame of reference, e.g., in respect to a pre-acquired image of the body part, in respect to a fiducial marker attached to the patient's skin, in respect of the patient's bed, etc. One scenario in which this difference matters is when the model is displayed for aiding a physician in carrying out a medical procedure inside the body cavity. Under such circumstances, the physician is usually interested in the location of the catheter in respect to the body part and some known structures in it. For example, if the physician is interested in treating the mitral valve, he may wish to know where his catheter is in respect to the mitral valve, and not in respect to the patient's bed, a fiducial, etc. Even a pre-acquired image is often less interesting than the current actual structure of the body part, which might have changed from the time the image had been acquired. Thus, prior art methods that rely on an extrinsic frame of reference need to correct for changes that may occur in this frame of reference or in the relationship between it and the body part, while systems and method according to some embodiments of the present inventions may be free from the need to carry out such corrections.

Instead (or in addition) of relying on a specified frame of reference, in some embodiments the transformation of measurement data into positions optionally relies on analyzing distances between reconstructed electrode positions. The distances, naturally, are independent on the coordinate system at which the positions are represented, so the frame of reference, even if existed, is immaterial to the analysis. The analysis optionally includes comparing distances of reconstructed electrode positions to a known distance between two electrodes carried on the probe at a known distance from each other.

One way to obtain a transformation that transforms measurements to reconstructed positions is by defining requirements regarding relationships between the reconstructed positions and themselves, and searching for a transformation that fulfills these requirements optimally or nearly so (e.g., at least to a desired accuracy). The requirements may rely on information existing on relationships between the positions of the electrodes and/or on general requirements from the reconstruction, like, for example, that it transforms measurements to locations in some "smooth" manner.

An example of information existing on relationships between locations of the electrodes is the distance between electrodes that are attached to the same probe. To the extent this distance is known, a requirement that this known distance is reproduced by the distances between corresponding points in the R-cloud may be set. Another example may be the requirement that the distance in R-cloud between locations attributed to electrodes affixed to the probe at a fixed distance will at least vary smoothly, if not kept constant at the known distance.

The requirements may be sometimes contradicting, so the method may include minimizing a cost function, which includes a penalty term for each such requirement. During system design, the relative weight of each penalty may be determined by trial and error, e.g., finding an optimal transformation using one set of weight between various penalties, studying the obtained model of the body part (e.g., by a human), and changing the weights if the result is not satisfactory. When the transformation is ready for use with the determined set of weights between penalties, measurements may be received, the transformation may be carried out using some initial parameters, and the cost function evaluated. This may be repeated with different sets of parameters to find a set that minimizes the cost. This minimization process may be carried out by algorithms known in the art. It is noted that in some embodiments, real distance between electrodes are also subject to change (e.g., replaced by calculated distances) in view of the penalty function.

In some embodiments, the method includes generating a plurality of transformations from the measurements based on different parameters; evaluating each of the plurality of transformations according to a cost function; and providing a transformation for generating the 3D model, based on the evaluating, for example, by selecting one transformation, modifying such a transformation and/or combining a plurality of said plurality of transformations.

In some embodiments, a transformation transforming the measurement cloud (also referred to herein as a V-cloud) to the R-cloud, may include a step of determining for each of the crossing electromagnetic fields a corresponding scaling coefficient, applicable to scale measurements of each said crossing electromagnetic field into a corresponding position along a physical position axis. For example, the transforming may include multiplying each measurement by a constant factor having a dimension of physical distance/measurement, for example, mm/mV. In some embodiments, this factor may be the same for each one of the crossing electromagnetic fields. In some embodiments, this factor may be different for each one of the crossing electromagnetic fields.

In some embodiments it may be the same for some of the crossing electromagnetic fields and different for other ones of the crossing electromagnetic fields. This may add to the flexibility of the resulting transformation, and may aid in finding a transformation that minimizes the cost. Also, considering each field propagates along a different direction (even if these directions differ from point to point and are not orthogonal to each other), it may be reasonable to assume that the measurement to location factor differs between different directions. In some embodiments, the measurement-to-location factor may also have a direction. This way, when three crossing electromagnetic fields are used, readings received simultaneously by one electrode of the three corresponding voltages ($V_1$, $V_2$, $V_3$) may be transformed into a location ($R_1$, $R_2$, $R_3$) wherein $$R_i = a_i V_i \hat{x}_i$$

Where a is the factor, and $\hat{x}$ is a unit vector at a certain direction. Optionally, the three unit vectors are perpendicular to each other. The above-mentioned scaling factor may be, for example, $a_i \hat{x}_i$. This way, an initial position in space is attributed to a measurement that was taken independent of any frame of reference. The initial positions attributed this way to all the measurements may be regarded an initial R-cloud.

In some embodiments, a transformation transforming the V-cloud to an R-cloud may include determining displacements applicable to each initial position attributed to measurements of the crossing electromagnetic fields to obtain from the intimal R-cloud a more optimal R-could, that is, an R-could associated with a smaller cost. Since the positions may be attributed to measurements almost randomly in the initial stage, there may be little point in evaluating the cost function of the initial R-cloud, and the displacement is always applied to it. In some embodiments, when searching for parameter values that minimize the cost, the values of the factors $a_i$ may be changed to achieve a lower cost.

In some embodiments, the displacement may be in intrinsic geometry of the V-cloud.

In accordance with some embodiments of the invention, a geometry is said to be "intrinsic" to the cloud, if distances are measured in this geometry along paths that go only through the cloud itself. One way to obtain an intrinsic geometry of a cloud, according to some embodiments of the present invention, is by decomposing a similarity matrix (preferably a normalized one) to its eigenvectors. For example, in some embodiments, the similarity matrix is the Gaussian Kernel (also known as the radial basis function kernel).

In some embodiments, the transformation is required to transform sister measurements to sister locations, distanced from each other by a desired sister-distance. As used herein, the term "sister measurements" refers to measurements taken substantially simultaneously by electrodes fixed to the probe at known distances from each other; sister locations are the locations to which the sister measurements are transformed by the transformation, "sister distances" are distances between sister locations, and desired sister-distances are the known distances between the electrodes on the probe.

In some embodiments, the reconstruction comprises transforming the V-cloud to an R-could regardless of outlying sister measurements. One inventive concept of some embodiments of the invention includes defining an outlying measurement as a measurement that by being disregarded helps "exceptionally" to find an optimal transformation. This is in difference from other methods of defining a measurement as outlying if the measurement itself lies outside some threshold. In general, disregarding a measurement always makes it easier to find an optimal transformation, as the number of requirements that the transformation should obey in order to be considered "optimal"—decreases. In some embodiments, the very act of disregarding a measurement is associated with a penalty. Optionally, a same penalty may be applied for disregarding any measurement. This penalty may be referred to as a penalty on disregard. Only if the cost function being minimized decreases, by disregarding a specific measurement, more than it increases due to the penalty on disregard, the specific measurement is considered an outlier. The penalty on disregard is preferably set to such a value, that a measurement is considered outlier only exceptionally (e.g., in 5%, 3%, 2%, 1%, or smaller or intermediate percentages of the time).

Another inventive concept in some embodiments of the present disclosure is related to a finding that under some circumstances, the model obtained is well-developed only along two dimensions and is relatively flat along the third dimension. To prevent occurrences of such "pancake" like models, in some embodiments, the measurements are pre-processed before they are used to find a best-fitting transform and using it to transform the measurements to electrode positions. The pre-processing may include manipulating the measurements to ensure that they have maximal variance between measurements taken from each electromagnetic field, and minimal covariance between measurements taken from different electromagnetic fields. Additionally or alternatively, a penalty may be added for highly dissimilar scaling coefficients. For example, the penalty may be applied proportionally to a harmonic average of the scaling factors $$\frac{1}{a_1} + \frac{1}{a_2} + \frac{1}{a_3}.$$

General

It is expected that during the life of a patent maturing from this application many relevant intrabody probes will be developed; the scope of the term intrabody probe is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A method of reconstructing a shape of a volume of a part of a subject based on intrabody measurements of a plurality of crossing electromagnetic fields established within the volume, the method comprising:
  receiving, by computer circuitry, measurements of the crossing electromagnetic fields carried out using at least one sensor carried on an intrabody probe, the measuring being carried out with the intrabody probe at multiple locations in the volume, to provide a set of measurement samples, taken at respective locations;

generating, by computer circuitry and through minimizing a cost function, a transformation that transforms the set of measurement samples to geometric positions;

transforming, using said generated transformation at least some of the measurements in said set of measurement samples into a set of geometric positions; and reconstructing the shape of said volume from said set of geometric positions;

wherein said generating and said transforming use only reference positions that are within said part of the subject;

wherein the cost function is evaluated during the minimizing, and, for each sample pair of a plurality of sample pairs of the set of measurement samples:
  transforming the sample pair into a corresponding position pair, and
  associating the position pair with a desired pair-distance; and wherein the cost function comprises a distance distortion penalty term that increases with an increase in absolute value of a difference between:
  distance separating positions of each corresponding position pair, and
  a respectively associated desired pair-distance.

2. A method according to claim 1, wherein the reconstructing uses fewer than half of the transformed measurements.

3. A method according to claim 1, comprising normalizing said set of measurement samples prior to said generating the transformation.

4. The method of claim 1, wherein the generating is performed independent of any information about the shape of said volume.

5. A method according to claim 1, wherein said generating is constrained using one or more constraints.

6. A method according to claim 5, wherein said one or more constraints comprise a constraint on relative positions of a plurality of the geometric positions to which said set of measurement samples is transformed.

7. A method according to claim 6, wherein said constraint comprises a coherence requirement.

8. A method according to claim 6, wherein said constraint comprises distance.

9. A method according to claim 5, wherein said one or more constraints comprise a constraint on a relationship between one or more samples of said set of measurement samples and one or more of said set of geometric positions.

10. A method according to claim 5, wherein said generating comprises allowing two samples of said set of measurement samples acquired at locations having a known distance therebetween to be transformed into positions at a different distance therebetween.

11. A method according to claim 1, wherein said generated transformation is not isotropic and varies in an amount of multiplication it applies over points in the reconstructed shape.

12. A method of claim 1, wherein generating the transformation comprises searching for the transformation under conditions of one or more constraints.

13. The method of claim 1, wherein the cost function comprises an anti-flattening penalty term; and wherein the anti-flattening penalty term increases as variance measured along an axis of the set of measurement samples becomes reduced relative to variance measured along other axes of said set.

14. The method of claim 1, wherein generating the transformation comprises minimizing variability in distances between positions assigned to nearby measurements in the set of measurement samples.

15. The method of claim 14, wherein a criterion of minimizing the variability comprises reducing differences between a transformation-based distance between transformed measurements and a known distance between locations where said measurements were made.

16. The method of claim 1, comprising scaling the set of measurement samples along different axes defined according to said crossing fields prior to said generating.

17. The method of claim 1, wherein said set of measurement samples comprise simultaneous measurements of multiple fields at one point, wherein each field has a different variation in a parameter thereof as a function of time.

18. The method of claim 1, wherein each position in said set of geometric positions includes a 3D spatial position.

19. The method of claim 1, wherein each position in said set of geometric positions is stamped with a timestamp.

20. The method of claim 1, wherein each position in said set of geometric positions is associated with a phase indication, indicating a phase in a physiological cycle, during which the set of measurements transformed into the set of geometric positions were measured.

21. A method according to claim 1, wherein reconstructing the shape comprises reconstructing the shape from the set of geometric positions using topological operators including dilation and erosion.

22. A method according to claim 1, wherein reconstructing the shape comprises reconstructing the shape of a heart or a part thereof.

23. A method according to claim 1, wherein said generating comprises generating without reference to a specified frame of reference.

24. A method according to claim 1, wherein said generating comprises generating based on relationships between reconstructed positions.

25. A method according to claim 1, wherein said generating and said transforming comprise, respectively, generating and transforming using only reference positions within said reconstructed shape.

26. A method according to claim 1, wherein said generating and said transforming comprise, respectively, generating and transforming using only reference positions that correspond to measurement locations.

27. A method according to claim 1, where said reconstructing uses fewer than half of said set of measurement samples.

28. A method according to claim 1, wherein the transforming comprises transforming fewer than half of the measurements in said set of measurement samples.

* * * * *